United States Patent
Hyde et al.

(10) Patent No.: US 11,214,815 B2
(45) Date of Patent: Jan. 4, 2022

(54) NUCLEIC ACID CONSTRUCT

(71) Applicant: IP2IPO INNOVATIONS LIMITED, London (GB)

(72) Inventors: Stephen Hyde, Oxford (GB); Deborah Gill, Oxford (GB)

(73) Assignee: IP2IPO INNOVATIONS LIMITED, London (GB)

( * ) Notice: Subject to any disclaimer, the term of this patent is extended or adjusted under 35 U.S.C. 154(b) by 347 days.

(21) Appl. No.: 14/519,117

(22) Filed: Oct. 20, 2014

(65) Prior Publication Data

US 2015/0232878 A1 Aug. 20, 2015

Related U.S. Application Data

(63) Continuation of application No. 12/294,498, filed as application No. PCT/GB2007/001104 on Mar. 28, 2007, now Pat. No. 8,871,503.

(30) Foreign Application Priority Data

Mar. 28, 2006 (GB) .................................... 0606190

(51) Int. Cl.
| | | |
|---|---|---|
| *C12N 15/85* | (2006.01) | |
| *A61K 48/00* | (2006.01) | |
| *C12N 15/67* | (2006.01) | |
| *A01K 67/027* | (2006.01) | |
| *C12N 15/113* | (2010.01) | |

(52) U.S. Cl.
CPC .......... *C12N 15/85* (2013.01); *A01K 67/0275* (2013.01); *A61K 48/0058* (2013.01); *C12N 15/113* (2013.01); *C12N 15/67* (2013.01); *C12N 15/8509* (2013.01); *A01K 2227/30* (2013.01); *A61K 48/00* (2013.01); *C12N 2830/00* (2013.01)

(58) Field of Classification Search
CPC .... A61K 48/0058; C12N 15/67; C12N 15/85; C12N 2830/00
See application file for complete search history.

(56) References Cited

U.S. PATENT DOCUMENTS

| | | | |
|---|---|---|---|
| 4,784,950 A | 11/1988 | Hagen et al. | |
| 4,868,112 A | 9/1989 | Toole, Jr. | |
| 4,965,199 A | 10/1990 | Capon et al. | |
| 4,994,371 A | 2/1991 | Davie et al. | |
| 5,122,458 A | 6/1992 | Post et al. | |
| 5,225,348 A | 7/1993 | Nagata et al. | |
| 5,236,838 A | 8/1993 | Rasmussen et al. | |
| 5,266,491 A | 11/1993 | Nagata et al. | |
| 5,283,185 A | 2/1994 | Epand et al. | |
| 5,382,524 A | 1/1995 | Desnick et al. | |
| 5,401,650 A | 3/1995 | Desnick et al. | |
| 5,527,928 A | 6/1996 | Nantz et al. | |
| 5,543,399 A | 8/1996 | Riordan et al. | |
| 5,661,008 A | 8/1997 | Almstedt et al. | |
| 5,674,898 A | 10/1997 | Cheng et al. | |
| 5,686,240 A | 11/1997 | Schuchman et al. | |
| 5,849,522 A | 12/1998 | Fleckenstein et al. | |
| 5,851,804 A | 12/1998 | Snyder et al. | |
| 5,863,770 A | 1/1999 | Tsui et al. | |
| 5,876,974 A | 3/1999 | Gregory | |
| 5,879,680 A | 3/1999 | Ginns et al. | |
| 6,063,913 A | 5/2000 | Tsui et al. | |
| 6,218,140 B1 | 4/2001 | Fleckenstein et al. | |
| 6,730,777 B1 | 5/2004 | Tsui et al. | |
| 6,902,907 B1 | 6/2005 | Tsui et al. | |
| 6,984,487 B1 | 1/2006 | Tsui et al. | |
| 7,074,590 B2 | 7/2006 | Punnomen et al. | |
| 7,118,911 B1 | 10/2006 | Gregory et al. | |
| 7,244,609 B2 | 7/2007 | Drocourt et al. | |
| 7,256,181 B2 | 8/2007 | Barsoum et al. | |
| 7,312,202 B2 | 12/2007 | Johnston et al. | |
| 8,871,503 B2 | 10/2014 | Hyde et al. | |
| 2003/0220277 A1* | 11/2003 | Yew ...................... | A61K 48/00 514/44 R |
| 2004/0219677 A1* | 11/2004 | Drocourt .............. | C07K 14/245 435/488 |
| 2007/0053879 A1 | 3/2007 | Gregory et al. | |
| 2007/0098690 A1 | 5/2007 | Ostedgaard et al. | |
| 2011/0035819 A1* | 2/2011 | Cooper ................ | A61K 48/005 800/14 |

FOREIGN PATENT DOCUMENTS

| | | |
|---|---|---|
| AU | 647408 | 4/1991 |
| CA | 2066204 | 2/1991 |
| CA | 2091907 | 2/1992 |

(Continued)

OTHER PUBLICATIONS

Kobayashi et al Analytical Biochemistry, 19997, 247, 179-181.*
Uetsuki et al (Journal of Biol. Chem. 1989, 264, 5791-5798.*
Yew et al Molecular therapy, 731-738 (Year: 2002).*
Kaiser Science, 317, 580 (Year: 2007).*
Thomas et al. Nature Rev.Genet. 4: 346-358 (Year: 2003).*
Ecke, Goodman & Gilman's The Pharmacological basis of Therapeutics, McGraw-Hill, New York, NY. pp. 77-101 (Year: 1996).*
Verma Annu Rev Biochem. 74: 711-38 (Year: 2005).*
Gill et al CMLS, Cell. Mol. Life Sci. 61 355-368 (Year: 2004).*
Davies et al. Proc Am Thorac Soc vol. 7. pp. 408-414, (Year: 2010).*

(Continued)

*Primary Examiner* — Anoop K Singh
(74) *Attorney, Agent, or Firm* — Wilson Sonsini Goodrich and Rosati

(57) ABSTRACT

A promoter for high level and sustained expression is provided which can be used for gene expression of chosen sequences in general. In particular, a nucleic acid construct comprising a hCEF1 promoter operably linked to a sequence for expression is provided, where the hCEF1 promoter comprises: (i) a human CMV enhancer operably linked to a human EF1 a promoter; (ii) a functional fragment of (i); or (ii) a functional variant of (i) or (ii).

7 Claims, 12 Drawing Sheets

Specification includes a Sequence Listing.

(56) References Cited

FOREIGN PATENT DOCUMENTS

| | | |
|---|---|---|
| CA | 1316852 | 4/1993 |
| CA | 2061579 | 8/1993 |
| CA | 2145641 | 6/1994 |
| CA | 2592997 | 6/1994 |
| CA | 2252845 | 11/1997 |
| CA | 2440195 | 9/2002 |
| CA | 2005016 | 3/2003 |
| CA | 2575490 | 2/2006 |
| CN | 1179470 | 4/1998 |
| EP | 0599850 | 3/1993 |
| EP | 0704530 A2 | 4/1996 |
| EP | 0938337 | 11/1997 |
| EP | 0702084 B1 | 12/1999 |
| EP | 0489058 | 11/2003 |
| EP | 1418183 A1 | 5/2004 |
| EP | 1452595 A | 9/2004 |
| EP | 1594955 | 9/2004 |
| EP | 1508620 | 2/2005 |
| EP | 1366176 | 8/2007 |
| EP | 1832657 | 9/2007 |
| NZ | 542316 | 4/2006 |
| WO | WO-9011092 A1 | 10/1990 |
| WO | WO 1991002796 | 3/1991 |
| WO | WO-9115501 A1 | 10/1991 |
| WO | WO 1992005252 | 4/1992 |
| WO | WO 1992005273 | 4/1992 |
| WO | WO-9310244 A1 | 5/1993 |
| WO | WO-9318759 A1 | 9/1993 |
| WO | WO 1993017040 | 9/1993 |
| WO | WO-9319768 A1 | 10/1993 |
| WO | WO 1994004671 | 3/1994 |
| WO | WO 1994012649 | 6/1994 |
| WO | WO-9507994 A2 | 3/1995 |
| WO | WO 1995007453 | 3/1995 |
| WO | WO-9526356 A1 | 10/1995 |
| WO | WO 1999018953 A | 4/1999 |
| WO | WO-0012740 A2 | 3/2000 |
| WO | WO 2000014262 | 3/2000 |
| WO | WO 2001075092 | 10/2001 |
| WO | WO 2002000897 | 1/2002 |
| WO | WO 2002072846 | 9/2002 |
| WO | WO 2004074439 A3 | 9/2004 |
| WO | WO2005028655 * | 3/2005 |

OTHER PUBLICATIONS

Gautam et al Am J Respir Med, ; 1(1):35-46 (Year: 2002).*
McCluskie et al Mol. Med. 5:287-300 (Year: 1999).*
Kobayashi, M., et al., "The CMV Enhancer Stimulates Expression of Foreign Genes from the Human EF-1α Paromoter," Analytical Biochemistry, Apr. 5, 1997, p. 179-181, vol. 247.
Pringle, I., et al., "Development of Zero-CpG Plasmids with Reduced Inflammatory Responses Following Delivery of Lipid/pDNA Complexes to the Mouse Lung," Molecular Therapy, May 2006, p. S304-S305, vol. 13, Supplement 1.
PCT International Search Report and Written Opinion, PCT/GB2007/001104, dated Feb. 20, 2008.
PCT International Preliminary Report on Patentability, PCT/GB2007/001104, dated Sep. 30, 2008.
Yew et al. Molecular therapy, 2002, 731-738.
Kaiser Science, 317, 2007, 580.
Verma et al. Annu Rev Biochem. 2005;74:711-38.
Ecke, Goodman & Gilman's The Pharmacological basis of Therapeutics, 1996, McGraw-Hill, New York, NY. pp. 77-101.
Gautam et al. (Am J Respir Med, 2002;1(1):35-46.
McCluskie et al. (1999) Mol. Med. 5:287-300.
Thomas et al. Nature Rev.Genet. 4: 346-358; 2003.
Xiao Mol Ther. 2000; 1(4):323-9.
United States Office Action, U.S. Appl. No. 12/294,498, dated Jan. 2, 2014, 16 pages.
United States Office Action, U.S. Appl. No. 12/294,498, dated Jul. 1, 2013, 15 pages.
United States Office Action, U.S. Appl. No. 12/294,498, dated Sep. 2, 2011, 14 pages.
United States Office Action, U.S. Appl. No. 12/294,498, dated Mar. 4, 2011, 12 pages.
Aitken et al.: A phase I study of aerosolized administration of tgAAVCF to cystic fibrosis subjects with mild lung disease. Hum Gene Ther. 12(15): 1907-1916 (2001).
Boussif, et al. A versatile vector for gene and oligonucleotide transfer into cells in culture and in vivo: Polyethylenimine. Proc. Natl. Acad. Sci. (U.S.A)., 1995, vol. 92, pp. 7297-7301.
Conrad et al.: Safety of single-dose administration of an adeno-associated virus (AAV)-CFTR vector in the primate lung. Gene Ther. 3(8): 658-668 (1996).
Crystal et al.: Administration of an adenovirus containing the human CFTR cDNA to the respiratory tract of individuals with cystic fibrosis. Nat Genet. 8(1): 42-51 (1994).
Derynck et al.: Human transforming growth factor-beta complementary DNA sequence and expression in normal and transformed cells. Nature 316: 701-705 (1985).
Devereux et al., "A comprehensive set of sequence analysis programs for the VAX," Nucl. Acids Res. 12(1):387-395 (1984).
Drumm et al.: Correction of the cystic fibrosis defect in vitro by retrovirus-mediated gene transfer. Cell. 62(6): 1227-1233 (1990).
Flotte et al.: Phase I trial of intranasal and endobronchial administration of a recombinant adeno-associated virus serotype 2 (rAAV2)-CFTR vector in adult cystic fibrosis patients: a two-part clinical study. Hum Gene Ther. 14(11): 1079-1788 (2003).
Gill et al.: Increased persistence of lung gene expression using plasmids containing the ubiquitin C or elongation factor 1alpha promoter. Gene Ther. 8(20): 1539-1546 (2001).
Gray et al.: Expression of human immune interferon cDNA in *E. coli* and monkey cells. Nature. 295(5849): 503-508 (1982).
Harvey et al.: Airway epithelial CFTR mRNA expression in cystic fibrosis patients after repetitive administration of a recombinant adenovirus. J Clin Invest. 104(9): 1245-1255 (1999).
Henikoff et al. Amino acid substitution matrices from protein blocks. PNAS USA 89(22):10915-10919 (1992).
Hyde et al.: Correction of the ion transport defect in cystic fibrosis transgenic mice by gene therapy. Nature. 362(6417): 250-255 (1993).
Idzerda et al.: Human interleukin 4 receptor confers biological responsiveness and defines a novel receptor superfamily. J. Exp. Med. 171(3): 861-873 (1990).
Jeffery et al.: The preparation and characterization of poly(lactide-co-glycolide) microparticles. II. The entrapment of a model protein using a (water-in-oil)-in-water emulsion solvent evaporation technique. Pharm Res. 10(3): 362-368 (1993).
Kerr et al.: Antibody-penicillin-V-amidase conjugates kill antigen-positive tumor cells when combined with doxorubicin phenoxyacetamide. Cancer Immunol Immunother. 31(4): 202-206 (1990).
Knowles et al.: A controlled study of adenoviral-vector-mediated gene transfer in the nasal epithelium of patients with cystic fibrosis. N Engl J Med. 333(13): 823-831 (1995).
Moss et al.: Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. 125(2): 509-521 (2004).
Mullen et al.: Transfer of the bacterial gene for cytosine deaminase to mammalian cells confers lethal sensitivity to 5-fluorocytosine: a negative selection system. Proc Natl Acad Sci U S A. 89(1): 33-37 (1992).
Pilewski et al.: Role of CFTR in airway disease. Physiol Rev. 79(1 Suppl): S215-255 (1999).
Riordan et al.: Identification of the cystic fibrosis gene: cloning and characterization of complementary DNA. Science. 245(4922): 1066-1073 (1989).
Santee et al.: Human tumor necrosis factor receptor p75/80 (CD120b) gene structure and promoter characterization. J Biol Chem. 271(35): 21151-21159 (1996).
Sims et al.: Cloning the interleukin 1 receptor from human T cells. Proc. Natl. Acad. Sci USA 86(22): 8946-8950 (1989).

(56) References Cited

OTHER PUBLICATIONS

Stevenson et al.: Thymidine phosphorylase activity and prodrug effects in a three-dimensional model of angiogenesis: implications for the treatment of ovarian cancer. Am J Pathol. 153(5): 1573-1578 (1998).

Sun et al. "Immune responses to adeno-associated virus and its recombinant vectors" Gene Ther, 2003, vol. 10, pp. 964-976.

Vieira et al.: Isolation and expression of human cytokine synthesis inhibitory factor cDNA clones: homology to Epstein-Barr virus open reading frame BCRFI. Proc Natl Acad Sci U S A. 88(4): 1172-1176 (1991).

Vrudhula et al.: Prodrugs of doxorubicin and melphalan and their activation by a monoclonal antibody-penicillin-G amidase conjugate. J Med Chem. 36(7): 919-923 (1993).

Wagner et al.: A phase II, double-blind, randomized, placebo-controlled clinical trial of tgAAVCF using maxillary sinus delivery in patients with cystic fibrosis with antrostomies. Hum Gene Ther. 13(11): 1349-1359 (2002).

Westphal et al.: The nitroreductase/CB1954 combination in Epstein-Barr virus-positive B-cell lines: induction of bystander killing in vitro and in vivo. Cancer Gene Ther. 7(1): 97-106 (2000).

Wilmott et al.: Safety of adenovirus-mediated transfer of the human cystic fibrosis transmembrane conductance regulator cDNA to the lungs of nonhuman primates. Hum Gene Ther. 7(3): 301-318 (1996).

Xie et al.: Efficacy of adenovirus-mediated CD/5-FC and HSV-1 thymidine kinase/ganciclovir suicide gene therapies concomitant with p53 gene therapy. Clin Cancer Res. 5(12): 4224-4232 (1999).

Zabner et al.: Repeat administration of an adenovirus vector encoding cystic fibrosis transmembrane conductance regulator to the nasal epithelium of patients with cystic fibrosis. J Clin Invest. 97(6): 1504-1511 (1996).

Hyde, Stephen C., et al., "CPG-Free Plasmids Confer Reduced Inflammation and Sustained Pulmonary Gene Expression", Nature Biology (2008) 26: 549-551.

\* cited by examiner

Figure 8

SEQUENCE LISTING

```
<160> NUMBER OF SEQ ID NOS: 5

<210> SEQ ID NO 1
<211> LENGTH: 2103
<212> TYPE: DNA
<213> ORGANISM: artificial sequence
<220> FEATURE:
<223> OTHER INFORMATION: pGM160 plasmid construct
<220> FEATURE:
<221> NAME/KEY: misc_feature
<222> LOCATION: (1)..(6)
<223> OTHER INFORMATION: BglII restriction site
<220> FEATURE:
<221> NAME/KEY: enhancer
<222> LOCATION: (7)..(308)
<223> OTHER INFORMATION: Human CMV enhancer
<220> FEATURE:
<221> NAME/KEY: misc_feature
<222> LOCATION: (309)..(314)
<223> OTHER INFORMATION: EcoRI restriction site
<220> FEATURE:
<221> NAME/KEY: promoter
<222> LOCATION: (315)..(538)
<223> OTHER INFORMATION: Human elongation factor 1 alpha promoter
```

```
<220> FEATURE:
<221> NAME/KEY: misc_feature
<222> LOCATION: (329)..(334)
<223> OTHER INFORMATION: SphI restriction enzyme site
<220> FEATURE:
<221> NAME/KEY: misc_feature
<222> LOCATION: (539)..(569)
<223> OTHER INFORMATION: Exon
<220> FEATURE:
<221> NAME/KEY: misc_feature
<222> LOCATION: (570)..(709)
<223> OTHER INFORMATION: Intron
<220> FEATURE:
<221> NAME/KEY: misc_feature
<222> LOCATION: (710)..(727)
<223> OTHER INFORMATION: Exon
<220> FEATURE:
<221> NAME/KEY: misc_feature
<222> LOCATION: (728)..(733)
<223> OTHER INFORMATION: NheI restriction site
<220> FEATURE:
<221> NAME/KEY: misc_feature
<222> LOCATION: (734)..(734)
<223> OTHER INFORMATION: A included to aviod CpG dinucleotide
<220> FEATURE:
<221> NAME/KEY: misc_feature
<222> LOCATION: (735)..(740)
<223> OTHER INFORMATION: ApaI restriction enzyme site
<220> FEATURE:
<221> NAME/KEY: polyA_signal
<222> LOCATION: (740)..(941)
<223> OTHER INFORMATION: Bovine growth hormone gene poly adenylation
     sequence
<220> FEATURE:
<221> NAME/KEY: misc_feature
<222> LOCATION: (936)..(941)
<223> OTHER INFORMATION: SphI restriction site within polyA
<220> FEATURE:
<221> NAME/KEY: misc_feature
<222> LOCATION: (942)..(942)
<223> OTHER INFORMATION: A included to avoid CpG dinucleotide
<220> FEATURE:
<221> NAME/KEY: misc_feature
<222> LOCATION: (943)..(1214)
<223> OTHER INFORMATION: R6K origin of replication
<220> FEATURE:
<221> NAME/KEY: misc_feature
<222> LOCATION: (1215)..(1215)
<223> OTHER INFORMATION: A included to avoid CpG dinucleotide
<220> FEATURE:
<221> NAME/KEY: misc_feature
<222> LOCATION: (1216)..(1221)
<223> OTHER INFORMATION: KpnI restriction site
<220> FEATURE:
<221> NAME/KEY: misc_feature
<222> LOCATION: (1222)..(2036)
<223> OTHER INFORMATION: Kanamycin resistance marker
<220> FEATURE:
<221> NAME/KEY: misc_feature
<222> LOCATION: (2038)..(2043)
<223> OTHER INFORMATION: Bam HI restriction site
<220> FEATURE:
<221> NAME/KEY: misc_feature
<222> LOCATION: (2044)..(2049)
<223> OTHER INFORMATION: Shine Delgarno ribosome binding site
<220> FEATURE:
<221> NAME/KEY: promoter
<222> LOCATION: (2050)..(2103)
<223> OTHER INFORMATION: EM7 bacterial promoter

<400> SEQUENCE: 1
agatctgtta cataacttat ggtaaatggc ctgcctggct gactgcccaa tgacccctgc    60
ccaatgatgt caataatgat gtatgttccc atgtaatgcc aatagggact ttccattgat   120
gtcaatgggt ggagtattta tggtaactgc ccacttggca gtacatcaag tgtatcatat   180
gccaagtatg cccctattg atgtcaatga tggtaaatgg cctgcctggc attatgccca   240
```

```
gtacatgacc ttatgggact ttcctacttg gcagtacatc tatgtattag tcattgctat    300
taccatggga attcactagt ggagaagagc atgcttgagg gctgagtgcc cctcagtggg    360
cagagagcac atggcccaca gtccctgaga agttgggggg aggggtgggc aattgaactg    420
gtgcctagag aaggtgggggc ttgggtaaac tgggaaagtg atgtggtgta ctggctccac   480 cttttttcccc agggtgggggg agaaccatat ataagtgcag tagtctctgt gaacattcaa   540
gcttctgcct tctccctcct gtgagtttgg taagtcactg actgtctatg cctgggaaag    600
ggtgggcagg agatggggca gtgcaggaaa agtggcacta tgaaccctgc agccctagga   660
atgcatctag acaattgtac taaccttctt ctctttcctc tcctgacagg ttggtgtaca    720
gtagcttgct agcagggccc tgtgccttct agttgccagc catctgttgt ttgcccctcc    780
cctgtgcctt ccttgaccct ggaaggtgcc actcccactg tcctttccta ataaaatgag    840
gaaattgcat tgcattgtct gagtaggtgt cattctattc tggggggtgg ggtggggcag    900
gacagcaagg gggaggattg ggaagacaat agcaggcatg cagatcagca gttcaacctg    960
ttgatagtat gtactaagct ctcatgttta atgtactaag ctctcatgtt taatgaacta   1020
aaccctcatg gctaatgtac taagctctca tggctaatgt actaagctct catgtttcat   1080
gtactaagct ctcatgtttg aacaataaaa ttaatataaa tcagcaactt aaatagcctc   1140
taaggtttta agttttataa gaaaaaaaag aatatataag gcttttaaag gttttaaggt   1200
ttcctaggtt atcctggtac cttagaaaaa ctcatccagc atcaaatgaa actgcaattt   1260
attcatatca ggattatcaa taccatattt ttgaaaaagt cttttctgta atgaaggaga   1320
aaactcaccc aggcagttcc ataggatggc aagatcctgg tatctgtctg caattccaac   1380
tcttccaaca tcaatacaac ctattaattt cccctcatca aaaataaggt tatcaagtga   1440
gaaatcacca tgagtgacca ctgaatctgg tgagaatggc aaaagcttat gcatttcttt   1500
ccagacttgt tcaacaggcc agccatttct ctcatcatca aaatcactgg catcaaccaa   1560
accattattc attcttgatt gggcctgagc cagtctaaat actctatcag agttaaaagg   1620
acaattacaa acaggaatgg aatgcaatct tctcaggaac actgccaggg catcaacaat   1680
attttcacct gaatcaggat attcttctaa tacctggaat gctgttttcc ctgggatggc   1740
agtggtgagt aaccatgcat catcaggagt tctgataaaa tgcttgatgg ttggaagagg   1800
cataaattca gtcagccagt ttagtctgac catctcatct gtaacatcat ggcaacaga    1860 acctttgcca tgtttcagaa acaactctgg ggcatctggc ttcccataca atctatagat   1920
tgtggcacct gattgcccaa cattatctct agcccattta tacccatata aatcagcatc   1980
catgttggaa tttaatcttg gcctggagca agaggtttct ctttgaatat ggctcatgga   2040
tccctcccta tagtgagttg tattatacta tgcagatata ctatgccaat gtttaattgt   2100
caa                                                                 2103
```

<210> SEQ ID NO 2
<211> LENGTH: 6549
<212> TYPE: DNA
<213> ORGANISM: Artificial sequence
<220> FEATURE:
<223> OTHER INFORMATION: plasmid construct
<220> FEATURE:
<221> NAME/KEY: misc_feature
<222> LOCATION: (1)..(6)
<223> OTHER INFORMATION: BglII restriction enzyme site
<220> FEATURE:
<221> NAME/KEY: misc_feature
<222> LOCATION: (7)..(308)

```
<223> OTHER INFORMATION: Human CMV enhancer
<220> FEATURE:
<221> NAME/KEY: misc_feature
<222> LOCATION: (309)..(314)
<223> OTHER INFORMATION: Eco RI restriction site
<220> FEATURE:
<221> NAME/KEY: promoter
<222> LOCATION: (315)..(538)
<223> OTHER INFORMATION: Human Elongation Factor 1 alpha promoter
<220> FEATURE:
<221> NAME/KEY: misc_feature
<222> LOCATION: (329)..(334)
<223> OTHER INFORMATION: Sph I restriction site
<220> FEATURE:
<221> NAME/KEY: misc_feature
<222> LOCATION: (539)..(569)
<223> OTHER INFORMATION: exon
<220> FEATURE:
<221> NAME/KEY: Intron
<222> LOCATION: (570)..(709)
<223> OTHER INFORMATION: Intron
<220> FEATURE:
<221> NAME/KEY: misc_feature
<222> LOCATION: (710)..(727)
<223> OTHER INFORMATION: exon
<220> FEATURE:
<221> NAME/KEY: misc_feature
<222> LOCATION: (728)..(733)
<223> OTHER INFORMATION: Nhe I restriction site
<220> FEATURE:
<221> NAME/KEY: misc_feature
<222> LOCATION: (733)..(737)
<223> OTHER INFORMATION: Kozak sequence
<220> FEATURE:
<221> NAME/KEY: CDS
<222> LOCATION: (738)..(5180)
<223> OTHER INFORMATION: codon optimised CFTR cDNA
<220> FEATURE:
<221> NAME/KEY: misc_feature
<222> LOCATION: (1183)..(1188)
<223> OTHER INFORMATION: Sph I restriction site
<220> FEATURE:
<221> NAME/KEY: misc_feature
<222> LOCATION: (4865)..(4870)
<223> OTHER INFORMATION: Bam HI restriction site
<220> FEATURE:
<221> NAME/KEY: polyA_signal
<222> LOCATION: (5181)..(5186)
<223> OTHER INFORMATION: ApaI restriction site
<220> FEATURE:
<221> NAME/KEY: polyA_signal
<222> LOCATION: (5186)..(5387)
<223> OTHER INFORMATION: Bovine growth hormone gene poly A sequence
<220> FEATURE:
<221> NAME/KEY: misc_feature
<222> LOCATION: (5382)..(5387)
<223> OTHER INFORMATION: Sph I restriction site within poly A
<220> FEATURE:
<221> NAME/KEY: misc_feature
<222> LOCATION: (5388)..(5388)
<223> OTHER INFORMATION: A included to avoid occurrence of cpg
      dinculeotide
<220> FEATURE:
<221> NAME/KEY: rep_origin
<222> LOCATION: (5389)..(5660)
<223> OTHER INFORMATION: R6K origin of replication
<220> FEATURE:
<221> NAME/KEY: misc_feature
<222> LOCATION: (5661)..(5661)
<223> OTHER INFORMATION: A included to avoid occurrence of cpg
      dinucleotide
<220> FEATURE:
<221> NAME/KEY: misc_feature
<222> LOCATION: (5662)..(5667)
<223> OTHER INFORMATION: kpn I restriction site
<220> FEATURE:
<221> NAME/KEY: misc_feature
<222> LOCATION: (5668)..(6483)
<223> OTHER INFORMATION: Kanamycin resistance marker
```

```
<220> FEATURE:
<221> NAME/KEY: misc_feature
<222> LOCATION: (6484)..(6489)
<223> OTHER INFORMATION: Bam Hi restriction site
<220> FEATURE:
<221> NAME/KEY: misc_feature
<222> LOCATION: (6490)..(6495)
<223> OTHER INFORMATION: shine delgarno ribosome binding site
<220> FEATURE:
<221> NAME/KEY: promoter
<222> LOCATION: (6496)..(6549)
<223> OTHER INFORMATION: EM7 bacterial promoter

<400> SEQUENCE: 2
agatctgtta cataacttat ggtaaatggc ctgcctggct gactgcccaa tgacccctgc      60
ccaatgatgt caataatgat gtatgttccc atgtaatgcc aatagggact ttccattgat     120
gtcaatgggt ggagtattta tggtaactgc ccacttggca gtacatcaag tgtatcatat     180
gccaagtatg ccccctattg atgtcaatga tggtaaatgg cctgcctggc attatgccca     240
gtacatgacc ttatgggact ttcctacttg gcagtacatc tatgtattag tcattgctat     300
taccatggga attcactagt ggagaagagc atgcttgagg gctgagtgcc cctcagtggg     360
cagagagcac atgcccaca gtccctgaga agttgggggg aggggtgggc aattgaactg     420
gtgcctagag aaggtggggc ttgggtaaac tgggaaagtg atgtggtgta ctggctccac     480 cttttttcccc agggtggggg agaaccatat ataagtgcag tagtctctgt gaacattcaa     540
gcttctgcct tctccctcct gtgagtttgg taagtcactg actgtctatg cctgggaaag     600
ggtgggcagg agatggggca gtgcaggaaa agtggcacta tgaaccctgc agccctagga     660
atgcatctag acaattgtac taaccttctt ctctttcctc tcctgacagg ttggtgtaca     720
gtagcttgct agccacc atg cag aga agc cct ctg gag aag gcc tct gtg        770
              Met Gln Arg Ser Pro Leu Glu Lys Ala Ser Val
              1               5                  10 gtg agc aag ctg ttc ttc agc tgg acc agg ccc atc ctg agg aag ggc        818
Val Ser Lys Leu Phe Phe Ser Trp Thr Arg Pro Ile Leu Arg Lys Gly
         15                 20                 25 tac agg cag aga ctg gag ctg tct gac atc tac cag atc ccc tct gtg        866
Tyr Arg Gln Arg Leu Glu Leu Ser Asp Ile Tyr Gln Ile Pro Ser Val
     30                 35                 40 gac tct gct gac aac ctg tct gag aag ctg gag agg gag tgg gat aga        914
Asp Ser Ala Asp Asn Leu Ser Glu Lys Leu Glu Arg Glu Trp Asp Arg
 45                 50                 55 gag ctg gcc agc aag aag aac ccc aag ctg atc aat gcc ctg agg aga        962
Glu Leu Ala Ser Lys Lys Asn Pro Lys Leu Ile Asn Ala Leu Arg Arg
60                 65                 70                 75 tgc ttc ttc tgg aga ttc atg ttc tat ggc atc ttc ctg tac ctg ggg       1010
Cys Phe Phe Trp Arg Phe Met Phe Tyr Gly Ile Phe Leu Tyr Leu Gly
                 80                 85                 90 gaa gtg acc aag gct gtg cag cct ctg ctg ctg ggc aga atc att gcc       1058
Glu Val Thr Lys Ala Val Gln Pro Leu Leu Leu Gly Arg Ile Ile Ala
             95                100                105 agc tat gac cct gac aac aag gag gag agg agc att gcc atc tac ctg       1106
Ser Tyr Asp Pro Asp Asn Lys Glu Glu Arg Ser Ile Ala Ile Tyr Leu
        110                115                120 ggc att ggc ctg tgc ctg ctg ttc att gtg agg acc ctg ctg ctg cac       1154
Gly Ile Gly Leu Cys Leu Leu Phe Ile Val Arg Thr Leu Leu Leu His
    125                130                135 cct gcc atc ttt ggc ctg cac cac att ggc atg cag atg agg att gcc       1202
Pro Ala Ile Phe Gly Leu His His Ile Gly Met Gln Met Arg Ile Ala
140                145                150                155
```

```
                                                        -continued atg ttc agc ctg atc tac aag aaa acc ctg aag ctg tcc agc aga gtg      1250
Met Phe Ser Leu Ile Tyr Lys Lys Thr Leu Lys Leu Ser Ser Arg Val
            160                 165                 170 ctg gac aag atc agc att ggc cag ctg gtg agc ctg ctg agc aac aac      1298
Leu Asp Lys Ile Ser Ile Gly Gln Leu Val Ser Leu Leu Ser Asn Asn
    175                 180                 185 ctg aac aag ttt gat gag ggc ctg gcc ctg gcc cac ttt gtg tgg att      1346
Leu Asn Lys Phe Asp Glu Gly Leu Ala Leu Ala His Phe Val Trp Ile
190                 195                 200 gcc cct ctg cag gtg gcc ctg ctg atg ggc ctg att tgg gag ctg ctg      1394
Ala Pro Leu Gln Val Ala Leu Leu Met Gly Leu Ile Trp Glu Leu Leu
            205                 210                 215 cag gcc tct gcc ttt tgt ggc ctg ggc ttc ctg att gtg ctg gcc ctg      1442
Gln Ala Ser Ala Phe Cys Gly Leu Gly Phe Leu Ile Val Leu Ala Leu
220                 225                 230                 235 ttt cag gct ggc ctg ggc agg atg atg atg aag tac agg gac cag agg      1490
Phe Gln Ala Gly Leu Gly Arg Met Met Met Lys Tyr Arg Asp Gln Arg
                240                 245                 250 gca ggc aag atc agt gag agg ctg gtg atc acc tct gag atg att gag      1538
Ala Gly Lys Ile Ser Glu Arg Leu Val Ile Thr Ser Glu Met Ile Glu
            255                 260                 265 aac atc cag tct gtg aag gcc tac tgt tgg gag gaa gct atg gag aag      1586
Asn Ile Gln Ser Val Lys Ala Tyr Cys Trp Glu Glu Ala Met Glu Lys
    270                 275                 280 atg att gaa aac ctg agg cag aca gag ctg aag ctg acc agg aag gct      1634
Met Ile Glu Asn Leu Arg Gln Thr Glu Leu Lys Leu Thr Arg Lys Ala
285                 290                 295 gcc tat gtg aga tac ttc aac agc tct gcc ttc ttc ttc tct ggc ttc      1682
Ala Tyr Val Arg Tyr Phe Asn Ser Ser Ala Phe Phe Phe Ser Gly Phe
            300                 305                 310                 315 ttt gtg gtg ttc ctg tct gtg ctg ccc tat gcc ctg atc aag ggg atc      1730
Phe Val Val Phe Leu Ser Val Leu Pro Tyr Ala Leu Ile Lys Gly Ile
                320                 325                 330 atc ctg aga aag att ttc acc acc atc agc ttc tgc att gtg ctg agg      1778
Ile Leu Arg Lys Ile Phe Thr Thr Ile Ser Phe Cys Ile Val Leu Arg
            335                 340                 345 atg gct gtg acc aga cag ttc ccc tgg gct gtg cag acc tgg tat gac      1826
Met Ala Val Thr Arg Gln Phe Pro Trp Ala Val Gln Thr Trp Tyr Asp
    350                 355                 360 agc ctg ggg gcc atc aac aag atc cag gac ttc ctg cag aag cag gag      1874
Ser Leu Gly Ala Ile Asn Lys Ile Gln Asp Phe Leu Gln Lys Gln Glu
365                 370                 375 tac aag acc ctg gag tac aac ctg acc acc aca gaa gtg gtg atg gag      1922
Tyr Lys Thr Leu Glu Tyr Asn Leu Thr Thr Thr Glu Val Val Met Glu
            380                 385                 390                 395 aat gtg aca gcc ttc tgg gag gag ggc ttt ggg gag ctg ttt gag aag      1970
Asn Val Thr Ala Phe Trp Glu Glu Gly Phe Gly Glu Leu Phe Glu Lys
                400                 405                 410 gcc aag cag aac aac aac aac aga aag acc agc aat ggg gat gac tcc      2018
Ala Lys Gln Asn Asn Asn Asn Arg Lys Thr Ser Asn Gly Asp Asp Ser
            415                 420                 425 ctg ttc ttc tcc aac ttc tcc ctg ctg ggc aca cct gtg ctg aag gac      2066
Leu Phe Phe Ser Asn Phe Ser Leu Leu Gly Thr Pro Val Leu Lys Asp
    430                 435                 440 atc aac ttc aag att gag agg ggg cag ctg ctg gct gtg gct gga tct      2114
Ile Asn Phe Lys Ile Glu Arg Gly Gln Leu Leu Ala Val Ala Gly Ser
445                 450                 455 aca ggg gct ggc aag acc agc ctg ctg atg atg atc atg ggg gag ctg      2162
Thr Gly Ala Gly Lys Thr Ser Leu Leu Met Met Ile Met Gly Glu Leu
460                 465                 470                 475
```

```
gag cct tct gag ggc aag atc aag cac tct ggc agg atc agc ttt tgc     2210
Glu Pro Ser Glu Gly Lys Ile Lys His Ser Gly Arg Ile Ser Phe Cys
            480                 485                 490 agc cag ttc agc tgg atc atg cct ggc acc atc aag gag aac atc atc     2258
Ser Gln Phe Ser Trp Ile Met Pro Gly Thr Ile Lys Glu Asn Ile Ile
        495                 500                 505 ttt gga gtg agc tat gat gag tac aga tac agg agt gtg atc aag gcc     2306
Phe Gly Val Ser Tyr Asp Glu Tyr Arg Tyr Arg Ser Val Ile Lys Ala
    510                 515                 520 tgc cag ctg gag gag gac atc agc aag ttt gct gag aag gac aac att     2354
Cys Gln Leu Glu Glu Asp Ile Ser Lys Phe Ala Glu Lys Asp Asn Ile
525                 530                 535 gtg ctg ggg gag gga ggc att aca ctg tct ggg ggc cag aga gcc aga     2402
Val Leu Gly Glu Gly Gly Ile Thr Leu Ser Gly Gly Gln Arg Ala Arg
540                 545                 550                 555 atc agc ctg gcc agg gct gtg tac aag gat gct gac ctg tac ctg ctg     2450
Ile Ser Leu Ala Arg Ala Val Tyr Lys Asp Ala Asp Leu Tyr Leu Leu
            560                 565                 570 gac tcc ccc ttt ggc tac ctg gat gtg ctg aca gag aag gag att ttt     2498
Asp Ser Pro Phe Gly Tyr Leu Asp Val Leu Thr Glu Lys Glu Ile Phe
        575                 580                 585 gag agc tgt gtg tgc aag ctg atg gcc aac aag acc aga atc ctg gtg     2546
Glu Ser Cys Val Cys Lys Leu Met Ala Asn Lys Thr Arg Ile Leu Val
    590                 595                 600 acc agc aag atg gag cac ctg aag aag gct gac aag atc ctg atc ctg     2594
Thr Ser Lys Met Glu His Leu Lys Lys Ala Asp Lys Ile Leu Ile Leu
605                 610                 615 aat gag ggc agc agc tac ttc tat ggg acc ttc tct gag ctg cag aac     2642
Asn Glu Gly Ser Ser Tyr Phe Tyr Gly Thr Phe Ser Glu Leu Gln Asn
620                 625                 630                 635 ctg cag cct gac ttc agc tct aag ctg atg ggc tgt gac agc ttt gac     2690
Leu Gln Pro Asp Phe Ser Ser Lys Leu Met Gly Cys Asp Ser Phe Asp
            640                 645                 650 cag ttc tct gct gag agg agg aac agc atc ctg aca gag acc ctg cac     2738
Gln Phe Ser Ala Glu Arg Arg Asn Ser Ile Leu Thr Glu Thr Leu His
        655                 660                 665 aga ttc agc ctg gag gga gat gcc cct gtg agc tgg aca gag acc aag     2786
Arg Phe Ser Leu Glu Gly Asp Ala Pro Val Ser Trp Thr Glu Thr Lys
    670                 675                 680 aag cag agc ttc aag cag aca ggg gag ttt ggg gag aag agg aag aac     2834
Lys Gln Ser Phe Lys Gln Thr Gly Glu Phe Gly Glu Lys Arg Lys Asn
685                 690                 695 tcc atc ctg aac ccc atc aac agc atc agg aag ttc agc att gtg cag     2882
Ser Ile Leu Asn Pro Ile Asn Ser Ile Arg Lys Phe Ser Ile Val Gln
700                 705                 710                 715 aaa acc ccc ctg cag atg aat ggc att gag gaa gat tct gat gag ccc     2930
Lys Thr Pro Leu Gln Met Asn Gly Ile Glu Glu Asp Ser Asp Glu Pro
            720                 725                 730 ctg gag agg aga ctg agc ctg gtg cct gat tct gag cag gga gag gcc     2978
Leu Glu Arg Arg Leu Ser Leu Val Pro Asp Ser Glu Gln Gly Glu Ala
        735                 740                 745 atc ctg cct agg atc tct gtg atc agc aca ggc cct aca ctg cag gcc     3026
Ile Leu Pro Arg Ile Ser Val Ile Ser Thr Gly Pro Thr Leu Gln Ala
    750                 755                 760 aga agg agg cag tct gtg ctg aac ctg atg acc cac tct gtg aac cag     3074
Arg Arg Arg Gln Ser Val Leu Asn Leu Met Thr His Ser Val Asn Gln
765                 770                 775 ggc cag aac atc cac agg aaa acc aca gcc tcc acc agg aaa gtg agc     3122
Gly Gln Asn Ile His Arg Lys Thr Thr Ala Ser Thr Arg Lys Val Ser
```

-continued

| | |
|---|---|
| ctg gcc cct cag gcc aat ctg aca gag ctg gac atc tac agc agg agg<br>Leu Ala Pro Gln Ala Asn Leu Thr Glu Leu Asp Ile Tyr Ser Arg Arg<br>800                     805                  810 | 3170 |
| ctg tct cag gag aca ggc ctg gag att tct gag gag atc aat gag gag<br>Leu Ser Gln Glu Thr Gly Leu Glu Ile Ser Glu Glu Ile Asn Glu Glu<br>815                  820                 825 | 3218 |
| gac ctg aaa gag tgc ctg ttt gat gac atg gag agc atc cct gct gtg<br>Asp Leu Lys Glu Cys Leu Phe Asp Asp Met Glu Ser Ile Pro Ala Val<br>830                  835                840 | 3266 |
| acc acc tgg aac acc tac ctg aga tac atc aca gtg cac aag agc ctg<br>Thr Thr Trp Asn Thr Tyr Leu Arg Tyr Ile Thr Val His Lys Ser Leu<br>845                  850                855 | 3314 |
| atc ttt gtg ctg atc tgg tgc ctg gtg atc ttc ctg gct gaa gtg gct<br>Ile Phe Val Leu Ile Trp Cys Leu Val Ile Phe Leu Ala Glu Val Ala<br>860                  865                870              875 | 3362 |
| gcc tct ctg gtg gtg ctg tgg ctg ctg gga aac acc cca ctg cag gac<br>Ala Ser Leu Val Val Leu Trp Leu Leu Gly Asn Thr Pro Leu Gln Asp<br>880                  885                890 | 3410 |
| aag ggc aac agc acc cac agc agg aac aac agc tat gct gtg atc atc<br>Lys Gly Asn Ser Thr His Ser Arg Asn Asn Ser Tyr Ala Val Ile Ile<br>895                  900                905 | 3458 |
| acc tcc acc tcc agc tac tat gtg ttc tac atc tat gtg gga gtg gct<br>Thr Ser Thr Ser Ser Tyr Tyr Val Phe Tyr Ile Tyr Val Gly Val Ala<br>910                  915                920 | 3506 |
| gat acc ctg ctg gct atg ggc ttc ttt aga ggc ctg ccc ctg gtg cac<br>Asp Thr Leu Leu Ala Met Gly Phe Phe Arg Gly Leu Pro Leu Val His<br>925                  930                935 | 3554 |
| aca ctg atc aca gtg agc aag atc ctc cac cac aag atg ctg cac tct<br>Thr Leu Ile Thr Val Ser Lys Ile Leu His His Lys Met Leu His Ser<br>940                  945                950              955 | 3602 |
| gtg ctg cag gct cct atg agc acc ctg aat acc ctg aag gct ggg ggc<br>Val Leu Gln Ala Pro Met Ser Thr Leu Asn Thr Leu Lys Ala Gly Gly<br>960                  965                970 | 3650 |
| atc ctg aac aga ttc tcc aag gat att gcc atc ctg gat gac ctg ctg<br>Ile Leu Asn Arg Phe Ser Lys Asp Ile Ala Ile Leu Asp Asp Leu Leu<br>975                  980                985 | 3698 |
| cct ctc acc atc ttt gac ttc atc cag ctg ctg ctg att gtg att ggg<br>Pro Leu Thr Ile Phe Asp Phe Ile Gln Leu Leu Leu Ile Val Ile Gly<br>990                  995                1000 | 3746 |
| gcc att gct gtg gtg gca gtg ctg cag ccc tac atc ttt gtg gcc<br>Ala Ile Ala Val Val Ala Val Leu Gln Pro Tyr Ile Phe Val Ala<br>1005                 1010                1015 | 3791 |
| aca gtg cct gtg att gtg gcc ttc atc atg ctg agg gcc tac ttt<br>Thr Val Pro Val Ile Val Ala Phe Ile Met Leu Arg Ala Tyr Phe<br>1020                1025               1030 | 3836 |
| ctg cag acc tcc cag cag ctg aag cag ctg gag tct gag ggc aga<br>Leu Gln Thr Ser Gln Gln Leu Lys Gln Leu Glu Ser Glu Gly Arg<br>1035                1040               1045 | 3881 |
| agc ccc atc ttc acc cac ctg gtg aca agc ctg aag ggc ctg tgg<br>Ser Pro Ile Phe Thr His Leu Val Thr Ser Leu Lys Gly Leu Trp<br>1050                1055               1060 | 3926 |
| acc ctg aga gcc ttt ggc agg cag ccc tac ttt gag acc ctg ttc<br>Thr Leu Arg Ala Phe Gly Arg Gln Pro Tyr Phe Glu Thr Leu Phe<br>1065                1070               1075 | 3971 |
| cac aag gcc ctg aac ctg cac aca gcc aac tgg ttc ctc tac ctg<br>His Lys Ala Leu Asn Leu His Thr Ala Asn Trp Phe Leu Tyr Leu<br>1080                1085               1090 | 4016 |
| tcc acc ctg aga tgg ttc cag atg aga att gag atg atc ttt gtc | 4061 |

-continued

| | | | | | | | | | | | | | | | |
|---|---|---|---|---|---|---|---|---|---|---|---|---|---|---|---|
| Ser | Thr | Leu | Arg | Trp | Phe | Gln | Met | Arg | Ile | Glu | Met | Ile | Phe | Val | |
| | 1095 | | | | 1100 | | | | 1105 | | | | | | |

| atc | ttc | ttc | att | gct | gtg | acc | ttc | atc | agc | att | ctg | acc | aca | gga | 4106 |
|---|---|---|---|---|---|---|---|---|---|---|---|---|---|---|---|
| Ile | Phe | Phe | Ile | Ala | Val | Thr | Phe | Ile | Ser | Ile | Leu | Thr | Thr | Gly | |
| 1110 | | | | | 1115 | | | | | 1120 | | | | | |

| gag | gga | gag | ggc | aga | gtg | ggc | att | atc | ctg | acc | ctg | gcc | atg | aac | 4151 |
|---|---|---|---|---|---|---|---|---|---|---|---|---|---|---|---|
| Glu | Gly | Glu | Gly | Arg | Val | Gly | Ile | Ile | Leu | Thr | Leu | Ala | Met | Asn | |
| 1125 | | | | | 1130 | | | | | 1135 | | | | | |

| atc | atg | agc | aca | ctg | cag | tgg | gca | gtg | aac | agc | agc | att | gat | gtg | 4196 |
|---|---|---|---|---|---|---|---|---|---|---|---|---|---|---|---|
| Ile | Met | Ser | Thr | Leu | Gln | Trp | Ala | Val | Asn | Ser | Ser | Ile | Asp | Val | |
| 1140 | | | | | 1145 | | | | | 1150 | | | | | |

| gac | agc | ctg | atg | agg | agt | gtg | agc | aga | gtg | ttc | aag | ttc | att | gat | 4241 |
|---|---|---|---|---|---|---|---|---|---|---|---|---|---|---|---|
| Asp | Ser | Leu | Met | Arg | Ser | Val | Ser | Arg | Val | Phe | Lys | Phe | Ile | Asp | |
| 1155 | | | | | 1160 | | | | | 1165 | | | | | |

| atg | ccc | aca | gag | ggc | aag | cct | acc | aag | agc | acc | aag | ccc | tac | aag | 4286 |
|---|---|---|---|---|---|---|---|---|---|---|---|---|---|---|---|
| Met | Pro | Thr | Glu | Gly | Lys | Pro | Thr | Lys | Ser | Thr | Lys | Pro | Tyr | Lys | |
| 1170 | | | | | 1175 | | | | | 1180 | | | | | |

| aat | ggc | cag | ctg | agc | aaa | gtg | atg | atc | att | gag | aac | agc | cat | gtg | 4331 |
|---|---|---|---|---|---|---|---|---|---|---|---|---|---|---|---|
| Asn | Gly | Gln | Leu | Ser | Lys | Val | Met | Ile | Ile | Glu | Asn | Ser | His | Val | |
| 1185 | | | | | 1190 | | | | | 1195 | | | | | |

| aag | aag | gat | gat | atc | tgg | ccc | agt | gga | ggc | cag | atg | aca | gtg | aag | 4376 |
|---|---|---|---|---|---|---|---|---|---|---|---|---|---|---|---|
| Lys | Lys | Asp | Asp | Ile | Trp | Pro | Ser | Gly | Gly | Gln | Met | Thr | Val | Lys | |
| 1200 | | | | | 1205 | | | | | 1210 | | | | | |

| gac | ctg | aca | gcc | aag | tac | aca | gag | ggg | ggc | aat | gct | atc | ctg | gag | 4421 |
|---|---|---|---|---|---|---|---|---|---|---|---|---|---|---|---|
| Asp | Leu | Thr | Ala | Lys | Tyr | Thr | Glu | Gly | Gly | Asn | Ala | Ile | Leu | Glu | |
| 1215 | | | | | 1220 | | | | | 1225 | | | | | |

| aac | atc | tcc | ttc | agc | atc | tcc | cct | ggc | cag | aga | gtg | gga | ctg | ctg | 4466 |
|---|---|---|---|---|---|---|---|---|---|---|---|---|---|---|---|
| Asn | Ile | Ser | Phe | Ser | Ile | Ser | Pro | Gly | Gln | Arg | Val | Gly | Leu | Leu | |
| 1230 | | | | | 1235 | | | | | 1240 | | | | | |

| gga | aga | aca | ggc | tct | ggc | aag | tct | acc | ctg | ctg | tct | gcc | ttc | ctg | 4511 |
|---|---|---|---|---|---|---|---|---|---|---|---|---|---|---|---|
| Gly | Arg | Thr | Gly | Ser | Gly | Lys | Ser | Thr | Leu | Leu | Ser | Ala | Phe | Leu | |
| 1245 | | | | | 1250 | | | | | 1255 | | | | | |

| agg | ctg | ctg | aac | aca | gag | gga | gag | atc | cag | att | gat | gga | gtg | tcc | 4556 |
|---|---|---|---|---|---|---|---|---|---|---|---|---|---|---|---|
| Arg | Leu | Leu | Asn | Thr | Glu | Gly | Glu | Ile | Gln | Ile | Asp | Gly | Val | Ser | |
| 1260 | | | | | 1265 | | | | | 1270 | | | | | |

| tgg | gac | agc | atc | aca | ctg | cag | cag | tgg | agg | aag | gcc | ttt | ggt | gtg | 4601 |
|---|---|---|---|---|---|---|---|---|---|---|---|---|---|---|---|
| Trp | Asp | Ser | Ile | Thr | Leu | Gln | Gln | Trp | Arg | Lys | Ala | Phe | Gly | Val | |
| 1275 | | | | | 1280 | | | | | 1285 | | | | | |

| atc | ccc | cag | aaa | gtg | ttc | atc | ttc | agt | ggc | acc | ttc | agg | aag | aac | 4646 |
|---|---|---|---|---|---|---|---|---|---|---|---|---|---|---|---|
| Ile | Pro | Gln | Lys | Val | Phe | Ile | Phe | Ser | Gly | Thr | Phe | Arg | Lys | Asn | |
| 1290 | | | | | 1295 | | | | | 1300 | | | | | |

| ctg | gac | ccc | tat | gag | cag | tgg | tct | gac | cag | gag | att | tgg | aaa | gtg | 4691 |
|---|---|---|---|---|---|---|---|---|---|---|---|---|---|---|---|
| Leu | Asp | Pro | Tyr | Glu | Gln | Trp | Ser | Asp | Gln | Glu | Ile | Trp | Lys | Val | |
| 1305 | | | | | 1310 | | | | | 1315 | | | | | |

| gct | gat | gaa | gtg | ggc | ctg | aga | agt | gtg | att | gag | cag | ttc | cct | ggc | 4736 |
|---|---|---|---|---|---|---|---|---|---|---|---|---|---|---|---|
| Ala | Asp | Glu | Val | Gly | Leu | Arg | Ser | Val | Ile | Glu | Gln | Phe | Pro | Gly | |
| 1320 | | | | | 1325 | | | | | 1330 | | | | | |

| aag | ctg | gac | ttt | gtc | ctg | gtg | gat | ggg | ggc | tgt | gtg | ctg | agc | cat | 4781 |
|---|---|---|---|---|---|---|---|---|---|---|---|---|---|---|---|
| Lys | Leu | Asp | Phe | Val | Leu | Val | Asp | Gly | Gly | Cys | Val | Leu | Ser | His | |
| 1335 | | | | | 1340 | | | | | 1345 | | | | | |

| ggc | cac | aag | cag | ctg | atg | tgc | ctg | gcc | aga | tca | gtg | ctg | agc | aag | 4826 |
|---|---|---|---|---|---|---|---|---|---|---|---|---|---|---|---|
| Gly | His | Lys | Gln | Leu | Met | Cys | Leu | Ala | Arg | Ser | Val | Leu | Ser | Lys | |
| 1350 | | | | | 1355 | | | | | 1360 | | | | | |

| gcc | aag | atc | ctg | ctg | ctg | gat | gag | cct | tct | gcc | cac | ctg | gat | cct | 4871 |
|---|---|---|---|---|---|---|---|---|---|---|---|---|---|---|---|
| Ala | Lys | Ile | Leu | Leu | Leu | Asp | Glu | Pro | Ser | Ala | His | Leu | Asp | Pro | |
| 1365 | | | | | 1370 | | | | | 1375 | | | | | |

| gtg | acc | tac | cag | atc | atc | agg | agg | acc | ctc | aag | cag | gcc | ttt | gct | 4916 |
|---|---|---|---|---|---|---|---|---|---|---|---|---|---|---|---|
| Val | Thr | Tyr | Gln | Ile | Ile | Arg | Arg | Thr | Leu | Lys | Gln | Ala | Phe | Ala | |
| 1380 | | | | | 1385 | | | | | 1390 | | | | | |

| | | | | | | | | | | | | |
|---|---|---|---|---|---|---|---|---|---|---|---|---|
| gac | tgc | aca | gtc | atc | ctg | tgt | gag | cac | agg | att | gag | gcc | atg | ctg | 4961 |
| Asp | Cys | Thr | Val | Ile | Leu | Cys | Glu | His | Arg | Ile | Glu | Ala | Met | Leu | |
| | 1395 | | | | 1400 | | | | | 1405 | | | | | |
| gag | tgc | cag | cag | ttc | ctg | gtg | att | gag | gag | aac | aaa | gtg | agg | cag | 5006 |
| Glu | Cys | Gln | Gln | Phe | Leu | Val | Ile | Glu | Glu | Asn | Lys | Val | Arg | Gln | |
| 1410 | | | | | 1415 | | | | | 1420 | | | | | |
| tat | gac | agc | atc | cag | aag | ctg | ctg | aat | gag | agg | agc | ctg | ttc | agg | 5051 |
| Tyr | Asp | Ser | Ile | Gln | Lys | Leu | Leu | Asn | Glu | Arg | Ser | Leu | Phe | Arg | |
| 1425 | | | | | 1430 | | | | | 1435 | | | | | |
| cag | gcc | atc | agc | ccc | tct | gat | aga | gtg | aag | ctg | ttc | ccc | cac | agg | 5096 |
| Gln | Ala | Ile | Ser | Pro | Ser | Asp | Arg | Val | Lys | Leu | Phe | Pro | His | Arg | |
| 1440 | | | | | 1445 | | | | | 1450 | | | | | |
| aac | agc | tcc | aag | tgc | aag | agc | aag | ccc | cag | att | gct | gcc | ctg | aag | 5141 |
| Asn | Ser | Ser | Lys | Cys | Lys | Ser | Lys | Pro | Gln | Ile | Ala | Ala | Leu | Lys | |
| 1455 | | | | | 1460 | | | | | 1465 | | | | | |
| gag | gag | aca | gag | gag | gaa | gtg | cag | gac | acc | agg | ctg | tga | gggcctgtg | | 5190 |
| Glu | Glu | Thr | Glu | Glu | Glu | Val | Gln | Asp | Thr | Arg | Leu | | | | |
| 1470 | | | | | 1475 | | | | | 1480 | | | | | |

```
ccttctagtt gccagccatc tgttgtttgc cctcccctg tgccttcctt gaccctggaa    5250
ggtgccactc ccactgtcct ttcctaataa aatgaggaaa ttgcattgca ttgtctgagt    5310
aggtgtcatt ctattctggg gggtggggtg gggcaggaca gcaaggggga ggattgggaa    5370
gacaatagca ggcatgcaga tcagcagttc aacctgttga tagtatgtac taagctctca    5430
tgtttaatgt actaagctct catgtttaat gaactaaacc ctcatggcta atgtactaag    5490
ctctcatggc taatgtacta agctctcatg tttcatgtac taagctctca tgtttgaaca    5550
ataaaattaa tataaatcag caacttaaat agcctctaag gttttaagtt ttataagaaa    5610
aaaaagaata tataaggctt ttaaaggttt taaggtttcc taggttatcc tggtacctta    5670
gaaaaactca tccagcatca aatgaaactg caatttattc atatcaggat tatcaatacc    5730
atattttga aaaagtcttt tctgtaatga aggagaaaac tcacccaggc agttccatag    5790
gatggcaaga tcctggtatc tgtctgcaat tccaactctt ccaacatcaa tacaacctat    5850
taatttcccc tcatcaaaaa taaggttatc aagtgagaaa tcaccatgag tgaccactga    5910
atctggtgag aatggcaaaa gcttatgcat ttctttccag acttgttcaa caggccagcc    5970
atttctctca tcatcaaaat cactggcatc aaccaaacca ttattcattc ttgattgggc    6030
ctgagccagt ctaaatactc tatcagagtt aaaaggacaa ttacaaacag gaatggaatg    6090
caatcttctc aggaacactg ccagggcatc aacaatattt tcacctgaat caggatattc    6150
ttctaatacc tggaatgctg tttttccctgg gatggcagtg gtgagtaacc atgcatcatc    6210
aggagttctg ataaaatgct tgatggttgg aagaggcata aattcagtca gccagtttag    6270
tctgaccatc tcatctgtaa catcattggc aacagaacct ttgccatgtt tcagaaacaa    6330
ctctggggca tctggcttcc catacaatct atagattgtg gcacctgatt gcccaacatt    6390
atctctagcc catttatacc catataaatc agcatccatg ttggaattta atcttggcct    6450
ggagcaagag gtttctcttt gaatatggct catggatccc ctcctatagt gagttgtatt    6510
atactatgca gatatactat gccaatgttt aattgtcaa                           6549
```

<210> SEQ ID NO 3
<211> LENGTH: 1480
<212> TYPE: PRT
<213> ORGANISM: Artificial sequence
<220> FEATURE:
<223> OTHER INFORMATION: Synthetic Construct

<400> SEQUENCE: 3

```
Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
                100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
            275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
    355                 360                 365

Asn Lys Ile Gln Asp Phe Leu Gln Lys Gln Glu Tyr Lys Thr Leu Glu
370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415
```

-continued

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
            485                 490                 495

Ile Met Pro Gly Thr Ile Lys Glu Asn Ile Ile Phe Gly Val Ser Tyr
        500                 505                 510

Asp Glu Tyr Arg Tyr Arg Ser Val Ile Lys Ala Cys Gln Leu Glu Glu
    515                 520                 525

Asp Ile Ser Lys Phe Ala Glu Lys Asp Asn Ile Val Leu Gly Glu Gly
530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
            565                 570                 575

Tyr Leu Asp Val Leu Thr Glu Lys Glu Ile Phe Glu Ser Cys Val Cys
        580                 585                 590

Lys Leu Met Ala Asn Lys Thr Arg Ile Leu Val Thr Ser Lys Met Glu
    595                 600                 605

His Leu Lys Lys Ala Asp Lys Ile Leu Ile Leu Asn Glu Gly Ser Ser
610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
            645                 650                 655

Arg Arg Asn Ser Ile Leu Thr Glu Thr Leu His Arg Phe Ser Leu Glu
        660                 665                 670

Gly Asp Ala Pro Val Ser Trp Thr Glu Thr Lys Lys Gln Ser Phe Lys
    675                 680                 685

Gln Thr Gly Glu Phe Gly Glu Lys Arg Lys Asn Ser Ile Leu Asn Pro
690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
            725                 730                 735

Ser Leu Val Pro Asp Ser Glu Gln Gly Glu Ala Ile Leu Pro Arg Ile
        740                 745                 750

Ser Val Ile Ser Thr Gly Pro Thr Leu Gln Ala Arg Arg Arg Gln Ser
    755                 760                 765

Val Leu Asn Leu Met Thr His Ser Val Asn Gln Gly Gln Asn Ile His
770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
            805                 810                 815

Gly Leu Glu Ile Ser Glu Glu Ile Asn Glu Glu Asp Leu Lys Glu Cys
        820                 825                 830

Leu Phe Asp Asp Met Glu Ser Ile Pro Ala Val Thr Thr Trp Asn Thr

```
                835                 840                 845
Tyr Leu Arg Tyr Ile Thr Val His Lys Ser Leu Ile Phe Val Leu Ile
    850                 855                 860
Trp Cys Leu Val Ile Phe Leu Ala Glu Val Ala Ala Ser Leu Val Val
865                 870                 875                 880
Leu Trp Leu Leu Gly Asn Thr Pro Leu Gln Asp Lys Gly Asn Ser Thr
                885                 890                 895
His Ser Arg Asn Asn Ser Tyr Ala Val Ile Ile Thr Ser Thr Ser Ser
                900                 905                 910
Tyr Tyr Val Phe Tyr Ile Tyr Val Gly Val Ala Asp Thr Leu Leu Ala
                915                 920                 925
Met Gly Phe Phe Arg Gly Leu Pro Leu Val His Thr Leu Ile Thr Val
    930                 935                 940
Ser Lys Ile Leu His His Lys Met Leu His Ser Val Leu Gln Ala Pro
945                 950                 955                 960
Met Ser Thr Leu Asn Thr Leu Lys Ala Gly Gly Ile Leu Asn Arg Phe
                965                 970                 975
Ser Lys Asp Ile Ala Ile Leu Asp Asp Leu Leu Pro Leu Thr Ile Phe
                980                 985                 990
Asp Phe Ile Gln Leu Leu Leu Ile Val Ile Gly Ala Ile Ala Val Val
                995                1000                1005
Ala Val Leu Gln Pro Tyr Ile Phe Val Ala Thr Val Pro Val Ile
    1010                1015                1020
Val Ala Phe Ile Met Leu Arg Ala Tyr Phe Leu Gln Thr Ser Gln
    1025                1030                1035
Gln Leu Lys Gln Leu Glu Ser Glu Gly Arg Ser Pro Ile Phe Thr
    1040                1045                1050
His Leu Val Thr Ser Leu Lys Gly Leu Trp Thr Leu Arg Ala Phe
    1055                1060                1065
Gly Arg Gln Pro Tyr Phe Glu Thr Leu Phe His Lys Ala Leu Asn
    1070                1075                1080
Leu His Thr Ala Asn Trp Phe Leu Tyr Leu Ser Thr Leu Arg Trp
    1085                1090                1095
Phe Gln Met Arg Ile Glu Met Ile Phe Val Ile Phe Phe Ile Ala
    1100                1105                1110
Val Thr Phe Ile Ser Ile Leu Thr Thr Gly Glu Gly Glu Gly Arg
    1115                1120                1125
Val Gly Ile Ile Leu Thr Leu Ala Met Asn Ile Met Ser Thr Leu
    1130                1135                1140
Gln Trp Ala Val Asn Ser Ser Ile Asp Val Asp Ser Leu Met Arg
    1145                1150                1155
Ser Val Ser Arg Val Phe Lys Phe Ile Asp Met Pro Thr Glu Gly
    1160                1165                1170
Lys Pro Thr Lys Ser Thr Lys Pro Tyr Lys Asn Gly Gln Leu Ser
    1175                1180                1185
Lys Val Met Ile Ile Glu Asn Ser His Val Lys Lys Asp Asp Ile
    1190                1195                1200
Trp Pro Ser Gly Gly Gln Met Thr Val Lys Asp Leu Thr Ala Lys
    1205                1210                1215
Tyr Thr Glu Gly Gly Asn Ala Ile Leu Glu Asn Ile Ser Phe Ser
    1220                1225                1230
Ile Ser Pro Gly Gln Arg Val Gly Leu Leu Gly Arg Thr Gly Ser
    1235                1240                1245
```

Gly Lys Ser Thr Leu Leu Ser Ala Phe Leu Arg Leu Leu Asn Thr
1250                1255                1260

Glu Gly Glu Ile Gln Ile Asp Gly Val Ser Trp Asp Ser Ile Thr
1265                1270                1275

Leu Gln Gln Trp Arg Lys Ala Phe Gly Val Ile Pro Gln Lys Val
1280                1285                1290

Phe Ile Phe Ser Gly Thr Phe Arg Lys Asn Leu Asp Pro Tyr Glu
1295                1300                1305

Gln Trp Ser Asp Gln Glu Ile Trp Lys Val Ala Asp Glu Val Gly
1310                1315                1320

Leu Arg Ser Val Ile Glu Gln Phe Pro Gly Lys Leu Asp Phe Val
1325                1330                1335

Leu Val Asp Gly Gly Cys Val Leu Ser His Gly His Lys Gln Leu
1340                1345                1350

Met Cys Leu Ala Arg Ser Val Leu Ser Lys Ala Lys Ile Leu Leu
1355                1360                1365

Leu Asp Glu Pro Ser Ala His Leu Asp Pro Val Thr Tyr Gln Ile
1370                1375                1380

Ile Arg Arg Thr Leu Lys Gln Ala Phe Ala Asp Cys Thr Val Ile
1385                1390                1395

Leu Cys Glu His Arg Ile Glu Ala Met Leu Glu Cys Gln Gln Phe
1400                1405                1410

Leu Val Ile Glu Glu Asn Lys Val Arg Gln Tyr Asp Ser Ile Gln
1415                1420                1425

Lys Leu Leu Asn Glu Arg Ser Leu Phe Arg Gln Ala Ile Ser Pro
1430                1435                1440

Ser Asp Arg Val Lys Leu Phe Pro His Arg Asn Ser Ser Lys Cys
1445                1450                1455

Lys Ser Lys Pro Gln Ile Ala Ala Leu Lys Glu Glu Thr Glu Glu
1460                1465                1470

Glu Val Gln Asp Thr Arg Leu
1475                1480

```
<210> SEQ ID NO 4
<211> LENGTH: 3759
<212> TYPE: DNA
<213> ORGANISM: artificial sequence
<220> FEATURE:
<223> OTHER INFORMATION: pGM144 plasmid construct
<220> FEATURE:
<221> NAME/KEY: misc_feature
<222> LOCATION: (1)..(6)
<223> OTHER INFORMATION: Bgl II restriction site
<220> FEATURE:
<221> NAME/KEY: enhancer
<222> LOCATION: (7)..(308)
<223> OTHER INFORMATION: human CMV enhancer
<220> FEATURE:
<221> NAME/KEY: misc_feature
<222> LOCATION: (309)..(314)
<223> OTHER INFORMATION: EcoRI restriction site
<220> FEATURE:
<221> NAME/KEY: promoter
<222> LOCATION: (315)..(538)
<223> OTHER INFORMATION: Human elongation factor 1 alpha promoter
<220> FEATURE:
<221> NAME/KEY: misc_feature
<222> LOCATION: (329)..(334)
<223> OTHER INFORMATION: Sph I restriction site
<220> FEATURE:
<221> NAME/KEY: misc_feature
<222> LOCATION: (539)..(569)
```

```
<223> OTHER INFORMATION: Exon
<220> FEATURE:
<221> NAME/KEY: misc_feature
<222> LOCATION: (570)..(709)
<223> OTHER INFORMATION: Intron
<220> FEATURE:
<221> NAME/KEY: misc_feature
<222> LOCATION: (710)..(727)
<223> OTHER INFORMATION: Exon
<220> FEATURE:
<221> NAME/KEY: misc_feature
<222> LOCATION: (728)..(733)
<223> OTHER INFORMATION: NheI restriction site
<220> FEATURE:
<221> NAME/KEY: misc_feature
<222> LOCATION: (733)..(737)
<223> OTHER INFORMATION: Kozak sequence
<220> FEATURE:
<221> NAME/KEY: CDS
<222> LOCATION: (738)..(2390)
<223> OTHER INFORMATION: Luciferase reporter gene
<220> FEATURE:
<221> NAME/KEY: misc_feature
<222> LOCATION: (2391)..(2396)
<223> OTHER INFORMATION: Apa I restriction enzyme site
<220> FEATURE:
<221> NAME/KEY: polyA_signal
<222> LOCATION: (2396)..(2597)
<223> OTHER INFORMATION: Bovine growth hormone gene polyadenylation
      sequence
<220> FEATURE:
<221> NAME/KEY: misc_feature
<222> LOCATION: (2592)..(2597)
<223> OTHER INFORMATION: Sph I restriction enzyme site within poly A
<220> FEATURE:
<221> NAME/KEY: misc_feature
<222> LOCATION: (2598)..(2598)
<223> OTHER INFORMATION: A included to avoid cpg dinucleotide
<220> FEATURE:
<221> NAME/KEY: rep_origin
<222> LOCATION: (2599)..(2870)
<223> OTHER INFORMATION: R6K origin of replication
<220> FEATURE:
<221> NAME/KEY: misc_feature
<222> LOCATION: (2871)..(2871)
<223> OTHER INFORMATION: A incuded to avoid cpg dinculeotide
<220> FEATURE:
<221> NAME/KEY: misc_feature
<222> LOCATION: (2872)..(2877)
<223> OTHER INFORMATION: KpnI restriction site
<220> FEATURE:
<221> NAME/KEY: misc_feature
<222> LOCATION: (2878)..(3693)
<223> OTHER INFORMATION: Kanamycin resistance marker
<220> FEATURE:
<221> NAME/KEY: misc_feature
<222> LOCATION: (3694)..(3699)
<223> OTHER INFORMATION: BamHI restriction site
<220> FEATURE:
<221> NAME/KEY: misc_feature
<222> LOCATION: (3700)..(3705)
<223> OTHER INFORMATION: Shine Delgarno ribosome binding sequence
<220> FEATURE:
<221> NAME/KEY: promoter
<222> LOCATION: (3706)..(3759)
<223> OTHER INFORMATION: EM7 bacterial promoter

<400> SEQUENCE: 4
agatctgtta cataacttat ggtaaatggc ctgcctggct gactgcccaa tgacccctgc      60
ccaatgatgt caataatgat gtatgttccc atgtaatgcc aatagggact ttccattgat     120
gtcaatgggt ggagtattta tggtaactgc ccacttggca gtacatcaag tgtatcatat     180
gccaagtatg ccccctattg atgtcaatga tggtaaatgg cctgcctggc attatgccca     240
gtacatgacc ttatgggact ttcctacttg gcagtacatc tatgtattag tcattgctat     300
```

-continued

```
taccatggga attcactagt ggagaagagc atgcttgagg gctgagtgcc cctcagtggg      360
cagagagcac atggcccaca gtccctgaga agttgggggg aggggtgggc aattgaactg      420
gtgcctagag aaggtggggc ttgggtaaac tgggaaagtg atgtggtgta ctggctccac      480 cttttcccc agggtggggg agaaccatat ataagtgcag tagtctctgt gaacattcaa       540
gcttctgcct tctccctcct gtgagtttgg taagtcactg actgtctatg cctgggaaag      600
ggtgggcagg agatgggca gtgcaggaaa agtggcacta tgaaccctgc agccctagga       660
atgcatctag acaattgtac taaccttctt ctctttcctc tcctgacagg ttggtgtaca      720
gtagcttgct agccacc atg gag gat gct aag aac atc aag aag ggg cct        770
                   Met Glu Asp Ala Lys Asn Ile Lys Lys Gly Pro
                    1               5                  10 gcc ccc ttc tac ccc ctg gag gat ggc aca gct ggg gag cag ctg cac       818
Ala Pro Phe Tyr Pro Leu Glu Asp Gly Thr Ala Gly Glu Gln Leu His
         15                  20                  25 aag gct atg aag aga tat gcc ctg gtg cct ggc act att gcc ttc aca       866
Lys Ala Met Lys Arg Tyr Ala Leu Val Pro Gly Thr Ile Ala Phe Thr
     30                  35                  40 gat gct cac att gaa gtg gac atc acc tat gct gag tac ttt gag atg       914
Asp Ala His Ile Glu Val Asp Ile Thr Tyr Ala Glu Tyr Phe Glu Met
 45                  50                  55 tca gtg agg ctg gct gag gct atg aaa aga tat ggg ctg aac act aat       962
Ser Val Arg Leu Ala Glu Ala Met Lys Arg Tyr Gly Leu Asn Thr Asn
60                  65                  70                  75 cac agg att gtg gtg tgt tca gag aac tca ctg cag ttc ttc atg cct      1010
His Arg Ile Val Val Cys Ser Glu Asn Ser Leu Gln Phe Phe Met Pro
                 80                  85                  90 gtg ctg gga gcc ctg ttc att gga gtg gct gtg gcc cct gct aat gac      1058
Val Leu Gly Ala Leu Phe Ile Gly Val Ala Val Ala Pro Ala Asn Asp
         95                  100                 105 atc tac aat gag agg gag ctg ctg aac tct atg ggc atc agt cag cct      1106
Ile Tyr Asn Glu Arg Glu Leu Leu Asn Ser Met Gly Ile Ser Gln Pro
     110                 115                 120 aca gtg gtg ttt gtg tct aag aag ggc ctg cag aaa atc ctg aat gtg      1154
Thr Val Val Phe Val Ser Lys Lys Gly Leu Gln Lys Ile Leu Asn Val
125                 130                 135 cag aag aag ctg cct atc att cag aaa atc atc atc atg gac tct aag      1202
Gln Lys Lys Leu Pro Ile Ile Gln Lys Ile Ile Ile Met Asp Ser Lys
140                 145                 150                 155 aca gac tat cag ggc ttt cag tct atg tac acc ttt gtg act agt cac      1250
Thr Asp Tyr Gln Gly Phe Gln Ser Met Tyr Thr Phe Val Thr Ser His
                 160                 165                 170 ctg ccc cct ggc ttc aat gag tat gac ttt gtg cct gag tca ttt gac      1298
Leu Pro Pro Gly Phe Asn Glu Tyr Asp Phe Val Pro Glu Ser Phe Asp
         175                 180                 185 agg gac aag act att gcc ctg atc atg aac tca tca ggc tct aca ggc      1346
Arg Asp Lys Thr Ile Ala Leu Ile Met Asn Ser Ser Gly Ser Thr Gly
     190                 195                 200 ctg cct aag gga gtg gcc ctg cct cac agg aca gcc tgt gtg aga ttc      1394
Leu Pro Lys Gly Val Ala Leu Pro His Arg Thr Ala Cys Val Arg Phe
205                 210                 215 agt cat gct agg gac cct atc ttt ggc aat cag atc atc cct gac aca      1442
Ser His Ala Arg Asp Pro Ile Phe Gly Asn Gln Ile Ile Pro Asp Thr
220                 225                 230                 235 gct atc ctg tca gtg gtg ccc ttt cat cat ggc ttt ggc atg ttc act      1490
Ala Ile Leu Ser Val Val Pro Phe His His Gly Phe Gly Met Phe Thr
                 240                 245                 250 acc ctg ggc tac ctg atc tgt ggc ttc aga gtg gtg ctg atg tac aga      1538
Thr Leu Gly Tyr Leu Ile Cys Gly Phe Arg Val Val Leu Met Tyr Arg
```

```
Thr Leu Gly Tyr Leu Ile Cys Gly Phe Arg Val Val Leu Met Tyr Arg
            255                 260                 265 ttt gag gag gag ctg ttc ctg aga tca ctg cag gac tac aaa att cag    1586
Phe Glu Glu Glu Leu Phe Leu Arg Ser Leu Gln Asp Tyr Lys Ile Gln
        270                 275                 280 tca gcc ctg ctg gtg cct acc ctg ttc agc ttc ttt gct aag tct acc    1634
Ser Ala Leu Leu Val Pro Thr Leu Phe Ser Phe Phe Ala Lys Ser Thr
    285                 290                 295 ctg att gac aag tat gac ctg tct aac ctg cat gag att gcc tca ggg    1682
Leu Ile Asp Lys Tyr Asp Leu Ser Asn Leu His Glu Ile Ala Ser Gly
300                 305                 310                 315 gga gcc ccc ctg tct aag gaa gtg ggg gaa gct gtg gct aag aga ttt    1730
Gly Ala Pro Leu Ser Lys Glu Val Gly Glu Ala Val Ala Lys Arg Phe
                320                 325                 330 cac ctg cct ggc atc agg cag ggc tat ggc ctg aca gag act acc tca    1778
His Leu Pro Gly Ile Arg Gln Gly Tyr Gly Leu Thr Glu Thr Thr Ser
            335                 340                 345 gct att ctg atc acc cct gag ggg gat gac aag cct ggg gct gtg ggc    1826
Ala Ile Leu Ile Thr Pro Glu Gly Asp Asp Lys Pro Gly Ala Val Gly
        350                 355                 360 aaa gtg gtg cct ttc ttt gag gct aaa gtg gtg gac ctg gac aca ggc    1874
Lys Val Val Pro Phe Phe Glu Ala Lys Val Val Asp Leu Asp Thr Gly
    365                 370                 375 aag acc ctg gga gtg aat cag agg ggg gag ctg tgt gtg aga ggc cct    1922
Lys Thr Leu Gly Val Asn Gln Arg Gly Glu Leu Cys Val Arg Gly Pro
380                 385                 390                 395 atg atc atg tca ggc tat gtg aac aac cct gag gct act aat gcc ctg    1970
Met Ile Met Ser Gly Tyr Val Asn Asn Pro Glu Ala Thr Asn Ala Leu
                400                 405                 410 att gat aag gat ggc tgg ctg cac tca ggg gac att gcc tac tgg gat    2018
Ile Asp Lys Asp Gly Trp Leu His Ser Gly Asp Ile Ala Tyr Trp Asp
            415                 420                 425 gag gat gag cac ttc ttc att gtg gac agg ctg aag tca ctc atc aag    2066
Glu Asp Glu His Phe Phe Ile Val Asp Arg Leu Lys Ser Leu Ile Lys
        430                 435                 440 tac aag ggc tat caa gtg gcc cca gct gag tta gag tca atc tta ctt    2114
Tyr Lys Gly Tyr Gln Val Ala Pro Ala Glu Leu Glu Ser Ile Leu Leu
    445                 450                 455 cag cac cct aac atc ttt gat gct gga gtg gca ggt tta cct gat gat    2162
Gln His Pro Asn Ile Phe Asp Ala Gly Val Ala Gly Leu Pro Asp Asp
460                 465                 470                 475 gat gct ggg gag tta cct gct gct gtg gtg gta tta gag cat ggc aag    2210
Asp Ala Gly Glu Leu Pro Ala Ala Val Val Val Leu Glu His Gly Lys
                480                 485                 490 act atg aca gag aaa gag att gtg gat tat gtg gct agt caa gtc act    2258
Thr Met Thr Glu Lys Glu Ile Val Asp Tyr Val Ala Ser Gln Val Thr
            495                 500                 505 aca gct aag aag ctc agg ggg gga gtg gtc ttt gtg gat gaa gtg cct    2306
Thr Ala Lys Lys Leu Arg Gly Gly Val Val Phe Val Asp Glu Val Pro
        510                 515                 520 aag ggc ctc aca ggc aag tta gat gct agg aag atc agg gag atc ctc    2354
Lys Gly Leu Thr Gly Lys Leu Asp Ala Arg Lys Ile Arg Glu Ile Leu
    525                 530                 535 atc aag gct aag aag ggg ggc aag att gct gtt taa gggccctgtg         2400
Ile Lys Ala Lys Lys Gly Gly Lys Ile Ala Val
540                 545                 550 ccttctagtt gccagccatc tgttgtttgc ccctcccctg tgccttcctt gaccctggaa  2460
ggtgccactc ccactgtcct ttcctaataa aatgaggaaa ttgcattgca ttgtctgagt  2520
```

| | |
|---|---|
| aggtgtcatt ctattctggg gggtggggtg gggcaggaca gcaaggggga ggattgggaa | 2580 |
| gacaatagca ggcatgcaga tcagcagttc aacctgttga tagtatgtac taagctctca | 2640 |
| tgtttaatgt actaagctct catgtttaat gaactaaacc ctcatggcta atgtactaag | 2700 |
| ctctcatggc taatgtacta agctctcatg tttcatgtac taagctctca tgtttgaaca | 2760 |
| ataaaattaa tataaatcag caacttaaat agcctctaag gttttaagtt ttataagaaa | 2820 |
| aaaaagaata tataaggctt ttaaaggttt taaggtttcc taggttatcc tggtacctta | 2880 |
| gaaaaactca tccagcatca aatgaaactg caatttattc atatcaggat tatcaatacc | 2940 |
| atattttga aaaagtcttt tctgtaatga aggagaaaac tcacccaggc agttccatag | 3000 |
| gatggcaaga tcctggtatc tgtctgcaat tccaactctt ccaacatcaa tacaacctat | 3060 |
| taattttccccc tcatcaaaaa taaggttatc aagtgagaaa tcaccatgag tgaccactga | 3120 |
| atctggtgag aatggcaaaa gcttatgcat ttctttccag acttgttcaa caggccagcc | 3180 |
| atttctctca tcatcaaaat cactggcatc aaccaaacca ttattcattc ttgattgggc | 3240 |
| ctgagccagt ctaaatactc tatcagagtt aaaaggacaa ttacaaacag gaatggaatg | 3300 |
| caatcttctc aggaacactg ccagggcatc aacaatattt tcacctgaat caggatattc | 3360 |
| ttctaatacc tggaatgctg ttttccctgg gatggcagtg gtgagtaacc atgcatcatc | 3420 |
| aggagttctg ataaaatgct tgatggttgg aagaggcata aattcagtca gccagtttag | 3480 |
| tctgaccatc tcatctgtaa catcattggc aacagaacct tgccatgtt tcagaaacaa | 3540 |
| ctctggggca tctggcttcc catacaatct atagattgtg gcacctgatt gcccaacatt | 3600 |
| atctctagcc catttatacc catataaatc agcatccatg ttggaattta atcttggcct | 3660 |
| ggagcaagag gtttctcttt gaatatggct catggatccc ctcctatagt gagttgtatt | 3720 |
| atactatgca gatatactat gccaatgttt aattgtcaa | 3759 |

<210> SEQ ID NO 5
<211> LENGTH: 550
<212> TYPE: PRT
<213> ORGANISM: artificial sequence
<220> FEATURE:
<223> OTHER INFORMATION: Synthetic Construct

<400> SEQUENCE: 5

Met Glu Asp Ala Lys Asn Ile Lys Gly Pro Ala Pro Phe Tyr Pro
1               5                   10                  15

Leu Glu Asp Gly Thr Ala Gly Glu Gln Leu His Lys Ala Met Lys Arg
                20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

```
Ile Ile Gln Lys Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
            165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
            195                 200                 205

Ala Leu Pro His Arg Thr Ala Cys Val Arg Phe Ser His Ala Arg Asp
            210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
            245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
            275                 280                 285

Pro Thr Leu Phe Ser Phe Phe Ala Lys Ser Thr Leu Ile Asp Lys Tyr
290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
            325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
            355                 360                 365

Phe Glu Ala Lys Val Val Asp Leu Asp Thr Gly Lys Thr Leu Gly Val
370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
            405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
            485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
530                 535                 540

Gly Gly Lys Ile Ala Val
545                 550
```

NUCLEIC ACID CONSTRUCT

This application is a continuation of U.S. Pat. No. 8,871,503, issued Oct. 28, 2014, which is the National Stage of International Application No. PCT/GB2007/001104, published in English under PCT Article 21(2), filed Mar. 28, 2007, which claims priority to United Kingdom Patent Application No. 0606190.7, filed on Mar. 28, 2006, all of which are incorporated by reference in their entirety.

This application includes a Sequence Listing submitted electronically as a text file named 27797_US_CRF_Sequence Listing.txt, created on May 4, 2015, with a size of 60 kb. The sequence listing is hereby incorporated by reference.

FIELD OF THE INVENTION

The present invention relates to constructs. The invention also relates to pharmaceutical compositions comprising the constructs, the use of the constructs in the manufacture of medicaments as well as to the use of the constructs in various methods.

BACKGROUND OF THE INVENTION

A variety of promoters are used in constructs for gene expression. The choice of promoter will often be influenced by the specific use that the construct is being employed for. However, in general constructs that provide high-level expression over a sustained period are desired, particularly for therapeutic applications, but also where it is desired to express genes to harvest the expressed proteins and in instances such as agriculture to obtain desired characteristics in reared animals.

In the use of constructs in a therapeutic context sustained expression at a high level is particularly important. Achieving sustained and high-level expression may mean that a particular treatment has to be given less often and remains effective for longer. In chronic conditions and inherited genetic defects this may be particularly important where in essence the underlying defect means that continuous treatment has to be given. Examples of such conditions include Cystic Fibrosis where treatment may have to be given permanently and hence any means of increasing the interval between treatments is important.

Gene expression constructs can suffer from a variety of problems. In some cases expression may be only for a short period before being silenced. This is particularly the case in vivo and in a variety of tissues. Additionally, or alternatively, some constructs give rise to only very weak expression and inadequate expression to achieve the desired effect.

A further problem with some constructs for gene expression when employed in vivo is that they may trigger the immune system of the subject in an undesired way. Thus, a subject may display an immune response against particular viral gene expression constructs that limit their effectiveness, particularly when used repeatedly in the same subject which may be the situation as outlined above for many conditions.

BRIEF DESCRIPTION OF THE DRAWINGS

FIG. 4b shows the effect of addition of a single CpG dinucleotide to a construct with no CpG dinucleotides. From left to right in each graph, the results for a construct with 317 CpG dinucleotides, a single CpG dinucleotide, no CpG dinucleotides and control untreated mice are shown.

FIG. 8 shows expression levels in the lung with time following GL67 aerosol delivery of the constructs pG2EFIa Lux (employs the EFIa promoter and has 245 CpGs), pG2CEFIa Lux (employs the human CMV enhancer and the EFIa promoter and has 262 CpGs), pG2hCEFI Lux (employs a CpG free hman CMV enhancer and a human EFIa promoter, the construct has 149 CpGs) and pG4hCEFI soLux (employs a CpG free hman CMV enhancer and a human EFIa promoter and the entire construct has no CpGs).

BRIEF DESCRIPTION OF THE SEQUENCES

Figure 1:
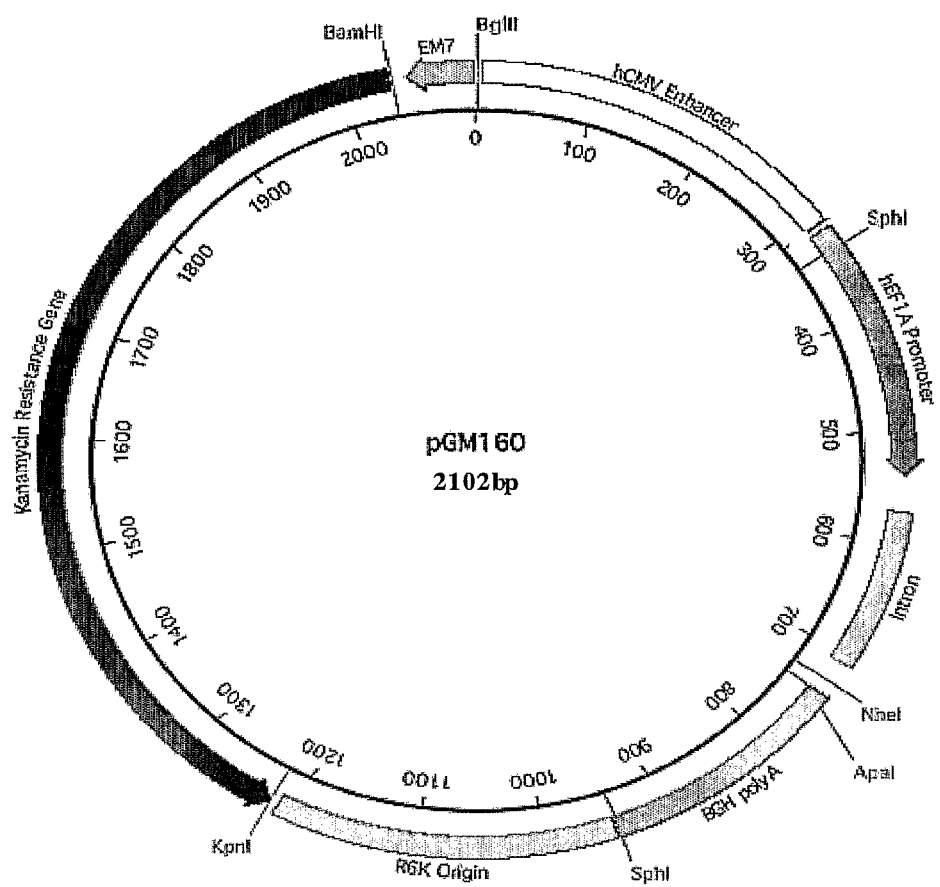
FIG. 1 depicts the structure of the pGM160 construct into which sequences can be cloned for expression from the hCEFI promoter.
Figure 2:
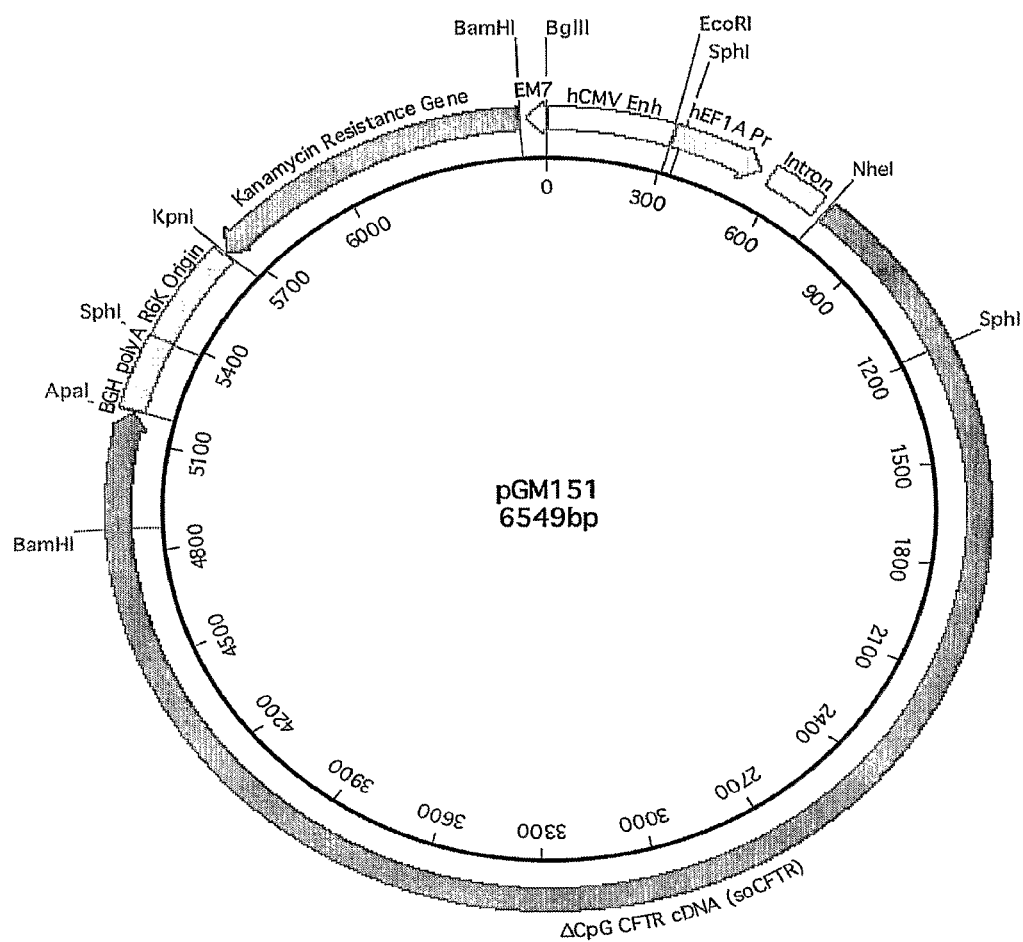
FIG. 2 depicts the structure of the pGM151 construct in which the coding sequences for the CFTR polypeptide are cloned in operable linkage with the hCEFI promoter.
Figure 3:
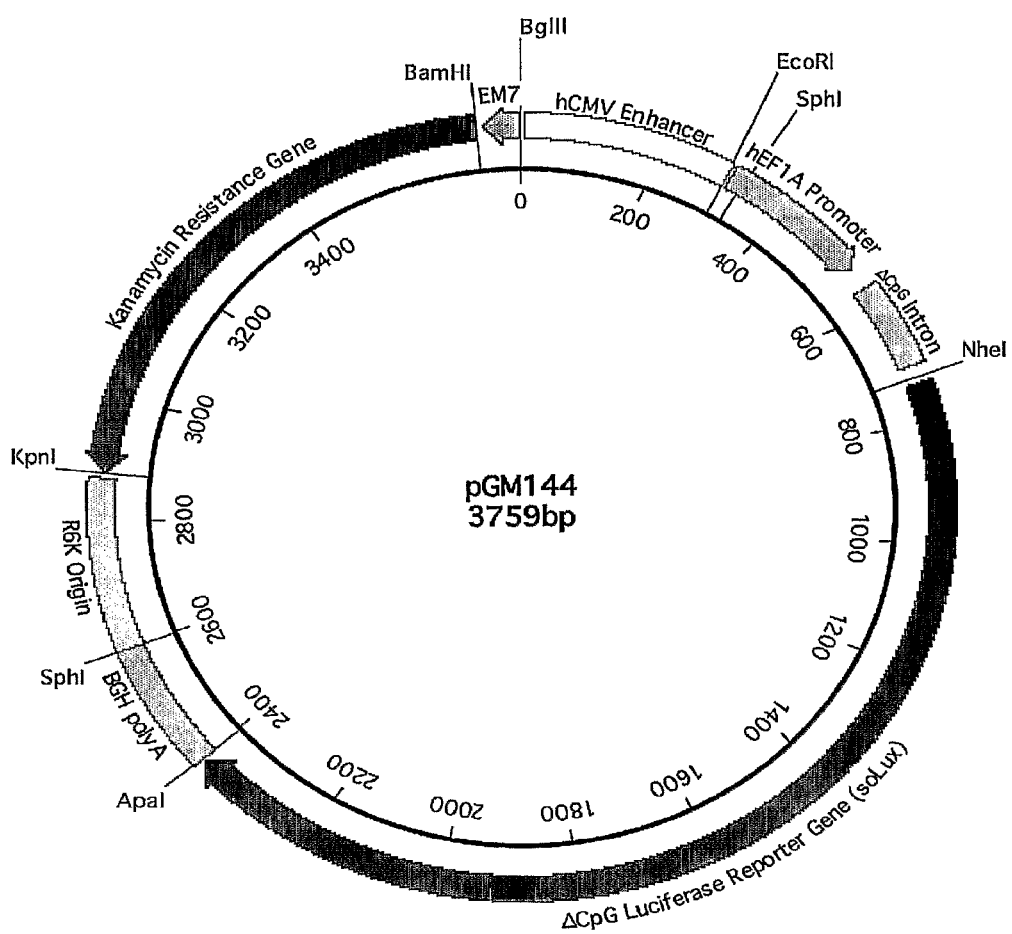
FIG. 3 depicts the structure of the pGM144 construct in which the coding sequences for the luciferase reporter polypeptide are cloned in operable linkage with the hCEFI promoter.

SEQ ID NO: 1 is the polynucleotide sequence of the pGM160 construct for cloning sequences for expression using the hCEFI promoter.

SEQ ID NO: 2 is the polynucleotide sequence of the pGM151 construct which includes the coding sequences for CFTR which contains no CpG dinuculeotides and also which have been codon optimised for expression (soCFTR). The invention also allows for an alternative polynucleotide sequence of CFTR in which nucleotide 2595 is C, nucleotide 3234 is T and nucleotide 3236 is C.

SEQ ID NO: 3 is the polypeptide sequence of the CFTR polypeptide encoded by the pGM151 construct of SEQ ID No: 2. The invention also allows for an alternative polypeptide sequence of CFTR in which amino acid 620 is H (Histidine) and amino acid 833 is F (Phenylalanine).

SEQ ID NO: 4 is the polynucleotide sequence of the pGM144 construct which includes the coding sequences for a luciferase polypeptide, which contains no CpG dinucleotides and also which have codons optimised for expression (soLux).

SEQ ID NO: 5 is the polypeptide sequence of the luciferase polypeptide encoded by the pGM144 construct of SEQ ID No:4.

SUMMARY OF THE INVENTION

The present invention provides hCEFI promoters that comprise a human CMV enhancer operably linked to a human EF1a promoter, functional fragments thereof or functional variants of either. In a particularly preferred instance, the hCEFI promoters have been modified to reduce the number of, or eliminate altogether, CpG dinucleotides.

The hCEFI promoters have been shown to give rise to unexpectedly high and sustained levels of expression. The hCEFI promoter of the invention is therefore particularly useful for constructs for gene expression. Thus, the constructs of the invention are preferably gene expression constructs. The invention also provides constructs that have been further optimised for gene expression, and in particular their therapeutic use, by eliminating or reducing the number of CpG dinucleotides to reduce unwanted immune responses.

Thus, the present invention provides a nucleic acid construct comprising a hCEF1 promoter operably linked to a sequence for expression, where the hCEF1 promoter comprises:
  (i) a human CMV enhancer operably linked to a human EF1a promoter;
  (ii) a functional fragment of (i); or
  (iii) a functional variant of (i) or (ii).

The present invention additionally provides:
  a pharmaceutical composition comprising a construct of the invention and a pharmaceutically acceptable carrier or excipient;
  a construct of the invention for use in a method of treatment of the human or animal body by therapy or surgery; and
  use of a construct of the present invention in the manufacture of a medicament for use in treating a genetic disorder, chronic condition, allergy, autoimmunity, infection or a cancer.

The invention further provides a method of treating a disorder comprising administering a construct of the invention in an effective amount to a subject suffering from such a disorder.

The invention also provides:
  a non-therapeutic method of expressing a sequence in a subject, the method comprising administering a construct of the invention, wherein the hCEFI promoter is operably linked to a non-therapeutic sequence for expression;
  an in vitro or ex vivo method of expressing a gene in a cell, tissue or organ, the method comprising introducing a construct of the invention into said cells, tissue or organ; and
  an isolated hCEFI promoter of the invention.

The invention also provides a construct comprising a hCEFI promoter operably linked to a restriction site, wherein insertion of coding sequences into the restriction site will result in their operable linkage to the hCEFI promoter.

The invention also provides a non-human animal comprising an hCEFI promoter of the invention.

DETAILED DESCRIPTION OF THE INVENTION

Before describing the present invention in detail, it is to be understood that this invention is not limited to particularly exemplified molecules or process parameters as such may, of course, vary. It is also to be understood that the terminology used herein is for the purpose of describing particular embodiments of the invention only, and is not intended to be limiting. In addition, the practice of the present invention will employ, unless otherwise indicated, conventional methods of virology, microbiology, molecular biology, recombinant DNA techniques and immunology all of which are within the ordinary skill of the art. Such techniques are explained fully in the literature. See, e.g., Sambrook, et al., *Molecular Cloning: A Laboratory Manual* (2nd Edition, 1989); *DNA Cloning: A Practical Approach*, vol. I & II (D. Glover, ed.); *Oligonucleotide Synthesis* (N. Gait, ed., 1984); *A Practical Guide to Molecular Cloning* (1984); and *Fundamental Virology*, 2nd Edition, vol. I & II (B. N. Fields and D. M. Knipe, eds.).

All publications, patents and patent applications cited herein, whether supra or infra, are hereby incorporated by reference in their entirety.

It must be noted that, as used in this specification and the appended claims, the singular forms "a," "an" and "the" include plural references unless the content clearly dictates otherwise.

In instances where a particular agent is specified as comprising particular units, in a preferred instance the agent may consist essentially of such units.

General Overview

The invention is concerned in particular with constructs that allow efficient expression of sequences due to the presence of the hCEFI promoter. The constructs provide high levels of expression and importantly sustained expression. This makes the constructs suitable for any application where it is desired to express particular sequences, especially in the expression of sequences to treat disorders, particularly those where sustained gene expression is needed. Due to the length of expression which is seen using the constructs of the invention, it may be that the constructs may be administered less often and/or give rise to improved results where the level of expression with other constructs would be too short lived and/or too low in magnitude.

The constructs are in particular nucleic acid constructs. The terms "nucleic acid molecule" and "polynucleotide" are used interchangeably herein and refer to a polymeric form of nucleotides of any length, either deoxyribonucleotides or ribonucleotides, or analogs thereof. In a particularly preferred instance, the constructs of the invention comprise DNA and preferably are DNA constructs.

The invention provides constructs comprising, or in some embodiments, consisting essentially of a hCEFI promoter sequence and a cloning site, such that when a coding sequence is inserted in the cloning site, the coding sequence is in operable linkage with the promoter. The invention also provides constructs with sequences for expression inserted into the cloning site or sites. The sequences to be expressed may in particular be coding sequences. The coding sequences may encode any of the polypeptides referred to herein.

The constructs of the invention may be employed in a variety of pharmaceutical compositions, vaccines, in the manufacture of medicaments and also in a range of methods.

The hCEFI Promoter

The various constructs of the invention employ the hCEFI promoter. The hCEFI promoter gives rises to prolonged and high-level expression of sequences and comprises:
  (i) a human CMV enhancer operably linked to a human EF1a promoter;
  (ii) a functional fragment of (i); or
  (iii) a functional variant of (i) or (ii).

"Operably linked" refers to an arrangement of elements wherein the components so described are configured so as to perform their usual function. Thus, a promoter operably linked to a nucleic acid sequence is capable of effecting the expression of that sequence when the proper enzymes are present. The hCEFI promoter need not be contiguous with the sequence, so long as it functions to direct the expression thereof. Thus, the sequence to be expressed will be transcribed due to the hCEFI promoter. In a preferred instance any of the components described herein will be in operable linkage when present in a construct of the invention.

In a preferred embodiment, the hCEFI promoter is therefore a composite of a human CMV enhancer linked to a human EF1a promoter, though functional fragments thereof and functional variants thereof may also be employed. It has been unexpectedly found that the use of the human CMV enhancer linked to the human EF1a promoter gives high and in particular sustained expression.

In some embodiments, a human CMV enhancer may be employed in conjunction with a functional fragment or functional variant of a human EF1a promoter. In other embodiments, a functional fragment or functional variant of a human CMV enhancer may be employed with a human EF1a promoter. In other embodiments, a functional fragment or variant of a human CMV enhancer may be employed with a functional fragment or variant of a human EF1a promoter.

The hCEFI promoter is for eukaryotic expression. The hCEFI promoters of the invention are functional in mammalian cells and may be used for expression in mammalian cells. The hCEFI may also be used for expression in avians. Thus, the constructs of the invention will express the sequences for expression operably linked to the hCEFI promoter in eukaryotic cells, in particular mammalian cells and avian cells and preferably in mammalian cells. In a particularly preferred instance, they will be used for expression in human cells.

In one particularly preferred instance the hCEF1 promoter may comprise the sequence of nucleotides 7 to 538 of SEQ ID No: 1, a functional fragment thereof or a functional variant of either. A functional fragment may, for instance, be at least 200, preferably at least 300, even more preferably at least 400 and even more preferably at least 500 nucleotides in length. A functional variant may, for instance, have at least 50%, preferably at least 60%, more preferably at least 70%, even more preferably at least 80% and still more preferably at least 90% sequence identity to nucleotides 7 to 538 of SEQ ID No:1. In a preferred instance, a functional variant may have at least 92%, preferably at least 95%, even more preferably at least 97% and even more preferably at least 99% sequence identity nucleotides 7 to 538 of SEQ ID No:1. Such sequence identity may be over any of the lengths specified herein, for instance over at least 20, preferably at least 50, more preferably at least 100, even more preferably at least 300 and even more preferably over the entire length of the sequence in question.

Any of the length of fragments and levels of sequence identity referred to herein may define the functional fragments and variants. The fragments and variants will be functional. In a preferred embodiment they will give at least 10%, preferably at least 25%, even more preferably at least 50%, still more preferably at least 75%, and yet more preferably at least 90% of the expression of the promoter of nucleotides 7 to 538 of SEQ ID No:1. In some instances, the level of expression may be higher and may be at least double, triple, four times or more that of the expression seen with nucleotides 7 to 538 of SEQ ID No:1. The duration of expression may also, for instance, be any of the levels specified, such as at least 10%, 25%, 50%, 75%, or 90% of that seen with nucleotides 7 to 538 of SEQ ID No:1 or may, for instance, be at least double, triple or four times that seen with nucleotides 7 to 538 of SEQ ID No: 1. In one preferred instance, the level and duration of expression may have any of the preceding magnitudes specified in comparison to expression using the promoter of nucleotides 7 to 538 of SEQ ID No:1.

Functionality of fragments and variants may be assessed in any suitable assay system. In one preferred instance, the same construct is assessed apart from the change in promoter. The promoter under test may, for instance, be a fragment or variant of the original promoter in the construct. In a preferred instance, expression is compared between the construct of SEQ ID No: 2 or 4 and the equivalent construct, but with nucleotides 7 to 538 replaced with the fragment or variant under test. In one instance, the construct under test may comprise the luciferase gene of nucleotides 738 to 2390 of SEQ ID No:4, a functional fragment thereof or a functional variant of either and luciferase expression may be measured to determine functionality. In one embodiment the construct of SEQ ID No:1 is employed, but which has had a sequence for expression and in particular a coding sequence cloned into it, including any of those mentioned herein.

Any appropriate system may be used to assess functionality. An in vitro system may be used including any of the cell types measured herein. In a particularly preferred case, an in vivo system and in particular a non-human animal may be used to assess functionality. Any of the non-human animals and in particular the non-human mammals mentioned herein may be used. Rodents and in particular mice may be employed. Any of the administration routes mentioned herein may be employed in assessing functionality and in a preferred embodiment administration into the lung, particularly via aerosol administration and in particular aerosol administration employing liposomes may be employed and preferably cationic liposomes or cationic polymers may be employed. The liposome formulation may be any of those mentioned herein. In particular, a GL67 liposome formulation may be used. In the case of cationic polymers PEI is a particularly preferred choice for formulation.

In one preferred instance, complexes of a construct of the invention and cationic liposomes or cationic polymers are delivered into the lungs of mice as aerosols and expression measured for at least 7, preferably at least 14, more preferably at least 14, even more preferably at least 21 and still more preferably at least 28 days, yet more preferably at least 56 days. Expression may be measured at, for example, any of those time points, all of those time points and so on. Such durations may be used in any of the ways of assessing functionality discussed herein. Any of the non-human animals and expression routes mentioned herein may be employed in such assessment. In a preferred instance, luciferase expression is measured.

The high and sustained expression seen employing the hCEFI promoter means that the constructs of the invention find a wide range of uses. The high and sustained level of expression was unexpected given that previous prior art constructs existed employing the mouse CMV enhancer and no indication was given that the mouse CMV enhancer would perform anything other than optimally in human cells and give sustained expression. Surprisingly therefore, the human CMV enhancer in tandem with the human EF1a promoter gives far superior and sustained expression in comparison to such prior art constructs.

In a further preferred instance, the hCEFI promoters of the invention have low or no CpG dinucleotide content. The absence of CpG dinucleotides further improves the performance of constructs of the invention and in particular in situations where it is not desired to induce an immune response against an expressed antigen or an inflammatory response against the delivered expression construct. The elimination of CpG dinucleotides reduces the occurrence of flu-like symptoms and inflammation which may result from administration of constructs, particularly when administered to the airways.

The present invention also provides any of the above referred hCEFI promoters in isolated form as well as a nucleic acid comprising the hCEFI promoter. In a preferred instance, the hCEFI promoter is present in a construct of the invention.

Variants, Fragments and Sequence Identity

A number of elements may be employed in the constructs of the invention. Functional fragments and functional variants of specific sequences may be employed in the constructs of the present invention. For instance, the nucleotide sequences of SEQ ID Nos 1 to 5 provide the sequence of various specific elements. However, functional fragments of such specific sequences as well as functional variants of either may be employed. The same applies to any of the elements, polypeptides and other integers referred to herein.

Variants of a specific sequence may be defined by reference to a degree of sequence identity or homology to the specific sequence referred to herein. In some instances, the level of sequence identity may be at least 25%, preferably at least 30%, more preferably at least 50%, even more preferably at least 60% and still more preferably at least 75%. In some instances, the level of sequence identity may be at least 80%, more preferably at least 90%, even more preferably at least 95%, still more preferably at least 97% and in some instances at least 99%. Thus, wherever sequence identity is referred to herein such levels of identity may, for instance, apply.

The length such sequence identity occurs over may, for instance, be over at least 15, preferably at least 30, for instance at least 40, 60 or 100 or more contiguous nucleotides. The region of homology may be over at least 150, preferably at least 200 and even more preferably over at least 300 nucleotides. In some instance, the level of sequence identity may be over at least 25%, more preferably at least 50%, still more preferably at least 75% and even more preferably over at least 95% of the length of the element or construct in question. In a particularly preferred instance, the level of sequence identity is over the entire length of the element or construct in question. In reference to polypeptides the same levels and lengths of sequence identity may, for instance, be present.

Methods of measuring polynucleotide and polypeptide homology or identity are known in the art. For example the UWGCG Package provides the BESTFIT program which can be used to calculate homology (e.g. used on its default settings) (Devereux et al (1984) Nucleic Acids Research 12, p 387-395).

The PILEUP and BLAST algorithms can also be used to calculate homology or line up sequences (typically on their default settings), for example as described in Altschul S. F. (1993) J Mol Evol 36:290-300; Altschul, S, F et al (1990) J Mol Biol 215:403-10.

Software for performing BLAST analysis is publicly available through the National Centre for Biotechnology Information (www.ncbi.nlm.nih.gov). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89:10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl, Acad. Sci. USA 90:5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

In some instances, a variant may differ from a specific sequence by 100 or less, 50 or less, 20 or less, 15 or less, 10 or less, 5 or less, 3 or less or 2 or less changes (each of which may be a substitution, duplication, deletion or insertion) or by more than such numbers of changes. In some instances there may be only a single change. These mutations may be measured over a region of at least 30, for instance at least 40, 60 or 100 or more contiguous nucleotides of the elements in question and in particular over their entire length. Similar levels of changes may be present in polypeptide sequences. In a preferred instance, the variation in question will not introduce CpG dinucleotides into the nucleotide sequences in question.

Where a polynucleotide encodes a polypeptide, substitutions may preferably create "conservative" changes in the amino acid encoded. These are defined according to Table 1 below. Amino acids in the same block in the second column and preferably in the same line in the third column may be substituted for each other in conservative changes.

TABLE 1

| | | |
|---|---|---|
| ALIPHATIC | Non-Polar | G A P |
| | | I L V |
| | Polar-uncharged | C S T M |
| | | N Q |
| | Polar-charged | D E |
| | | K R |
| AROMATIC | | H F W Y |

In some instances, functional fragments of particular integers referred to herein may be employed. The term "fragment" indicates a smaller part of a larger entity. Fragments of specific elements referred to herein may be employed in the invention. In particular, such fragments will retain some or all functionality of the original element and in particular any of the functions mentioned herein. They may retain any of the levels of functionality referred to herein.

In some instances, a fragment may be at least 50%, preferably at least 60%, more preferably at least 70%, still more preferably at least 80%, even more preferably at least 90% and still more preferably at least 95% of the length of the original. A fragment may be equal to or less than such percentages of the length of the original. In the present invention variants of functional fragments may be employed.

Variants and fragments of particular sequences will be functional that is they will retain at least a degree of a particular function possessed by the sequence they are derived from. Thus, in the case of promoters they will be able to give rise to transcription and in particular will show at least a proportion of the expression levels and duration shown by the original promoter. Variants and fragments similarly may retain any one or more of the other functions mentioned herein which the original molecule possessed to some extent.

Constructs

In a preferred instance, the hCEFI promoters of the present invention are utilised in constructs. Thus, in one embodiment, the present invention provides a nucleic acid construct comprising a hCEFI promoter operably linked to a sequence for expression, where the hCEFI promoter comprises:
 (i) a human CMV enhancer operably linked to a human EF1a promoter;
 (ii) a functional fragment of (i); or
 (iii) a functional variant of (i) or (ii).

The constructs can be used to give rise to expression of the sequence operably linked to the hCEFI promoter. The sequence for expression may in a preferred case comprise a coding sequence for translation into a polypeptide. In other instances, the sequence for expression may be transcribed to give rise to a functional RNA molecule, or the transcript may be processed to give rise to a functional RNA molecule.

In instances where the specific construct of SEQ ID No:1 are referred to, the equivalent elements of the constructs of SEQ ID Nos:2 and 4 may be employed as may functional variants and fragments of such sequences.

In one particularly preferred embodiment, the construct of the invention may include an intron or introns. Thus, for instance, in constructs where the sequence to be expressed comprises coding sequences, in a preferred instance, an initial exon may be present upstream of the exon or exons comprising the coding sequences and then an intron may be present between the two.

The invention therefore provides, in one instance, constructs comprising an intron between the hCEFI promoter and coding sequences to be expressed. The intron will be operably linked to the hCEFI promoter, the initial exon or exons and the exon or exons comprising the coding sequences to be expressed. The intron will therefore be operably linked to the other sequences it is transcribed with so that it is spliced out of the transcript.

The construct may therefore also include the appropriate splice donor and splice acceptor sequences to allow for splicing out of any intron included. Introns may also be present interspersed with the exons comprising the coding sequences and then be spliced out for translation or in some instances there may be no such introns.

Any suitable introns may be employed and in particular any intron comprising the levels of CpG dinucleotides or lacking such dinucleotides as specified herein may, for instance, be employed. The exons may also preferably contain such levels of CpG dinucleotides and in a particularly preferred instance lack any CpG dinucleotides.

In one preferred instance, a construct of the invention will comprise:
 (i) the intron of nucleotides 570 to 709 of SEQ ID No:1;
 (ii) a functional fragment of (i); or
 (iii) a functional variant of (i) or (ii).

In a preferred instance, any of the constructs of the invention may comprise such an intron. The functional variant or fragment may have any of the levels of sequence identity and length specified herein or indeed other characterics. The intron will be functional in that it will be spliced out of the resulting transcript produced from the hCEFI promoter in the construct. A variant, for instance, may have at least 40%, preferably at least 50%, even more preferably at least 60% and more preferably at least 75% sequence identity to nucleotides 570 to 709 of SEQ ID No:1. In some instances, the level of sequence identity may be at least 80%, preferably at least 90% and even more, preferably at least 95%. The functional variant or fragment may, for instance, be at least 50, preferably at least 75 and even more preferably at least 100 nucleotides in length.

In a further preferred embodiment, a construct of the invention will comprise an exon operably linked to the hCEFI promoter and the coding sequences to be expressed with an intervening intron which will be spliced from the construct. One or more such exons may be present and in particular such exons will typically be upstream of the kozak sequence, i.e. 5' of it.

In a preferred instance a construct of the invention may comprise an exon which comprises:
 (i) the sequence of nucleotides 539 to 569 of SEQ ID No:1;
 (ii) a functional fragment of (i); or
 (iii) a functional variant of (i) or (ii).

Any of the levels of characteristics, and in particular level of sequence identity and length of fragment specified herein, may define the exon. A fragment or variant, may, for instance be at least 10 nucleotides, preferably at least 15 and even more preferably at least 20 nucleotides in length or may be 30 nucleotides in length. In addition, the exon or exons preferably have any of the levels of CpG dinucleotides specified herein and in particular no CpG dinucleotides.

In one instance, the one of the above exons may also include the start of the coding sequence to be expressed. In a preferred instance there is at least one non-coding exon and an intron before the exon or exons making up the coding sequence.

In another preferred instance, an exon may be present which comprises:
  (i) the sequence of nucleotides 710 to 727 of SEQ ID No:1;
  (ii) a functional fragment of (i); or
  (iii) a functional variant of (i) or (ii).

Any of the levels of characteristics, and in particular level of sequence identity and length of fragment, may define the exon. A fragment or variant, may, for instance be at least 5 nucleotides, preferably at least 10 and even more preferably at least 12 nucleotides in length or may be 17 nucleotides in length.

In a particularly preferred instance, a construct of the invention may comprise a combination of such exons and an intron, particularly prior to the exon or exons comprising the coding sequences. Thus, in a preferred instance of the invention a construct may comprise:
  (i) the nucleotide sequence of nucleotides 539 to 727 of SEQ ID No:1;
  (ii) a functional fragment of (i); or
  (iii) a functional variant of (i) or (ii).

The functional fragments and variants may have any of the features specified herein and in particular level of sequence identity and length specified. For instance, a variant may have at least 40%, preferably at least 50%, even more preferably at least 60% and more preferably at least 75% sequence identity to nucleotides 539 to 727 of SEQ ID No:1. In some instances, the level of sequence identity may be at least 80%, preferably at least 90% and even more preferably at least 95%. The functional variant or fragment may, for instance, be at least 75, preferably at least 100 and even more preferably at least 150 nucleotides in length. A functional fragment or variant will preferably include an intron which is appropriately spliced out. Splicing events should result in the generation of a transcript capable of expressing the desired polypeptide. In one embodiment a construct of the invention comprises such exons and introns and a restriction site so that a chosen sequence can be inserted into the construct in operable linkage with them.

In situations where the sequence to be expressed comprises a coding sequence for expression it will preferably be operably linked to the necessary elements for translation of the coding sequences. Typically, a kozak sequence and a polyadenylation signal may be operably linked to the coding sequence. Any appropriate Kozak and polyadenylation sequences may be employed. In a preferred instance:
  (i) the kozak sequence may comprise nucleotides 733 to 737 of SEQ ID No:2 or 4, a functional fragment thereof, or a functional variant of either; and/or
  (ii) the polyadenylation sequence may comprise nucleotides 2396 to 2597 of SEQ ID No: 4, a functional fragment thereof, or a functional variant of either.

The length and level of sequence identity of the fragment and variant may be any of those specified herein. In the case of the polyadenylation sequences, for instance, the fragment may be at least 50, preferably at least 100 and even more preferably at least 150 nucleotides in length. The level of sequence identity for the kozak sequence and/or the polyadenylation sequence may be at least 50%, preferably at least 60%, more preferably at least 70%, even more preferably at least 80% and still more preferably at least 90% or even any of the higher levels of sequence identity specified herein.

Functionality may be measured by any appropriate assay including any of those mentioned herein and the level of functionality may be any of those mentioned herein. In the case of the Kozak sequence, for instance, the level of translation may be at least 10%, preferably at least 25%, more preferably at least 50%, even more preferably at least 75%, and still more preferably at least 90% of the level seen with the original sequence. In the case of the polyadenylation sequence, the level of polyadenylation and/or translation may, for instance, be any such levels. Functionality may also be measured in the level of overall expression and/or the duration of expression seen. In some case, the variant or fragment may give rise to a higher level of functionality than the original sequence for any of the parameters measured, such as, for instance, at least double, triple, quadruple or more.

The constructs of the invention are in one preferred instance shuttle constructs, that is the constructs are able to replicate in bacterial systems and then be used for expression in eukaryotic systems. The constructs may therefore typically have a bacterial origin of replication to allow maintenance of the constructs in bacterial hosts and in particular in *E. coli*. Any suitable origin of replication may be employed. In one preferred instance, the R6K origin of replication may be employed. The R6K origin is activated by the R6K specific initiator protein B encoded by the pir gene and hence constructs of the invention comprising the R6K origin will typically be grown in strains expressing the pir gene. Any suitable strain expressing the pir gene may be employed. In a preferred instance, constructs of the invention employing the R6K origin are grown in the *E. coli* strain GT115, EC100Dpir-116 or DH10Bpir116.

In a particularly preferred instance, the origin of replication may comprise the sequence of nucleotides 2599 to 2870 of SEQ ID No: 4, a functional fragment thereof, or a functional variant of either. The fragment and variants may be any of the lengths and possess any of the levels of sequence identity specified herein. The level of functionality may be any of the levels specified herein. For instance, functionality may be measured by the yield of construct in comparison to the same construct, but with the original origin of replication under equivalent conditions for the same period of time. Yield may, for instance, be at least 10%, at least 25%, preferably at least 50%, more preferably at least 75% and even more preferably at least 90% in comparison to constructs with the original origin of replication.

In a further preferred instance, a construct of the invention may comprise a gene for expression in bacteria and in particular a bacterial selection marker. Any appropriate selection marker may be employed. In one preferred embodiment a kanamycin selection marker is employed. Employing the kanamycin resistance marker has the advantage that it is particularly suitable for use in constructs for administration to human subjects. In particular, the Kanamycin coding sequences of nucleotides 2878 to 3693 of SEQ ID No:4 may be employed, or a functional fragment thereof, or a functional variant of either. The kanamycin gene sequence is presented counterclockwise in SEQ ID No:4 and hence the gene is translated from nucleotides 3693 to 2878. The kanaymcin gene unit of nucleotides 2878 to 3693 may in a preferred instance be present in a construct of the invention or indeed a functional fragment thereof or a functional variant of either. Functionality may be measured by the ability to select for the plasmid in bacteria effectively.

The use of the hCEFI promoter means that the constructs of the invention typically give rise to high and sustained gene expression. In addition, a construct of the invention may also have been designed to reduce content of CpG dinucleotides. CpG dinucleotides can induce inflammation when administered and in particular may induce flu like symptoms, cytokine expression and activation and migration of inflammatory cells. Whilst CpG dinucleotides may assist when constructs are being used for vaccination to generate an immune response, such inflammation is undesirable when wanting to use constructs to express genes for other purposes such as to treat genetic defects.

The constructs of the invention may be any type of construct. In one preferred instance of the invention the construct may be a non-viral construct. In an alternative embodiment, the construct may be a viral construct. The constructs of the present invention may, for instance, be plasmids, cosmids, YACs and in an especially preferred instance be plasmids. The hCEFI promoter may be employed with any appropriate plasmid backbone. In one instance, the constructs of the invention may be integrated into the genome of a cell, in another they may not be so integrated. In one instance a construct of the invention may be provided in circularised form, in another it may be provided in linear form and may have been lineraised. A construct of the invention may comprise a restriction site for linearisation.

In one instance, a promoter of the invention may be employed in a viral construct. In a particularly preferred instance, such a construct may be a viral construct that integrates into the genome of cells. In a preferred instance, such constructs may lack, or the gene comprising the promoter may lack, or have a reduced number of, CpG dinucleotides as outlined herein.

In a particularly preferred instance, a viral construct of the invention employing the hCEFI promoter may be a retroviral or a lentiviral construct. Retroviral constructs and lentiviral constructs integrate into the genome of cells and expression from their genes can be decreased or silenced due to methylation of CpG dinucleotides. Thus, in a particularly preferred instance, the hCEFI promoter in such constructs will lack CpG dinucleotides, preferably the gene comprising the hCEFI promoter and sequences to be expressed will lack CpG dinucleotides and in particular one or more of any of the other elements referred to herein present in the construct will lack CpG dinucleotides. In a further preferred instance, there will be no CpG dinucleotides within the gene comprising the hCEFI promoter, preferably within 100 bp, more preferably within 250 bp, still more preferably within 500 bp and even more preferably within 1000 bp upstream of the hCEFI promoter and/or downstream of the end of the transcribed unit or in some instances not within at least such distances. In one instance, there may be no CpG dinucleotides within such distances from the hCEFI promoter either 5 and/or 3' and preferably both. In one instance, the construct may lack CpG dinucleotides altogether or only have any of the numbers of CpG dinucleotides specified herein.

The constructs of the invention may typically be in a form suitable for administration to any of the subjects mentioned herein and in particular to humans. In one preferred instance, the constructs do not include matrix attachment regions (MAR), although in others they may do so. In one embodiment, the constructs do not employ a zeocin resistance gene. In another preferred instance, a construct of the invention may, for instance, not comprise any of the Beta-globin MAR, IFN-beta MAR, a zeocyin resistance gene and/or the SV40 polyadenylation signal.

In one preferred embodiment, the invention provides a construct comprising a hCEFI promoter, where a coding sequence can be cloned into the vector via a restriction enzyme site. In particular, such a construct is provided which comprises a restriction site into which a coding sequence can be inserted in operable linkage with the hCEFI promoter. The restriction site, may, for instance, be a restriction enzyme site for any of the restriction enzymes mentioned herein. In one instance, the restriction site is a NheI or an ApaI restriction site.

The restriction site may be unique to the construct. Such a construct may comprise any of the other elements mentioned herein. In a particularly preferred instance, such a construct comprises an initial exon or exons and an intron or intron so that a coding sequence can simply be inserted into operable linkage with them.

In one particularly preferred instance, a construct is provided which comprises:
(i) the sequence of SEQ ID No:1; or
(ii) a construct with at least 70% sequence identity to (i) and which comprises a hCEF1 promoter of the invention.

A construct with any of the levels of sequence identity specified herein to SEQ ID No:1 may be provided. The invention also comprises a method comprising inserting a coding sequence into such a construct so that it is operably linked to the hCEFI promoter. The invention also provides such a construct with the sequence to be expressed cloned into it in operable linkage with the hCEFI promoter including any of the sequences referred to herein.

In a further preferred instance, the present invention provides a construct, wherein the sequence to be expressed operably linked to the hCEFI promoter encodes a CFTR polypeptide, where the construct comprises:
(i) the sequence of SEQ ID No:2, or a variant of SEQ ID No:2 in which nucleotide 2595 is C, nucleotide 3234 is T and nucleotide 3236 is C; or
(ii) a construct with at least 70% sequence identity to (i) and which comprises a hCEF1 promoter as defined in any one of the preceding claims.

A construct with any of the levels of sequence identity specified herein to SEQ ID No:2 is provided which encodes a functional CFTR gene able to wholly, or at least partially, correct CFTR expression operably linked to a hCEF1 promoter of the invention. In a preferred instance, the variant construct will comprise the CFTR coding sequence of SEQ ID No:2 and hence express the same protein. Functional fragments and variants of the specific CFTR coding sequence may be employed. Variants and fragments will preferably be codon optimised.

In a further preferred instance, the present invention provides a construct, wherein the sequence to be expressed operably linked to the hCEFI promoter encodes a luciferase polypeptide, where the construct comprises:
(i) the sequence of SEQ ID No:4; or
(ii) a construct with at least 70% sequence identity to (i) and which comprises a hCEF1 promoter as defined in any one of the preceding claims.

A variant construct may have any of the levels of sequence identity specified herein to SEQ ID No:4 and in particular may have the same luciferase coding sequence as SEQ ID No:4.

In a further instance, the luciferase coding sequence may be replaced by sequences encoding any marker gene. Thus in one embodiment a construct of the invention may comprise a marker or a reporter gene in operably linkage with the hCEFI promoter. Examples of reporter genes whose coding sequences may be used include chloramphenicol acetyltransferase, β-galactosidase, β-glucuronidase, and green fluorescent protein. Functional fragments and functional variants may also be employed.

In some instances, a construct of the invention may comprise sequences encoding a sequence allowing purification of the expressed polypeptide such as a histidine tag or a c-myc sequence or other antibody detection sequence. Constructs may also comprise the coding sequences for signals for secretion from a cell. In some instances, the construct of the invention may comprise such sequences and a coding sequence can then be cloned into the construct as appropriate in operable linkage with such sequences.

In another preferred instance, the coding sequence operably linked to the hCEFI promoter may have been codon optimised for expression in the appropriate subject and in particular for expression in humans. The specific luciferase and CFTR coding sequences provided herein are provided which have been codon optimised as are functional fragments and functional variants thereof with any of the levels of sequence identity, length and other features specified herein.

The coding sequences cloned into the constructs of the invention may be any appropriate size for the construct in question. Thus, for instance, a plasmid may comprise a coding sequence of from 30 bp to 25 kb, though smaller or larger coding sequences may in some instances be employed. In some instances, the coding sequences may be from 250 to 30 kb, preferably from 300 bp to 25 kb, more preferably from 500 bp to 20 kb, more preferably still from 500 bp to 15 kb and even more preferably from 1000 bp to 10 kb. The range may comprise any combination of those sizes and the sequence to be expressed will typically dictate the length of the coding sequence. Constructs such as cosmids and YACs may comprise larger inserts. An appropriate construct for the coding sequence to be expressed will be chosen.

A construct of the invention may be substantially free of, or associated with, cells or with cellular material. It may be in substantially isolated form, or it may be in substantially purified form, in which case it will generally comprise at least 90% e.g. at least 95%, 98% 99% or more of the polynucleotide or dry mass in the preparation.

CpG Dinucleotides

In an especially preferred embodiment of the invention, one or more of the elements, and preferably all of the construct, will lack CpG dinucleotides. Such constructs are particularly useful where the constructs are not intended to be used to generate an immune response against an antigen. The presence of CpG dinculeotides can generate flu like symptoms and inflammation, particularly when administered in the airway. The elimination of CpG dinucleotides can help eliminate such effects.

The inflammatory response observed after plasmid/liposome complex delivery arises in part from the recognition of the unmethylated CpG dinucleotides present in the bacterially derived pDNA. Mammalian DNA differs from bacterial DNA in that the frequency of CpG dinucleotides is severely suppressed compared to that of bacterial DNA and most mammalian CpG sequences are methylated. Bacterially derived plasmid DNA activates several immune/inflammatory cell types, including B cells, macrophages, dendritic cells, and natural killer cells. As shown in the Examples of the present application, the presence of a single CpG dinucleotide can lead to an inflammatory response.

Several strategies could be employed to decrease the immunostimulatory properties of constructs. One approach might be to enzymatically methylate all CpG sequences. While the in vitro methylation of all the CpG dinucleotides within a given pDNA significantly decreases inflammatory consequences of plasmid/liposome delivery to the lung, it also severely inhibits transgene expression. Thus, although methylation may be employed in a preferred instance it is not.

An alternative approach which may be employed in the present invention is to eliminate or reduce the frequency of CpG sequences in the constructs of the invention. This may, for instance, be done by eliminating nonessential regions within the construct (e.g., sequences flanking the origin of replication) and also, for instance, by redesigning regulatory elements and open reading frames to minimise CpG sequences.

Thus, for instance, elements and constructs employed in the invention may have been modified to eliminate at least one, preferably at least five, even more preferably at least ten, still more preferably at least 20 and in some instances at least 30 CpG dinucleotides from the naturally occurring sequence.

The presence of minimal or no CpG dinucleotide content helps minimise inflammatory responses induced by the vector. Thus, the promoter, or other element and preferably the construct as a whole may, for instance, comprise less than 15, preferably less than 10, more preferably less than 5, even more preferably 4, 3, 2, 1 or zero CpG dinucleotides. In an especially preferred embodiment the promoter will comprise no CpG dinucleotides to eliminate immune responses induced by the CpG dinucleotides.

In one preferred embodiment, constructs of the invention will have been modified to eliminate at least one CpG nucleotide from the hCEFI promoter, operably linked sequence for expression, the kozak sequence, polyadenylation signal, origin of replication and/or selection marker, if present, may each, or all, have been so modified. In some instances, at least two, preferably at least five, more preferably at least ten, more preferably at least fifteen and even more preferably at least twenty, more preferably at least 50 and still more preferably at least 100 CpG dinucleotides and yet more preferably all CpG dinucleotides may have been eliminated from a particular element or the construct as a whole. Site directed mutagenesis and the synthesis of specific sequence oligonucleotides may, for instance, be used to eliminate CpG dinucleotides as may any appropriate molecular biology technique.

The invention provides the CFTR coding sequence of nucleotides 738 to 5180 of SEQ ID No:2, a functional fragment thereof or a functional variant thereof and in particular where such sequences have no CpG dinucleotides. The level of sequence identity or the length of the variant or fragment may be any of those specified herein. More specifically, the invention provides for a variant of the CFTR coding region of nucleotides 738 to 5180 of SEQ ID No:2, wherein the nucleotide at position 2595 is a C rather than an A, thus changing the codon from AAT which encodes Asparagine to CAT which encodes Histidine at amino acid position 620 in the corresponding polypeptide. The CFTR coding region of SEQ ID No:2 may additionally or alternatively be amended such that the nucleotide at position 3234 is a T rather than an C and the nucleotide at position 3236 is a C rather than a G, thus changing the codon from CTG which encodes Leucine to TTC which encodes Phenylalanine at amino acid position 833 in the corresponding polypeptide.

The invention also provides functional fragments or functional variants of a CFTR coding sequence which includes either or both of the above-mentioned codon changes.

It is intended that all reference herein to a CFTR coding sequence shall include the sequence of nucleotides 738 to 5180 of SEQ ID No:2, and a variant thereof with either of both the above-mentioned codon changes. Similarly, the invention allows for plasmid constructs including a CFTR coding sequence with either or both the codon changes. Preferably both the codon changes are made.

Changes to the sequence of the CFTR gene, or indeed any part of the construct, may be made using any suitable technique this may include using PCR to produce replacement fragments or synthesising replacement fragments and cloning these fragments into the construct. The effect of the presence of CpG dinucleotides may be studied using any appropriate assay. In particular, a sequence under test may be administered to a non-human animal and preferably inflammation measured. In one preferred instance mice are employed and in particular airway administration. Parameters such as inflammatory cell counts, in particular neutrophil counts, and cytokines levels such as TNF-α, IFN-γ, and IL-12 may, for instance, be measured.

Sequences to be Expressed and Conditions

The constructs of the invention may comprise any appropriate sequence for expression operably linked to the hCEFI promoter. In a particularly preferred instance, the sequence to be expressed may comprise a coding sequence and hence encode a polypeptide. In others, the sequences for expression may be transcribed to give rise to RNA molecules which are either functional themselves, or are processed to give rise to functional RNA molecules. For instance, constructs of the invention may be used to express antisense RNAs, siRNAs and ribozymes and they may therefore be used to modulate the expression of any of the genes mentioned herein and in particular to decrease or suppress expression.

In the instance where the sequence operably linked to the hCEFI promoter comprises a coding sequence which is translated to give rise to a polypeptide, any suitable polypeptide may be expressed. The polypeptide expressed may, for instance, be a therapeutic polypeptide, an enzyme, a structural protein, a membrane channel or a component thereof, an inhibitor (in particular an enzyme inhibitor), a signalling molecule (such as a cytokine) or any polypeptide it is desired to be expressed. For any of the polypeptides mentioned herein, functional fragments and functional variants may also be expressed.

In one embodiment the expressed polypeptide may be a therapeutic polypeptide. In particular, the polypeptide may compensate for a genetic defect which means that a particular gene product is absent or defective in a subject. The condition may be one that a particular polypeptide is missing or defective in all cells or alternatively in only particular cell types, tissues or organs. In some instances, expression of the polypeptide may be needed in the lung, liver, muscle, brain, and/or eyes. A preferred muscle tissue is the heart. Thus, the constructs of the invention may be used to express the chosen sequences in such tissues. In a particularly preferred instance, the tissue is lung or liver and in particular lung.

In a preferred embodiment of the invention, the tissue in which it may be desired to achieve expression of the sequences linked to the hCEFI promoter may be the lung. In a particularly preferred instance, the condition to be treated is an airway disorder or a disease affecting the lung.

In a preferred instance, the expressed sequence, and in particular polypeptide, may be one intended to treat one or more of the disorders Cystic Fibrosis, asthma, emphysema, chronic obstructive pulmonary disease (COPD), Acute Respiratory Distress Syndrome (ARDS), bronchitis and pneumonia. In an especially preferred instance cystic fibrosis may be treated.

In one embodiment, the construct may express a sequence for treating acute or chronic bronchial pulmonary disease, such as infectious pneumonia, bronchitis or tracheobronchitis, bronchiectasis, tuberculosis, and/or fungal infections. The subject may have a respiratory tract infection. The subject may have sinusitis, sinus congestion or viral infections which infect the respiratory system such as a cold or flu. The constructs may express sequences for treating such conditions.

In an especially preferred instance, the coding sequence encodes a polypeptide for treating Cystic Fibrosis and in particular encodes a Cystic Fibrosis Transmembrane Conductance Regulator (CFTR), a functional fragment thereof or a functional variant of either. The encoded polypeptide may, for instance, be alpha-1-antitrypsin and hence the construct may be used to treat emphysema. For conditions such as COPD, and ARDS, in a preferred instance, the polypeptides encoded may be heat shock proteins (HSP-70) or anti-inflammatory cytokines, and in particular interleukins and preferably IL-10.

Various therapeutic agents have previously been proposed for treatment of asthma and other chronic inflammatory airway diseases (see, for example, Demoly et al., Gene Therapy (1997) 4, 507-516) and could also be advantageously expressed in the airways by means of an expression construct in accordance with the invention. By way of example of particular genes which may be expressed from the constructs of the invention, the following are listed: soluble CD40, IL-1R, IL-4R, TNF receptor, IL-10, IL-12, Interferon γ, TGF β and polypeptide inhibitors of the human nuclear factor kappa Beta transcription factor. Examples of coding sequences to be expressed include:

GenBank accession no. M27492 (soluble fragment of human IL-R gene product) and Sims et al., Cloning the interleukin 1 receptor from human T cells, Proc. Natl. Acad. Sci USA (1989) 86, 8946-8950:

GenBank accession no. X52425 (soluble fragment of human IL4-R gene product; Idzerda et al., Human interleukin 4 receptor confers biological responsiveness and defines a novel receptor superfamily, J. Exp. Med. (1990) 171, 861-873;

GenBank accession no. U53483 (soluble fragment of human TNF receptor gene product; Santee et al., Human tumour necrosis factor receptor p75/80 (CD120b) gene structure and promoter characterization, J. Biol. Chem. (1996) 271, 21151-21159;

GenBank accession no. X13274 (human IFN; gene product); Gray et al., Expression of human immune interferon cDNA in *E. coli* and monkey cells, Nature (1982) 295, 503-504;

GenBank accession no. M57627 (human IL-10 gene product); Vieira et al., Proc. Natl. Acad. Sci. USA (1991) 88, 1172-1176;

GenBank accession nos. AF180562 and AF180563 (IL-12 chains; p35 and p40 gene products);

GenBank accession no. X02812 (human TGFβ gene product); Derynck et al., Human transforming growth factor-beta complementary DNA sequence and expression in normal and transformed cells, Nature (1985) 316, 701-705.

The above sequences may be modified to eliminate or reduced the occurrence of CpG dinucleotides as may any of the coding sequences discussed herein. Functional fragments and variants may be employed.

In a further preferred embodiment, a construct of the invention may express a sequence for treating cancer. Examples of particular cancers include cancers of the lung, prostate, breast, colon, ovary, testes, bowel, melanoma, a lymphoma and a leukaemia. In a particularly preferred instance, the cancer is lung cancer and in particular non-small cell lung cancer.

In order to be used to treat cancer, the constructs of the invention may, in one instance, encode tumour suppressing genes such as p53 and Rb and in particular Rb. Examples of tumour expressor genes which may be expressed, and conditions they may be used to treat, include RB1 (retinoblastoma susceptibility gene), WT1 (Wilm's tumour gene), NF1 (neurofibromatosis type 1 gene), NF2 (neurofibromatosis type 2 gene), DCC (colorectal cancer), and BRCA1 and BRCA2 (breast cancer)

Constructs for use in accordance with the invention to treat lung Cancer may rely on the hCEFI to direct expression in the lungs of various therapeutic agents previously proposed for treatment of cancers, including, for example, preferably prodrug-converting enzymes. By prodrug-converting enzyme will be understood a gene product which activates a compound with little or no cytotoxicity into a toxic product. Various prodrug activation strategies have previously been proposed for cancer treatment (see, for example, Published International Application no. WO 95/07994 and EP-B 0 702 084 of Chiron Corp.) and may be adopted by provision of a vector in accordance with the present invention together with the appropriate prodrug and in particular in the lung. Thus, for example, a vector for use in lung cancer therapy may preferably be constructed such that a hCEFI thereof directs expression of a viral thymidine kinase, e.g.Herpes simplex virus thymidine kinase. For prodrug-activation therapy, such an enzyme is employed together with a purine or pyrimidine analogue, e.g. ganciclovir, which is phosphorylated by the viral thymidine kinase to a toxic triphosphate form. Examples of other prodrug-converting enzymes which may be advantageously expressed from a hCEFI promoter in the lungs for prodrug activation therapy of cancer and in particular lung cancer include:

- cytosine deaminase which converts the prodrug 5-fluorocytosine into the toxic compound 5-fluorouracil (Mullen, Proc. Natl. Acad. Sci. USA (1992) 89, 33; see also Efficacy of adenovirus-mediated CD/5-FC and HSV-1 thymidine kinase/ganciclovir suicide gene therapies concomitant with p53 gene therapy, Xie et al., Clinical-Cancer Res. (1999) 5, 4224-4232);
- carboxypeptidase G2 which will cleave the glutamic acid from para-N-bis(2-chloroethyl)aminobenzoyl glutamic acid thereby creating a toxic benzoic acid mustard;
- Penicillin-V amidase which will convert phenoxyacetabide derivatives of doxorubicin and melphalan to toxic compounds (Vrudhula et al., J. Med. Chem. (1993) 36, 919-923; Kern et al., Canc. Immun. Immunother. (1990) 31, 202-206);
- Platelet-derived endothelial cell growth factor/thymidine phosphorylase (PD-ECGF/TP) which converts the prodrug 5'-deoxy-5-fluorouracil (Furtulon) to 5-fluorouracil and 5'-deoxy-D-ribose-1-phosphate (see, for example, Thymidine phosphorylase activity and prodrug effects in a three-dimensional model of angiogenesis; implications for the treatment of ovarian cancer, Stevens et al., Am. J. Pathol. (1998) 153, 1573-1578); and
- E. coli nitroreductase which has been utilized with the prodrug CB1954 (The nitroreductase/CB1954 combination in Epstein-Barr virus-positive B-cell lines:induction of bystander killing in vitro and in vivo, Westphal et al., Cancer-Gene-Therapy (January 2000) 7, 97-106).

In other preferred embodiments, constructs for treating cancer may encode cytotoxic gene products and/or prodrugs including combinations of HSVtk/GCV and CD/5-FC or indeed one of each combination may be expressed from a construct of the invention. Metastases could, for instance, be treated with constructs encoding IL-12, FAS to modulate host gene expression or cytotoxic gene product/pro-drug combinations. Again, one of the combination may, in some instances, be administered itself in combination with a construct of the invention expressing the other member of the combination. In some instances, a construct of the invention may express a ribozyme, siRNA or an anti-sense RNA to repress gene expression in tumour cells and hence treat cancer. In a preferred instance, any such elements to treat cancer may be used to treat lung cancer.

In a further aspect of the invention, the construct may express a polypeptide to treat a muscle condition and in particular a muscular dystrophy. Constructs of the invention may therefore be administered so that they express dystrophin, mini-dystrophin or utrophin genes and particularly in skeletal muscle to treat such conditions. Fragments and functional variants may be employed.

The constructs of the invention may also be used to express angiogenic factors. Angiogenic factors which may be expressed include Angiogenin, Angiopoietin-1, Del-1, Fibroblast growth factors including acidic (aFGF) and basic (bFGF) Follistatin, Granulocyte colony-stimulating factor (G-CSF), Hepatocyte growth factor (HGF)/scatter factor (SF), Interleukin-8 (IL-8), Leptin, Midkine, Placental growth factor, Platelet-derived endothelial cell growth factor (PD-ECGF), Platelet-derived growth factor-BB (PDGF-BB), Pleiotrophin (PTN), Progranulin, Proliferin, Transforming growth factor-alpha (TGF-alpha), Transforming growth factor-beta (TGF-beta), Tumor necrosis factor-alpha (TNF-alpha), Vascular endothelial growth factor (VEGF), and vascular permeability factor (VPF). Particularly referred angiogenic factors include fibroblast growth factor (FGF) or vascular endothelial growth factor (VEGF).

Angiogenic factors may be used to treat any conditions where it is desired to stimulate blood vessel growth. Examples of such conditions include coronary artery disease, stroke, and delayed wound healing.

The constructs of the invention may also be used to express anti-angiogenic factors. Examples of antiangiogenic factors include Angioarrestin, Angiostatin (plasminogen fragment), Antiangiogenic antithrombin III, Cartilage-derived inhibitor (CDI), CD59 complement fragment, Endostatin (collagen XVIII fragment), Fibronectin fragment, Gro-beta, Heparinases, Human chorionic gonadotropin (hCG), Interferon alpha/beta/gamma, Interferon inducible protein (IP-10), Interleukin-12, Kringle 5 (plasminogen fragment), Metalloproteinase inhibitors (TIMPs), Placental ribonuclease inhibitor, Plasminogen activator inhibitor Platelet factor-4 (PF4), Prolactin 16 kD fragment, Proliferin-related protein (PRP) Retinoids, Tetrahydrocortisol-S, Thrombospondin-1 (TSP-1), Transforming growth factor-beta (TGF-$\beta$), Vasculostatin and Vasostatin (calreticulin fragment).

Constructs of the invention may be used in the treatment of excessive angiogenesis. Examples of conditions that may therefore be treated with such constructs include cancer, diabetic blindness, age-related macular degeneration, rheumatoid arthritis, and psoriasis.

In another particularly preferred instance of the invention, constructs may be used to express sequences in epithelium and in particular eye epithelium. Thus, constructs of the invention may be used to treat macular degeneration (AMD)

and hence the invention provides constructs expressing pigment epithelium-derived factor (PEDF) to alter cell growth and also constructs which express vascular endothelial growth factor (VEGF) inhibitor.

In one instance, the construct may express Factor VIIa, factor VIII, factor IX, glucocerebrosidase, alpha-galactosidase, acid alpha-glucosidase, alpha-n-acetylgalactosaminidase, acid sphingomyelinase, alpha-iduronidase, dystrophin or alpha-1-antitrypsin.

In one instance, the coding sequences expressed via the hCEFI may encode an antigen, immunogenic fragment thereof or immunogenic variant of either. The antigen may in particular be a viral, bacterial, parasitic or fungal pathogen antigen or a tumour antigen. The antigen may be an allergen antigen. In one preferred instance, the antigen is a viral antigen, an immunogenic fragment thereof or an immunogenic variant of either.

In embodiments where the intention is to elicit an immune response against an antigen, a construct, or its element or elements, may not have been modified to remove CpG dinucleotides in one instance. In an alternative instance, they may have been. The hCEFI promoter gives strong and sustained expression and hence will be useful in eliciting an immune response.

Thus, the present invention also provides a vaccine comprising a construct of the invention encoding an antigen and a pharmaceutically acceptable carrier or excipient. The invention also provides a method of vaccination or immunisation comprising administrating a construct of the invention. Such methods will preferably result in a protective immune response against the pathogen which the antigen is designed to give an immune response against. In the case of allergens and autoantigens administration may intentionally result in tolerance.

Subsequent immunisations or vaccinations may be used to boost the immune response seen. Immunogenic fragments and immunogenic variants of specific antigens may be expressed.

In one preferred embodiment a construct of the invention may encode a polypeptide for treating or preventing a cancer. In a particularly preferred embodiment, a construct of the invention may encode a tumour antigen, an immunogenic fragment thereof or an immunogenic variant of either. Examples of tumour associated antigens include, but are not limited to, cancer-testes antigens such as members of the MAGE family (MAGE 1, 2, 3 etc), NY-ESO-1 and SSX-2, differentiation antigens such as tyrosinase, gp100, PSA, Her-2 and CEA, mutated self antigens and viral tumour antigns such as E6 and/or E7 from oncogenic HPV types. Further examples of particular tumour antigens include MART-1, Melan-A, p97, beta-HCG, GalNAc, MAGE-1, MAGE-2, MAGE-4, MAGE-12, MUC1, MUC2, MUC3, MUC4, MUC18, CEA, DDC, P1A, EpCam, melanoma antigen gp75, Hker 8, high molecular weight melanoma antigen, K19, Tyr1, Tyr2, members of the pMel 17 gene family, c-Met, PSM (prostate mucin antigen), PSMA (prostate specific membrane antigen), prostate secretary protein, alpha-fetoprotein, CA125, CA19.9, TAG-72, BRCA-1 and BRCA-2 antigen.

Examples of particular cancers that the antigen may be derived include those from cancers of the lung, prostate, breast, colon, ovary, testes, bowel, melanoma, a lymphoma and a leukaemia. The constructs of the invention may also be used to treat or prevent such cancers.

The construct may encode an antigen for the treatment or prevention of a number of conditions including but not limited to cancer, allergies, toxicity and infection by a pathogen such as, but not limited to, a fungus, a virus including Human Papilloma Virus (HPV), HIV, HSV2/HSV1, influenza virus (types A, B and C), Polio virus, RSV virus, Rhinoviruses, Rotaviruses, Hepatitis A virus, Norwalk Virus Group, Enteroviruses, Astroviruses, Measles virus, Para Influenza virus, Mumps virus, Varicella-Zoster virus, Cytomegalovirus, Epstein-Barr virus, Adenoviruses, Rubella virus, Human T-cell Lymphoma type I virus (HTLV-I), Hepatitis B virus (HBV), Hepatitis C virus (HCV), Hepatitis D virus, Pox virus, Marburg and Ebola; a bacterium including *M. tuberculosis, Chlamydia, N. gonorrhoeae, Shigella, Salmonella, Vibrio Cholera, Treponema pallidua, Pseudomonas, Bordetella pertussis, Brucella, Franciscella tulorensis, Helicobacter pylori, Leptospria interrogaus, Legionella pnumophila, Yersinia pestis, Streptococcus* (types A and B), *Pneumococcus, Meningococcus, Hemophilus influenza* (type b), *Toxoplama gondii, Complybacteriosis, Moraxella catarrhalis, Donovanosis*, and *Actinomycosis*; fungal pathogens including Candidiasis and Aspergillosis; parasitic pathogens including *Taenia*, Flukes, Roundworms, Amebiasis, Giardiasis, *Cryptosporidium, Schitosoma, Pneumocystis carinii*, Trichomoniasis and Trichinosis.

The nucleic acid my also be used to provide a suitable immune response against numerous veterinary diseases, such as Foot and Mouth diseases, Coronavirus, *Pasteurella multocida, Helicobacter, Strongylus vulgaris, Actinobacillus pleuropneumonia*, Bovine viral diarrhea virus (BVDV), *Klebsiella pneumoniae, E. coli, Bordetella pertussis, Bordetella parapertussis* and *Bordetella brochiseptica*.

In one instance a nucleic acid construct of the invention may encode an antigen from a member of the adenoviridae (including for instance a human adenovirus), herpesviridae (including for instance HSV-1, HSV-2, EBV, CMV and VZV), papovaviridae (including for instance HPV), poxviridae (including for instance smallpox and vaccinia), parvoviridae (including for instance parvovirus B 19), reoviridae (including for instance a rotavirus), coronaviridae (including for instance SARS), flaviviridae (including for instance yellow fever, West Nile virus, dengue, hepatitis C and tick-borne encephalitis), picornaviridae (including polio, rhinovirus, and hepatitis A), togaviridae (including for instance rubella virus), filoviridae (including for instance Marburg and Ebola), paramyxoviridae (including for instance a parainfluenza virus, respiratory syncitial virus, mumps and measles), rhabdoviridae (including for instance rabies virus), bunyaviridae (including for instance Hantaan virus), orthomyxoviridae (including for instance influenza A, B and C viruses), retroviridae (including for instance HIV and HTLV) and hepadnaviridae (including for instance hepatitis B). In a further preferred instance the antigen may be from a pathogen responsible for a veterinary disease and in particular may be from a viral pathogen, including, for instance, a Reovirus (such as African Horse sickness or Bluetongue virus) and Herpes viruses (including equine herpes). The antigen may be one from Foot and Mouth Disease virus. In a further preferred instance the antigen may be from a Tick borne encephalitis virus, dengue virus, SARS, West Nile virus and Hantaan virus.

The antigen may be a fungal antigen, such as a *Candida* or *Aspergillus* antigen. In particular, it may be from *Candida albicans* or *Aspergillus fumigatus*. The antigen may be from *Sporothrix* (e.g. from *Sporothrix schenckii*), *Histoplasma* (e.g. from *Histoplasma capsulatum*) *Cryptococcus* (e.g. from *Cryptococcus neoformans*) or *Pneumocystis* (e.g. from *Pneumocystis carinii*). The antigen may be from a parasitic pathogen and may, in particular, be from *Taenia*, Flukes, Roundworms, Amebiasis, Giardiasis, *Cryptosporidium, Schistosoma, Pneumocystis carinii*, Trichomoniasis and Trichinosis.

In some cases the antigen may be an antigen from a prion. In particular, the antigen may be one from the causative agent of kuru, Creutzfeldt-Jakob disease (CJD), scrapie, transmissible mink encephalopathy and chronic wasting diseases, or from a prion associated with a spongiform encephalopathy, particularly BSE. The antigen may be from the prion responsible for familial fatal insomnia.

In some cases the antigen may be from a parasitic pathogens including, for example, one from the genera *Plasmodium, Chtamydia, Trypanosome, Giardia, Boophilus, Babesia, Entamoeba, Eimeria, Leishmania, Schistosome, Brugia, Fascida, Dirofilaria, Wuchereria* and *Onchocerea*. Examples of preferred antigens from parasitic pathogens to be expressed as the heterologous antigen include the circumsporozoite antigens of *Plasmodium* species, such as the circumsporozoite antigen of *P. bergerii* or the circumsporozoite antigen of *P. falciparum*; the merozoite surface antigen of *Plasmodium* species; the galactose specific lectin of *Entamoeba histolytica*; gp63 of *Leishmania* species; paramyosin of *Brugia malayi*; the triose-phosphate isomerase of *Schistosoma mansoni*; the secreted globin-like protein of *Trichostrongylus colubriformis*; the glutathione-S-transferases of *Frasciola hepatica, Schistosoma bovis* and *S. japonicum*; and KLH of *Schistosoma bovis* and *S. japonicum*.

The antigen may be an auto-antigen. In particular, the antigen may an antigen associated with an autoimmune disease. Auto-antigens include those associated with autoimmune diseases such as multiple sclerosis, insulin-dependent type 1 diabetes mellitus, systemic lupus erythematosus (SLE) and rheumatoid arthritis. The antigen may be one associated with, Sjorgrens syndrome, *myotis, scleroderma* or Raynaud's syndrome. Further examples of auto-immune disorders that the antigen may be associated with include ulcerative colitis, Crohns' disease, inflammatory bowel disorder, autoimmune liver disease, or autoimmune thyroiditis. Examples of specific autoantigens include insulin, glutamate decarboxylase 65 (GAD65), heat shock protein 60 (HSP60), myelin basic protein (MBP), myelin oligodendrocyte protein (MOG), proteolipid protein (PLP), and collagen type II. In cases where the antigen is an autoantigen the antigen will typically be administered in order to promote tolerance to the auto-antigen. Although in some cases models of the diseases may be produced using constructs of the invention to be produce an immune response.

In some cases the antigen may be an allergen. The allergenic antigen may be any suitable antigen from an antigen. For example, the allergen may be from *Ambrosia artemisiifolia, Ambrosia trifida, Artemisia vulgaris, Helianthus annuus, Mercurialis annua, Chenopodium album, Salsola kali, Parietaria judaica, Parietaria officinalis, Cynodon dactylon, Dactylis glomerata, Festuca pratensis, Holcus lanatus, Lolium perenne, Phalaris aquatica, Phleum pratense, Poa pratensis* or *Sorghum halepense*. The allergen antigen may be from a tree, such as, for example, from *Phoenix dactylifera, Betula verrucosa, Carpinus betulus, Castanea sativa, Corylus avellana, Quercus alba, Fraxinus excelsior, Ligustrum vulgare, Olea europea, Syringa vulgaris, Plantago lanceolata, Cryptomeria japonica, Cupressus arizonica, Juniperus oxycedrus, Juniperus virginiana,* or *Juniperus sabinoides*. In some cases the antigen may be from an antigen from a mite such as, for example, from *Acarus siro, Blomia tropicalis, Dermatophagoides farinae, Dermatophagoides microceras, Dermatophagoides pteronyssinus, Euroglyphus maynei, Glycyphagus domesticus, Lepidoglyphus destructor* or *Tyrophagus putrescentiae*.

The allergen antigen may be from an animal such as, for example, from a domestic or agricultural animal. Examples of allergens from animals include those from cattle, horses, dogs, cats and rodents (e.g. from rat, mouse, hamster, or guinea pig). In some cases the antigen may be from a food allergen and in others it may be from insect.

In another preferred case the antigen may be from a retroviradae (e.g. HTLV-I; HTLV-11; or HIV-1 (also known as HTLV-111, LAV, ARV, hTLR, etc.)). In particular from HIV and in particular the isolates HIVIIIb, HIVSF2, HTV-LAV, HIVLAI, HIVMN; HIV-1CM235, HIV-1; or HIV-2. In a particularly preferred embodiment, the antigen may be a human immunodeficiency virus (HIV) antigen. Examples of preferred HIV antigens include, for example, gp120, gp160 gp41, gag antigens such as p24gag and p55gag, as well as proteins derived from the pol, env, tat, vif, rev, nef, vpr, vpu or LTR regions of HIV. In a particularly preferred case the antigen may be HIV gp120 or a portion of HIV gp120. The antigen may be from an immunodeficiency virus, and may, for example, be from SIV or a feline immunodeficiency virus.

The antigen may be a model antigen. The antigen may be one commonly used in experiments to assess immune responses. For example the antigen may be a lysozyme and in particular chicken egg lysozyme. The antigen may be ovalbumin and in particular chicken ovalbumin.

Thus, the encoded polypeptide may be an antigen, an immunogenic fragment thereof or an immunogenic variant thereof and in particular any of the antigens mentioned herein, immunogenic fragments thereof or immunogenic variants of either. The fragment or variant may, for instance, have any of the levels of homology, proportion of the length of the original antigen, and functionality specified herein and in particular ability to give rise to an immune response.

In one instance a construct of the invention uses the hCEFI promoter to express an influenza antigen, an immunogenic fragment thereof or an immunogenic variant of either. The fragment and/or variant may have any of the levels of sequence homology, fragment lengths and/or levels of functionality specified herein. In particular, preferably a coding sequence of the construct encodes an influenza virus antigen, an immunogenic fragment of an influenza virus antigen or an immunogenic variant with 80% amino acid homology to any of the preceding or indeed with any of the levels of sequence identity specified herein.

For instance the influenza antigen may be an influenza NP (nucleoprotein/nucleocapsid protein), HA (hemagglutinin), NA (neuraminidase), M1, M2, PB1, PB2, PA, NS1 and/or NS2 antigens or may be a fragment or variant of such antigens. In a preferred embodiment the encoded antigen may be HA, NA and/or M2 influenza antigen or a fragment or a variant of such antigens. In an especially preferred instance, the encoded antigen may be an HA or an NA antigen or a fragment or variant of such antigens and in particular an HA antigen or a fragment or variant of such an antigen.

In one preferred embodiment the antigen may be from the H5N1 strain of influenza and immunogenic fragments thereof and variants of either which retain immunogenicity may be employed. In particular, the antigen may be one from the H5N1 strain or a fragment of such an antigen. Variants, for instance, with one, two, three, four, five or more amino acid changes may be employed as may variants with any of the levels of sequence identity, length and other features specified herein. Similarly fragments may have any of the levels of length and other parameters specified herein.

The influenza antigen may be from any influenza virus. The antigen may be from influenza virus A, B or C, in particular from influenza A and/or B. The antigen may, for instance, be from one of the strains identified annually by the World Health Organisation to be used in influenza vaccines and in particular may be an antigen identified by the WHO for such use.

Among the preferred therapeutic genes for delivery to cells, and hence for expression using constructs of the invention are the hematopoietic factors, including Factor VIIa [U.S. Pat. No. 4,784,950]; Factor VIII [U.S. Pat. Nos. 4,965,199; 4,868,112 [Bdomain deleted] and U.S. Pat. No. 5,661,008]; and Factor IX [U.S. Pat. No. 4,994,371]. Other preferred genes are those encoding lysosomal storage enzymes, including genes encoding glucocerebrosidase [Gaucher disease; U.S. Pat. Nos. 5,879,680; 5,236,838]; alpha-galactosidase [Fabry disease; U.S. Pat. No. 5,401,650]; acid alpha-glucosidase [Pompe disease; WO00/12740]; alphanacetylgalactosaminidase [Schindler disease; U.S. Pat. No. 5,382,524]; acid sphingomyelinase [Niemann-Pick disease; U.S. Pat. No. 5,686,240]; alpha-iduronidase [WO9310244A1]. Other preferred genes include the genes for, dystrophin, insulin and alpha-1-antitrypsin.

In some instances, the constructs of the invention may be used to express sequences in cells, tissues or organs directly affected by a condition. For instance, in Cystic Fibrosis, the constructs of the invention may be used to express CFTR in the cells of the lung to correct the organ most affected by the condition. In muscular dystrophy, the therapeutic gene may be expressed, for instance in skeletal muscle. In other instances, the intention may be to express sequences in one tissue so that the expressed polypeptide can be released and act on another tissue. Thus, in some instances, a particular cell type or tissue may be used as a factory for producing desired polypeptides. Preferred instances include using the lung, liver and/or muscle to produce proteins and in particular to secrete the polypeptides they produce. Examples include the production of clotting factors for haemophilia, metabolic enzymes for lysosomal storage defects, insulin for diabetes, alpha-1-antitrypsin for emphysema. Such an approach may be used for any of the conditions mentioned herein wherein the polypeptide does not have to be expressed directly in the target tissue or it is desired for the chosen polypeptide to enter systems such as the blood system so that the polypeptide is carried throughout the body.

In a further instance of the invention, the invention provides constructs expressing non-therapeutic polypeptides. In one instance, such constructs may be used to produce particular desired polypeptides in in vitro systems or alternatively in non-human animals.

Constructs of the invention may be used to express sequences in agricultural animals including any of those mentioned herein. Such expressed sequences may be therapeutic or non-therapeutic. Constructs of the invention may be used to express any of the gene products mentioned herein for treating diseases in animals. The polypeptides expressed may include appropriate sequences so that they are secreted into the blood or milk to facilitate harvest.

Constructs of the invention may be used to express polypeptides that enhance the value of agricultural animals. For instance, they may be used to express constructs that result in enhanced meat yield in animals used for their meat. For instance, a construct of the invention may be used to express hormones and in particular growth hormone, particularly to enhance meat yield. A construct of the invention may be used to express somatotropin. In a particularly preferred instance, a construct of the invention may be employed to express a somatropin to increase milk yield, particularly in animals such as cows and goats and in particular dairy cows and somatotropin may be employed, particularly the bovine protein, functional fragments thereof or functional variants of either.

For all of the expressed sequences referred to herein functional fragments of the specific sequences referred to may be employed as may functional variants of either. For instance, in the case of therapeutic polypeptides, as long as the fragment or variants retain some therapeutic benefit they may be employed and the degree of functionality may be any of those specified herein.

In some embodiments of the invention the hCEFI promoter may be used to express more than one polypeptide. Thus, in some cases a transcribed sequence may give rise to multiple polypeptides, for instance a transcript may contain multiple open reading frames (ORFs) and also one or more Internal Ribosome Entry Sites (IRES) to allow translation of ORFs after the first ORF. A transcript may be translated to give a polypeptide which is subsequently cleaved to give a plurality of polypeptides. In some cases a nucleic acid construct of the invention may comprise multiple hCEFI promoters and hence give rise to a plurality of transcripts and hence a plurality of polypeptides. Constructs may, for instance, express one, two, three, four or more polypeptides via a hCEFI promoter or promoters.

In an especially preferred embodiment of the present invention the hCEFI promoter may be used to express the CFTR polypeptide and hence the construct may be used to treat cystic fribosis. Cystic fibrosis (CF) is an inherited condition affecting approximately one in every 2000 Caucasians. The condition is caused by mutations in the cystic fibrosis transmembrane conductance regulator (CFTR) gene which encodes a cAMP-regulated chloride channel expressed on the surface of epithelial cells [Riordan, J. R., et al., Science, 1989. 245(4922): p. 1066-73]. The CFTR chloride channel has an important role in regulating the transepithelial transport of salt and water. Abnormality or absence of CFTR can result in disease in many organs of the body, but the major cause of morbidity and mortality in CF is lung disease [Pilewski, J. M. and R. A. Frizzell, Physiol Rev, 1999. 79(1 Suppl): p. S215-55]. Defective chloride secretion and elevated sodium absorption in the airways results in the development of thick mucus secretions in the lung and subsequent, chronic bacterial infection. Despite advances in treatment, this condition still leads to an untimely death, often in early adult life [Pilewski et al 1999 supra]. Transfer of a wild-type CFTR gene to proximal bronchial epithelial and submucosal gland cells is predicted to correct the chloride channel defect in CF [Drumm, M. L., et al., Cell, 1990. 62(6): p. 1227-33 and Hyde, S. C., et al., Nature, 1993. 362(6417): p. 250-5]. The constructs of the invention may be used to achieve expression in such tissues and in particular in such tissues in cystic fibrosis. The constructs may be delivered via any appropriate means to achieve delivery to such tissues.

Prior clinical trials evaluating CFTR gene delivery mediated by adenoviral vectors manifested limiting toxicities at pulmonary doses just sufficient to detect low levels of CFTR expression [Crystal, R. G., et al., Nat Genet, 1994. 8(1): p. 42-51; Knowles, M. R., et al., N Engl J Med, 1995. 333(13): p. 823-31; Wilmott, R. W., et al., Hum Gene Ther, 1996. 7(3): p. 301-18; and Zabner, J., et al., J Clin Invest, 1996. 97(6): p. 1504-11;]. Similar studies evaluating adeno-associated viral vectors have not shown toxicities, but the level of CFTR functional reconstitution has been modest [Conrad, C. K., et al., Gene Ther, 1996. 3(8): p. 658-68, Aitken, M. L., et al., Hum Gene Ther, 2001. 12(15): p. 1907-16, Wagner, J. A., et al., Hum Gene Ther, 2002. 13(11): p. 1349-59, Flotte, T. R., et al., Hum Gene Ther, 2003. 14(11): p. 1079-88]. Importantly, administration of either viral vector leads to the generation of neutralizing antibodies that abolish the efficacy of subsequent administrations [Zabner et al., 1996, supra, Harvey, B. G., et al., J Clin Invest, 1999. 104(9): p. 1245-55, Sun, J. Y., et al., Gene Ther, 2003. 10(11): p. 964-76, Moss, R. B., et al., Chest, 2004. 125(2): p. 509-21].

Constructs of the present invention expressing CFTR may be used to address the problems seen in prior art trials of genetic treatment for CF. In particular, as the invention provides constructs with minimal, or no, CpG dinucleotide content, flu like symptoms and inflammation resulting from such sequences has been minimised or eliminated. Furthermore, the hCEFI promoter of the present invention displays high-level and sustained expression. This means that therapy employing the constructs of the invention will have a prolonged effect. This may mean that the therapy has to be administered less often, which is important for genetic conditions in particular where the underlying genetic defect means that a condition has to be continuously treated. This may be particularly important for conditions such as cystic fibrosis where prolonged expression of CFTR will help restore lung function for more time. Thus, in an especially preferred instance, a construct of the invention may be used in the treatment of a genetic condition, in particular any of those mentioned herein and especially cystic fibrosis.

Subjects

In one aspect, the constructs of the invention may be administered to a subject. In a preferred instance, the constructs are administered to a mammal. In one preferred instance the subject is human and in particular the subject may be human where it is intended to treat a disease condition, particularly any of those mentioned herein.

In a further aspect, the subject may be non-human. In particular, the constructs of the invention may be administered to a non-human animal and preferably a non-human mammal. Such subjects may be suffering from any of the conditions mentioned herein. The constructs may, for instance, be administered to non-human domestic animals or an agriculturally important animal. For instance, the subjects may be cattle, pigs, horses, sheep or goats, they may be sports animals such as horses and dogs. The animal may be a domestic pet such as a dog or cat. The animal may be a monkey such as a non-human primate such as a chimpanzee, gorilla or orangutan. The subject may be a rabbit.

The constructs of the invention may be administered to avian subjects. Thus, for instance, the constructs may be administered to domestic, wild and game birds such as chickens, turkeys and other gallinaceous birds, ducks, and geese including such animals used for meat.

In a further preferred instance, the constructs of the invention may be administered to rodents. Examples of rodents include mice, rats, guinea pigs and hamsters and in particular mice and rats and especially mice. Constructs may be administered to such animals to assess their efficacy. They may be so administered to assess functionality of particular elements in the construct and also the construct as a whole. In one instance of the invention, a construct of the invention may be administered to an animal model of any of the conditions mentioned herein, including genetic and induced models. For instance, the constructs may be administered to knock-out and transgenic mouse models of any of the conditions mentioned herein and in one particularly preferred aspect knock-out or transgenic mouse models of CF may be administered with a construct of the invention and any reversal in the phenotype monitored.

The term subject does not denote a particular age. Thus, both adult and newborn individuals are intended to be covered. In one embodiment the subject is susceptible to or at risk from the relevant disease. In a further preferred embodiment, the subject has one of the disease conditions mentioned herein. The subject may have a genetic defect that the administration of the construct is designed to rectify and in particular any of the disease conditions referred to herein.

Formulation & Administration

In respect of introduction of a construct of the invention into cells, tissues or organs in vitro suitable methods for delivery of nucleic acids to such cells are known in the art and include, for example, dextran mediated transfection, calcium phosphate precipitation, electroporation and direct microinjection into nuclei. Thus, the invention provides a cell transformed with a construct of the invention. The invention provides a cell comprising a construct of the invention. In one instance, the present invention provides an isolated cell or population of cells comprising a construct of the invention. The present invention provides such cells in vitro. Cells of the present invention may be provided in frozen form for storage in some instances.

The constructs of the invention may be provided in any suitable form for administration to a subject. For instance, they may be in the form of naked DNA or complexed with one or more cationic amphiphiles, e.g. one or more cationic lipids (also called DNA/liposomes, plasmid DNA/liposomes or lipoplex). The constructs may be delivered either directly to a subject, or alternatively, delivered ex vivo to cells derived from the subject whereafter the cells are reimplanted in the subject. In a preferred instance, the constructs are delivered directly to the subject.

Any suitable delivery route may be used in the administration of the constructs of the invention. The constructs may be administered by enteral or parenteral routes such as via oral, buccal, anal, pulmonary, intravenous, intra-arterial, intramuscular, intraperitoneal, topical, via inhalation, via aerosols, subcutaneously, intramuscularly, intranasally or transmucosally. The constructs may be administered by needleless injection. Thus, the invention also provides carrier particles for needleless injection coated with a construct of the invention and needleless injection devices loaded with such coated carrier particles.

Preferably the constructs of the invention may be administered via inhalation and/or intra-nasally. Thus they may be delivered via the nose and/or mouth. Suitable methods for formulating and preparing medicaments to be administered via inhalation, installation and intranasally are well known in the art and may be employed in the present invention. Intranasal administration may, in some instances, be in the form of a fine powder or aerosol nasal spray or in particular cases in the form of modified Dischaler® or Turbohaler®. The constructs may also be administered via installation. In a preferred embodiment, the medicaments of the invention are suitable for administration by inhalation. For inhalation therapy the medicament may, for instance, be in a solution useful for administration by liquid aerosol, metered dose inhalers, or in a form suitable for a dry powder inhaler. The medicament may be present in a blister pack or breakable capsule.

In some preferred embodiments, the medicaments of the present invention may be formulated as aerosols. The formulation of pharmaceutical aerosols is routine to those skilled in the art, see for example, Sciarra, J. in Remington's Pharmaceutical Sciences (supra). The agents may be formulated as solution aerosols, dispersion or suspension aerosols of dry powders, emulsions or semisolid preparations. The aerosol may be delivered using any propellant system known to those skilled in the art. The aerosols may be applied to the upper respiratory tract, for example by nasal inhalation, or to the lower respiratory tract or to both. The part of the lung that the medicament is delivered to may be determined by the disorder. In one particularly preferred embodiment, delivery may be to, or achieve expression in, proximal bronchial epithelial and/or submucosal gland cells.

In some embodiments, and in particular where intranasal delivery is to be used, the medicaments may comprise a humectant. This may help reduce or prevent drying of the mucus membrane and to prevent irritation of the membranes. Suitable humectants include, for instance, sorbitol, mineral oil, vegetable oil and glycerol; soothing agents; membrane conditioners; sweeteners; and combinations thereof. The medicaments may comprise a surfactant. Suitable surfactants include non-ionic, anionic and cationic surfactants. Examples of surfactants that may be used include, for example, polyoxyethylene derivatives of fatty acid partial esters of sorbitol anhydrides, such as for example, Tween 80, Polyoxyl 40 Stearate, Polyoxy ethylene 50 Stearate, fusieates, bile salts and Octoxynol.

The medicaments of the present invention may, for instance, be delivered by any device adapted to introduce one or more therapeutic compositions into the upper and/or lower respiratory tract. In some preferred embodiments, the devices of the present invention may be metered-dose inhalers. The devices may be adapted to deliver the therapeutic compositions of the invention in the form of a finely dispersed mist of liquid, foam or powder. The device may use a piezoelectric effect or ultrasonic vibration to dislodge powder attached on a surface such as a tape in order to generate mist suitable for inhalation. The devices may use any propellant system known to those in the art including, but not limited to, pumps, liquefied-gas, compressed gas and the like.

Devices of the present invention typically comprise a container with one or more valves through which the flow of the therapeutic composition travels and an actuator for controlling the flow. Suitable devices for use in the present invention may be seen, for example, in Remington's Pharmaceutical Sciences (supra). The devices suitable for administering the constructs of the invention include inhalers and nebulisers such as those typically used to deliver steroids to asthmatics. In some cases, where the subject is for example a child, a spacer may be used to facilitate effective administration from the inhaler.

Various designs of inhalers are available commercially and may be employed to deliver the medicaments of the invention. These include the Accuhaler, Aerohaler, Aerolizer, Airmax, Autohaler, Clickhaler, Diskhaler, Easibreathe inhaler, Fisonair, Integra, Jet inhaler, Miat-haler, Novolizer inhaler, Pulvinal inhaler, Rotahaler, Spacehaler, Spinhaler, Syncroner inhaler and Turbohaler devices.

A construct for use in accordance with the invention will generally be administered via the airways, e.g. into the nasal cavity, trachea or lungs, but in some instances intravenous delivery to lung tissue may be permissible. For example, intravenous delivery of a construct in accordance with the invention to treat lung cancer may be preferred where the tumour(s) are readily accessible from the lung capillary bed. Various means of targeting recombinant constructs for tissue specific or tumour specific delivery of therapeutic agents have previously been described which may be applied to the constructs of the invention. Vectors for use in accordance with the invention may be delivered into the airways by, for example, means of a feeding catheter introduced into the nasal cavity or by means of a bronchoscope. Delivery for therapy in accordance with the invention may however more preferably be by means of a nebuliser or other aerosolisation device provided the integrity of the vector is maintained.

In embodiments where it is desired to administer the medicaments to, or via, the respiratory tract the particle size of the medicament may be chosen on basis of the desired part of the respiratory tract which it is desired to administer the medicament to.

The medicaments of the invention may take a variety of forms. In cases where they are to be administered via the respiratory tract they may be in the form of powders, powder microspheres, solutions, suspensions, gels, nano-particle suspensions, liposomes, emulsions or microemulsions. The liquids present may be water or other suitable solvents such as a CFC or HFA. In the case of solutions and suspensions these may be aqueous or involve solutions other than water.

In a particularly preferred instance, constructs of the invention are administered to the lung and in particular to the airways of the lung. In an especially preferred instance, delivery to the airways may be via the use of liposomes. In particular, the construct may be complexed with a cationic lipid based gene transfer formulation and in particular with GL67 or with PEI.

The constructs of the invention may be formulated as pharmaceutical preparations. This can be done using standard pharmaceutical formulation chemistries and methodologies, which are available to those skilled in the art. For example, compositions containing one or more constructs can be combined with one or more pharmaceutically acceptable excipients or vehicles to provide a pharmaceutical composition. Thus, the present invention provides a pharmaceutical composition comprising a construct of the invention and a pharmaceutically acceptable carrier and excipient.

Auxiliary substances, such as wetting or emulsifying agents, pH buffering substances and the like, may be present in the excipient or vehicle. These excipients, vehicles and auxiliary substances are generally pharmaceutical agents which may be administered without undue toxicity and which, in the case of vaccine compositions will not induce an immune response in the individual receiving the composition. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. It is also preferred, although not required, that the preparation will contain a pharmaceutically acceptable excipient that serves as a stabilizer, particularly for peptide, protein or other like molecules if they are to be included in the composition. Examples of suitable carriers that also act as stabilizers include, without limitation, pharmaceutical grades of dextrose, sucrose, lactose, trehalose, mannitol, sorbitol, inositol, dextran, and the like. Other suitable carriers include, again without limitation, starch, cellulose, sodium or calcium phosphates, citric acid, tartaric acid, glycine, high molecular weight polyethylene glycols (PEGs), and combinations thereof. A thorough discussion of pharmaceutically acceptable excipients, vehicles and auxiliary substances is available in REMINGTON'S PHARMACEUTICAL SCIENCES (Mack Pub. Co., N.J. 1991), incorporated herein by reference.

Certain facilitators of nucleic acid uptake and/or expression ("transfection facilitating agents") can also be included in the compositions, for example, facilitators such as bupivacaine, cardiotoxin and sucrose, and transfection facilitating vehicles such as liposomal or lipid preparations that are routinely used to deliver nucleic acid molecules. Anionic and neutral liposomes are widely available and well known for delivering nucleic acid molecules (see, e.g., *Liposomes: A Practical Approach*, (1990) RPC New Ed., IRL Press). Cationic lipid preparations are also well known vehicles for use in delivery of nucleic acid molecules. Suitable lipid preparations include DOTMA (N-[1-(2,3-dioleyloxy)propyl]-N,N,N-trimethylammonium chloride), available under the tradename Lipofectin™, and DOTAP (1,2-bis(oleyloxy)-3-(trimethylammonio)propane), see, e.g., Feigner et al. (1987) *Proc. Natl. Acad. Sci. USA* 84:7413-7416; Malone et al. (1989) *Proc. Natl. Acad. Sci. USA* 86:6077-6081; U.S. Pat. Nos. 5,283,185 and 5,527,928, and International Publication Nos WO 90/11092, WO 91/15501 and WO 95/26356. These cationic lipids may preferably be used in association with a neutral lipid, for example DOPE (dioleyl phosphatidylethanolamine). Still further transfection-facilitating compositions that can be added to the above lipid or liposome preparations include spermine derivatives (see, e.g., International Publication No. WO 93/18759) and membrane-permeabilizing compounds such as GALA, Gramicidine S and cationic bile salts (see, e.g., International Publication No. WO 93/19768).

In an especially preferred embodiment of the invention a construct may be administered using a cationic lipid. In particular cationic lipids comprising a spermine group and preferably a spermine group linked to a cholesterol anchor may be employed. In a preferred instance such agents may be employed with DOPE, particularly at 1:1 to 1:5 and preferably 1:1.5 to 1:2.5 and especially 1:2 molar ratios. One especially preferred formulation is to employ GL67 (Lee et al., 1996, Hum. Gen. Ther. 7:1701-1717). In a further preferred instance, cationic lipids comprising a spermine group may be used in conjuction with PEG-DMP-5000 and in particular GL-67 may be used in conjunction with such a formulation. In one instance, the molar ratios employed may be any of those mentioned in relation to DOPE. Eastman, et al. (1997) *Hum Gene Ther* 8(6): 765-73 describes the use of PEG-DMP-5000.

In one instance, GL-67, DOPE and DMPE-PEG-5000 may be formulated using the construct and in particular as described in Eastman et al and Lee et al and also described in the Examples. Thus, in one instance GL-67, DOPE and DMPE-PEG-5000 are formulated and, for instance, freeze dried for storage. The formulation may be then rehydrated and liposomes prepared by methods such as vortexing, constructs may be added by combining equal volumes of DNA and GL67 and in particular at a ratio of 0.25:1 or for, instance, at from 1:16 to 1:1, preferably from 1:8 to 1:1, more preferably from 1:5 to 1:1 molar ratios. For aerolisation, for instance, ratios of GL67 to plasmid 0.1:1 to 1:1, preferably 0.3:1 to 1:1 and in particular from 0.5:1 to 1:1 mM may be employed and in particular 0.75:1 mM may be employed.

In another especially preferred embodiment of the invention the construct of the invention may be delivered using polyethylenimine (PEI) (Boussif et al., 1995, PNAS 92:7297-301). In particular, 1 to 100 kd, preferably 10 to 50 kd, preferably 15 to 35 and in particular 19 to 31 kd PEI may be employed. Such PEIs may be branched or linear and in particular branched. In a preferred instance, 22 kd linear and 25 kd branched PEIs may be employed.

Alternatively, the nucleic acid molecules of the present invention may be encapsulated, adsorbed to, or associated with, particulate carriers. In particular, they may be provided on core carriers for needleless injection. Suitable particulate carriers include those derived from polymethyl methacrylate polymers, as well as PLG microparticles derived from poly(lactides) and poly(lactide-co-glycolides). See, e.g., Jeffery et al. (1993) *Pharm. Res.* 10:362-368. Other particulate systems and polymers can also be used, for example, polymers such as polylysine, polyarginine, polyornithine, spermine, spermidine, as well as conjugates of these molecules. In a preferred embodiment, constructs of the invention are precipitated onto carriers in the presence of a nucleic acid condensing agent and a metal ion chelating agent. Preferred condensing agents include cationic polymers, in particular polyamines, and in particular a polyargine or a polylysine. Metal core carriers and in particular gold core carriers may be employed for needleless injection.

The compositions are administered to a subject in an amount that is compatible with the dosage formulation and that will be prophylactically and/or therapeutically effective. An appropriate effective amount will fall in a relatively broad range but can be readily determined by one of skill in the art by routine trials. The "Physicians Desk Reference" and "Goodman and Gilman's The Pharmacological Basis of Therapeutics" are useful for the purpose of determining the amount needed. For example, it is generally expected that an effective dose of the polynucleotide will fall within a range of about from 0.001 µg to 1 g. In particular, doses of from 0.1 to 500 mg, preferably from 10 to 400 mg, more preferably from 25 to 350 mg, even more preferably from 35 to 300 mg may be administered. In some instances, a dose of about 50 mg, 100 mg, 150 mg, 250 mg or 300 mg may be given or a dose of within 25 mg of such doses. In a preferred instance, the doses may be applied for aerosol deliver. In the case of intravenous administration the dose may, for instance, be any of those mentioned and in particular may be in the range of 0.1 to 100 mg, preferably 0.5 to 25 mg and even more preferably from 5 to 10 mg.

In some cases after an initial administration a subsequent administration of the construct may be performed. The administration may, for instance, be at least a week, two weeks, a month, two months or six months after the initial administration. In some instances, constructs of the invention may be administered at least once a week, once a fortnight, once a month or at longer intervals. The constructs may, for instance, be administered at intervals dictated by when the effects of the previous administration are decreasing.

Any two entities of the invention may be administered separately, sequentially or simultaneously. Thus two constructs or more constructs, where at least one construct is a construct of the invention, may be administered separately, simultaneously or sequentially and in particular two or more constructs of the invention may be administered in such a manner. The two may be administered in the same or different compositions. In a preferred instance, the two constructs may be delivered in the same composition.

Pharmaceutical compostions comprising a construct of the invention and any of the other agents discussed herein are provided.

Medicaments and Methods

The invention also provides for the use of a construct of the invention in a method for treatment of the human or animal body by therapy. The method may be to treat, prevent or ameliorate any of the conditions mentioned herein. In one instance, the method may be a method of gene therapy. In another instance, the method may be a method of vaccination or immunisation. In one instance, the vaccination or immunisation is to treat, prevent or ameliorate an infection, an autoimmune condition, allergy or cancer.

The invention also provides for the use of a construct of the invention in the manufacture of a medicament for use in treating a genetic disorder, chronic condition, cancer, allergy, autoimmunity, infection or a cancer. In a preferred instance, the invention provides for the manufacture of medicaments to treat any of the conditions mentioned herein. In a particularly preferred instance the disease to be treated is an airway disorder. In particular the airway disorder is selected from cystic fibrosis, asthma, emphysema, chronic obstructive pulmonary disorder, acute respiratory distress syndrome (ARDS), bronchitis, pulmonary oedema and lung cancer.

The invention also provides a method of treating a disorder comprising administering a construct of the invention in an effective amount to a subject suffering from such a disorder. Any of the conditions mentioned herein may be treated. The invention also provides agents comprising constructs of the invention and optionally any of the other integers specified herein for use in treating the conditions mentioned herein.

The present invention also provides a non-therapeutic method of expressing a sequence in a subject, the method comprising administering a construct of the invention encoding a non-therapeutic sequence for expression, wherein the hCEFI promoter is operably linked to a non-therapeutic sequence for expression.

The present invention also provides an in vitro or ex vivo method of expressing a gene in a cell, tissue or organ, the method comprising introducing a construct of the invention into said cells, tissue or organ.

Non-Human Animals & Cells

In a further embodiment, the invention provides a non-human animal or bird comprising a construct of the invention. The non-human animal may be any of those mentioned herein and in particular may be a rodent or an agriculturally important animal or bird such as, for instance, those mentioned herein.

Such non-human animals may be transgenics and hence may typically comprise the construct in all of the cells of their body. In other instances, the construct may only be present in, mainly be present in, or almost entirely be present in one of the tissues or cell types referred to herein.

In one embodiment, the invention therefore provides a transgenic animal comprising a construct of the invention. In addition, gene targeting may be used to introduce a promoter of the invention in a desired location of the genome of an animal.

Thus, the invention also provides a targeting construct comprising a promoter of the invention and typically at least two regions of homology with the genome of the intended animal to allow homologous recombination. The invention also provides isolated non-human stem cells and in particular embryonic stem cells comprising a promoter of the invention, particularly one introduced via gene targeting. In a further embodiment isolated human stem cells, including embryonic and non-embryonic and in particular non-embryonic stem cells are provided. Haematopoietic stem cells comprising a construct of the invention are provided.

The present invention also provides isolated cells comprising a construct of the invention and in particular from any of the tissues mentioned herein. In particular, liver and lung cells are provided. Cells types such as are mammalian HEK 293T, CHO, HeLa, BHK, 3T3 or COS cells are also provided which comprise promoters or constructs of the invention.

Below are examples of specific embodiments for carrying out the present invention. The examples are offered for illustrative purposes only, and are not intended to limit the scope of the present invention in any way.

EXAMPLES

Materials and Methods

Mice

Female BALB/c mice aged 6-8 weeks were used throughout the current study. Mice were housed in accordance with UK Home Office ethical and welfare guidelines and fed on standard chow and water ad libitum and allowed to acclimatize for at least 7 days prior to procedures being performed.

Plasmid DNA

Plasmid DNA was prepared using the QIAGEN EndoFree Plasmid Purification kit (QIAGEN Ltd, Crawley, UK), or by a proprietary method by Aldevron Inc (Fargo, N. Dak., USA). In all cases levels of contaminating endotoxin were <5 EU (endotoxin units) per mg of DNA. DNA was maintained in endonuclease-free water (Promega UK Ltd, Southampton, UK) at −80° C.

Preparation of GL67/pDNA and PEI/pDNA for Instillation

Plasmid DNA was complexed with GL67 (GL67=formulation of GL67, DOPE, DMPE-PEG-5000 described by Eastman, et al. (1997) *Hum Gene Ther* 8(6): 765-73 as described (Lee, et al. (1996) *Hum Gene Ther* 7(14): 1701-17). Briefly, freeze dried GL67 (Genzyme, Mass., USA) was hydrated to 1.21 mM with water for injection (WFI) (B. Braun Medical) and liposomes prepared by vortexing. Plasmid DNA and GL67 liposome complexes were prepared by combining equal volumes of DNA and GL67 solutions. Final formulations contained 80 μg plasmid DNA complexed with GL67 at a 0.25:1 molar ratio in 100 μl water for injection. 100 μl of the GL67/pDNA complexes was delivered by instillation into the mouse lung.

Alternatively, plasmid DNA was complexed with 25 kDa branched polyethylenimine (PEI) (Sigma, Missouri, USA) essentially as described (Densmore, et al. (2000). *Mol Ther* 1(2): 180-8). 4.3 mg/ml (0.1M of N) PEI solutions were prepared in PBS, filter sterilised and stored at 4° C. for no more than one month. To prepare PEI/pDNA at 10:1 N:P ratio, 25.8 μg of PEI was mixed with 20 μg pDNA to a total volume of 100 μl in WFI (0.2 mg/ml). 100 μl of the PEI/pDNA complexes was delivered into the mouse lung.

Instillation of Plasmid DNA into the Mouse Airways

Mice were anaesthetized by exposure to the volatile anaesthetic Metofane (methoxyflurane) (Mallinckrodt Veterinary Inc., Illinois, USA) until a balanced state of anaesthesia was achieved, as determined by a level of response to foot pad pinch. Plasmid DNA in either delivery formulation was delivered to lungs via the nose, while it was held vertically with closed mouth. A single continuous droplet was maintained by pipetting the dose volume with a Gilson P200 pipette (Gilson Inc., Middleton, Wis., USA), the liquid being taken up by the mouse under insufflation.

Preparation of GL67/pDNA and PEI/pDNA for Aerosolisation

For aerosolisation studies, GL67/plasmid DNA was prepared at a ratio of 0.75:1 mM. Liposomes were generated by hydrating GL67 to 11.4 mM with WFI. 10 ml of the final mixture containing 2.5 mg/ml of plasmid DNA complexed with GL67. PEI/plasmid DNA was prepared for a single aerosol delivery at a concentration of 0.2 mg/ml in a total volume of 10 ml in WFI, at N:P ratio of 10:1. The complexes were incubated at room temperature for 20 minutes before aerosolisation.

Aerosolisation of Plasmid DNA into the Mouse Airways

Mice were placed inside an 8.4 L exposure chamber (internal dimensions 24.6 cm×24.6 cm×13.8 cm). A maximum of 36 mice were placed within the chamber for any given aerosol exposure and the mice were free to move around within the chamber for the duration of the study. Once within the chamber the lid was secured and sealed into place using 38 mm wide electrical tape to create an aerosol tight seal. A total of 10 ml of gene transfer formulation was placed into the reservoir of either the Aerotech II (CIS-US Inc, Bedford, Mass., USA) jet nebuliser (for PEI/DNA aerosols) or the PARI LC+ (PARI GmbH, Starnberg, Germany) jet nebuliser (for GL67/DNA aerosols) and aerosol was generated by passing compressed gas from a cylinder through the device. Generated aerosol was directed from the nebuliser into the exposure chamber via a length of 15 mm internal diameter PVC tubing connected centrally into the roof of the chamber by means of a specially constructed polyacetyl adapter. Excess aerosol within the chamber was vented to the atmosphere by means of a 10 mm diameter tube located in one side of the chamber and connected to a 0.2 µm Midistart 2000 PTFE air filter (Sartorius AG, Goettingen, Germany) for experiments using the Aerotech II nebuliser. No filter was included for experiments using the PARI LC+ nebuliser as the generated back pressure was found to critically impair aerosol production. 10 ml of both complexes were aerosolised in approximately 30 minutes.

Collection of BALF & Preparation of Mouse Lung Homogenates

When required, mice were killed by exposure to a rising concentration of $CO_2$ or by cervical dislocation. To collect BALF, the trachea was exposed and cannulated, lungs were lavaged four times with 1 ml BALF solution (1 PBS, 0.1% w/v BSA, 0.05 mM EDTA) recovered and kept on ice. Lungs and trachea were removed en bloc and incubated in 200 µl 1× reporter lysis buffer (RLB) (Promega, Southampton, UK) at 4° C. for up to 30 minutes before storage at −80° C. Lungs were then thawed at room temperature and homogenised for 15-30 seconds at maximum power with an Ultra-Turrax T8 tissue homogeniser (Janke & Kunkel GmbH, Staufen, Germany). Lung lysates were centrifuged, for 5 minutes at 16,000 rcf in a microcentrifuge. Lysate supernatant was collected and transferred to a QlAshredder column (Qiagen, Crawley, UK) and centrifuged for a further two minutes. Lysates were stored at −80° C. and thawed at room temperature before being assayed for Luciferase activity and protein content.

Analysis of BALF—Neutrophil Counts & Cytokine Levels

Cells from the BALF were concentrated by centrifugation at 400 rcf for 10 minutes at 4° C. The cell pellet was re-suspended in 1.1 ml BALF solution; the supernatant was collected and retained for separate analysis. A 100 µl sample of the re-suspended cells was removed for counting nucleated cells. The sample was mixed with an equal volume of Turks solution (3% v/v glacial acetic acid, 1% v/v crystal violet) and nucleated cells counted on a haemacytometer.

Levels of TNF-α, IL-12 and IFN-γ in the BALF supernatant were quantitated using enzyme-linked immunosorbent assay (ELISA) Quantikine M Immunoassay kits (R&D Systems, Minneapolis, USA) according to the manufacturers instructions.

Quantification of Luciferase Activity

Luciferase activity in lung lysates was using the Luciferase Assay System (Promega, Southampton, UK) and a Turner Designs TD-20/20 Luminometer (Steptech Instrument Services). Luciferase activity was normalised against total lung protein quantified using the Bio-Rad Protein Standard Assay II kit (Bio-Rad, Larne, UK) using a SpectraMAX 250 spectrophotometer plate reader and SOFTmax® Pro software (Molecular Devices, Wokingham, UK).

Example 1

In order to study the effects of CpG dinucleotides various constructs, were administered to mice. The constructs were administered to mouse lung and the levels of cytokines and neutrophils in BALF were measured to assess induction of inflammation.

Figure 7A:
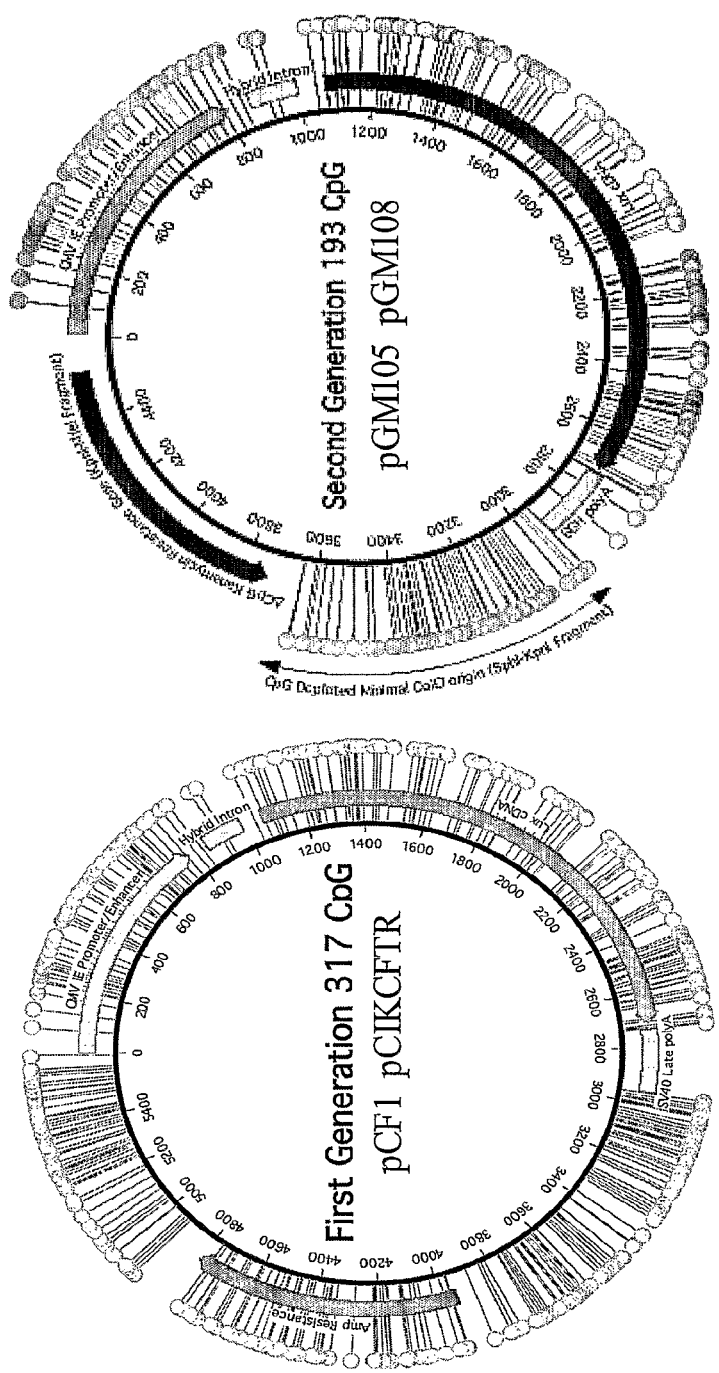
FIGS. 7a and b show first, second, third and fourth generation vectors with the number of CpG dinucleotides depicted as lollipops and indicated at the centre of each construct.
Figure 7B:
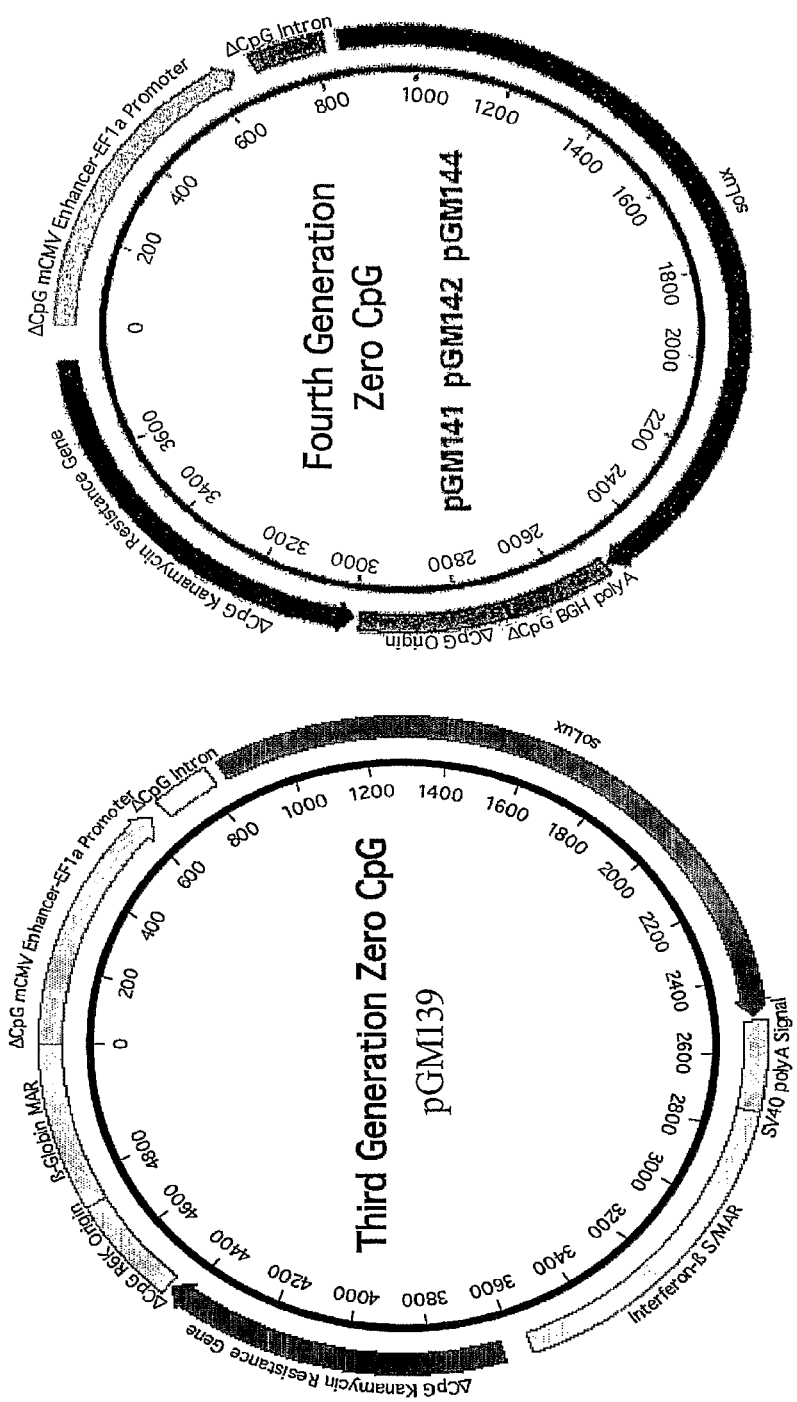

In the first set of experiments constructs comprising the following were administered:

(i) a first generation construct of the type depicted in FIG. 7 containing 317 CpG dinucleotides in the construct;

(ii) a second generation construct of the type depicted in FIG. 7 containing 193 CpG dinculeotides in the construct; and (iii) a third generation construct of the type depicted in FIG. 7 containing zero CpG dinucleotides in the construct.

Figure 4A:
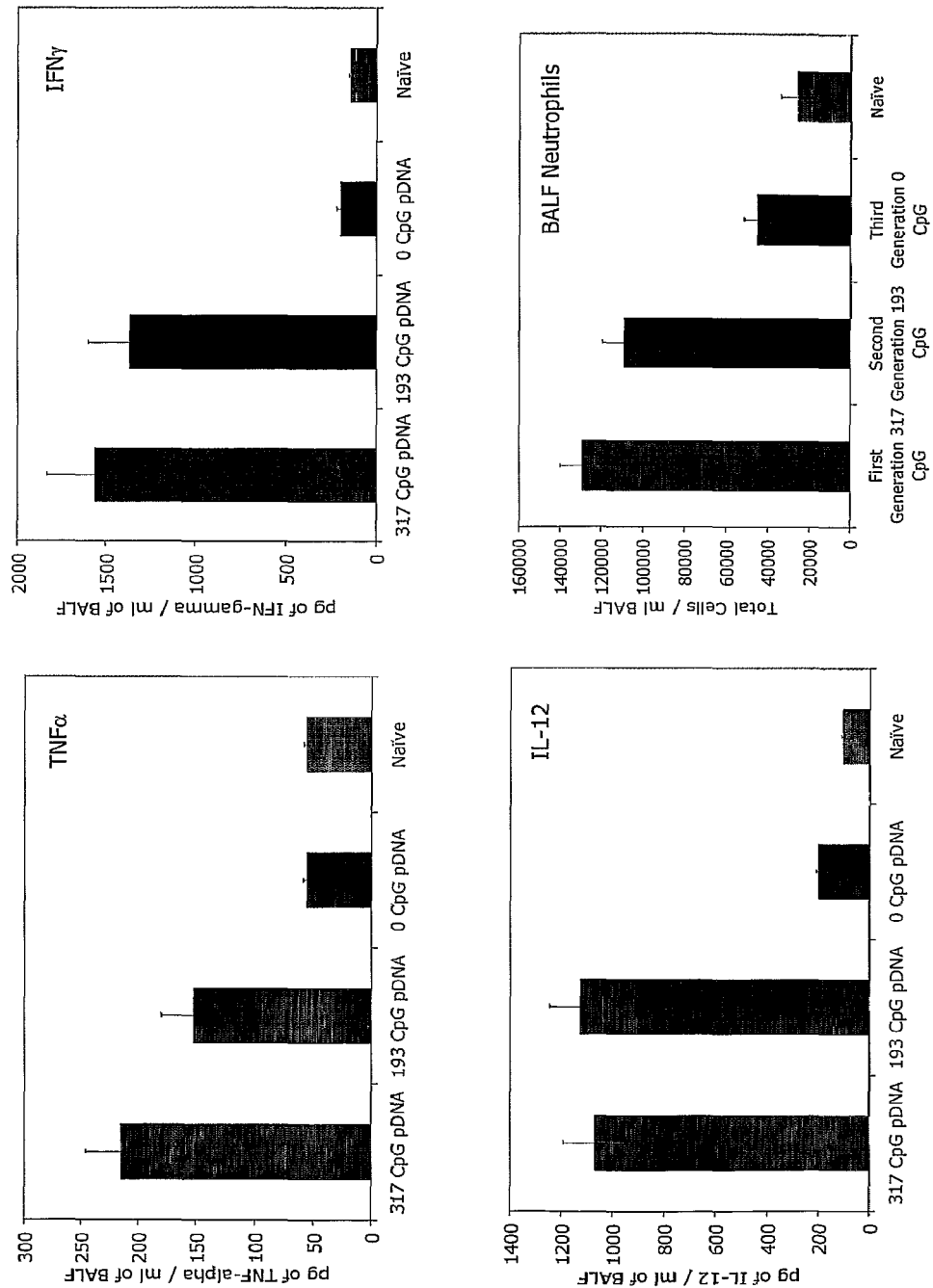
FIG. 4a depicts levels of flu like symptoms and lung inflammation following administration to mice of constructs with decreasing CpG dinucleotide content with, from left to right in each graph, 317 CpGs, 193 CpGs, 0 CpGs and control mice which have not had a construct administered. TNF-α, IFNγ and IL-12 levels are shown as well as the number of neutrophils in BALF (bronchoalveolar lavage lung fluid).

In addition, control naïve mice were employed. Levels of TNF-α, IFNγ and IL-12 were measured as well as the number of neutrophils in BALF. The results obtained are shown graphically in the four graphs in FIG. 4a. They show that the administration of constructs comprising no CpG dinucleotides eliminate almost entirely the increases in the inflammatory markers measured seen with the constructs comprising CpG dinucleotides.

In a further series of experiments the effect of the addition of a single CpG dinucleotide was measured. The following constructs were administered:

(i) a first generation construct of the type depicted in FIG. 7 with the construct containing 317 CpG dinucleotides;

(ii) a third generation construct of the type depicted in FIG. 7, but which has been modified to reintroduce a single CpG dinucleotide; and (iii) a third generation construct of the type depicted in FIG. 7 construct with zero CpG dinucleotides.

Figure 4B:
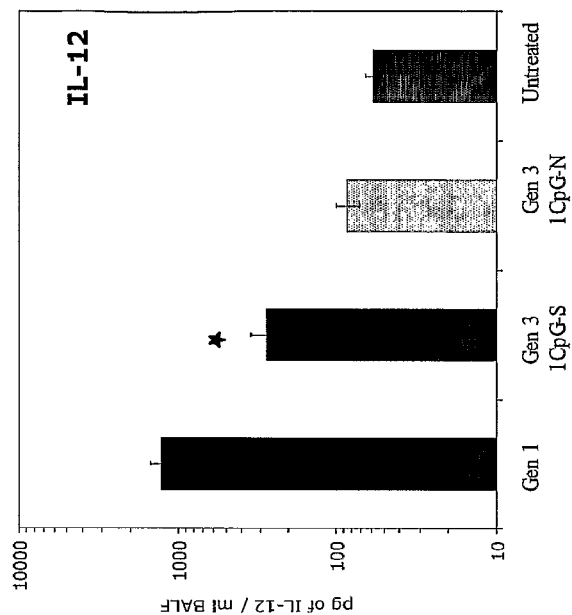
FIG. 4b shows the effect of adding a single CpG motif to a construct on the inflammatory response to the construct in the lung of a mouse. More specifically.
Figure 4B:
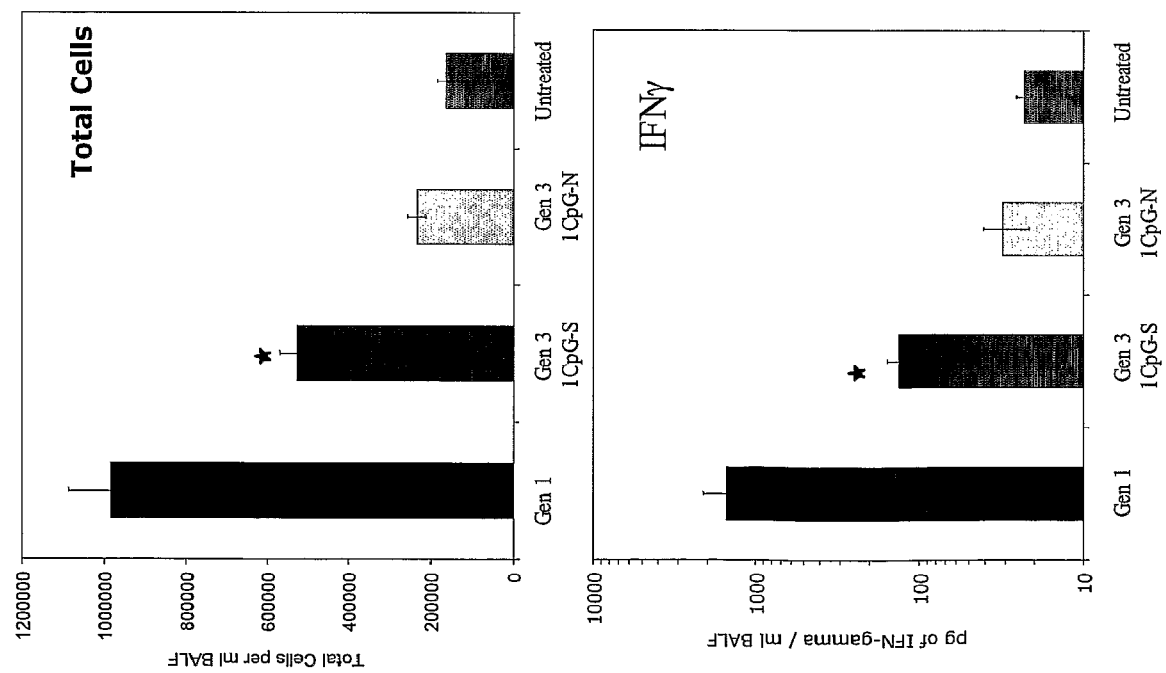

The results obtained are shown in the three graphs of FIG. 4b and show that the addition of just one CpG sequence is sufficient to direct flu like symptoms and lung inflammation.

Thus constructs employing zero CpG dinucleotides will help eliminate flu like symptoms and lung inflammation when constructs are administered in vivo.

First generation plasmids such as pCIK Lux and pUb Lux are described by Gill D R et al (2001) Gene Therapy October; 8(20):1539-46.

Third generation plasmids are derivatives of pCpG-LacZ available from Invivogen, the sequence of which can be found at www.invivogen.com/sequence/pCpG-LacZ_Seq.rtf.

Figure 4C:
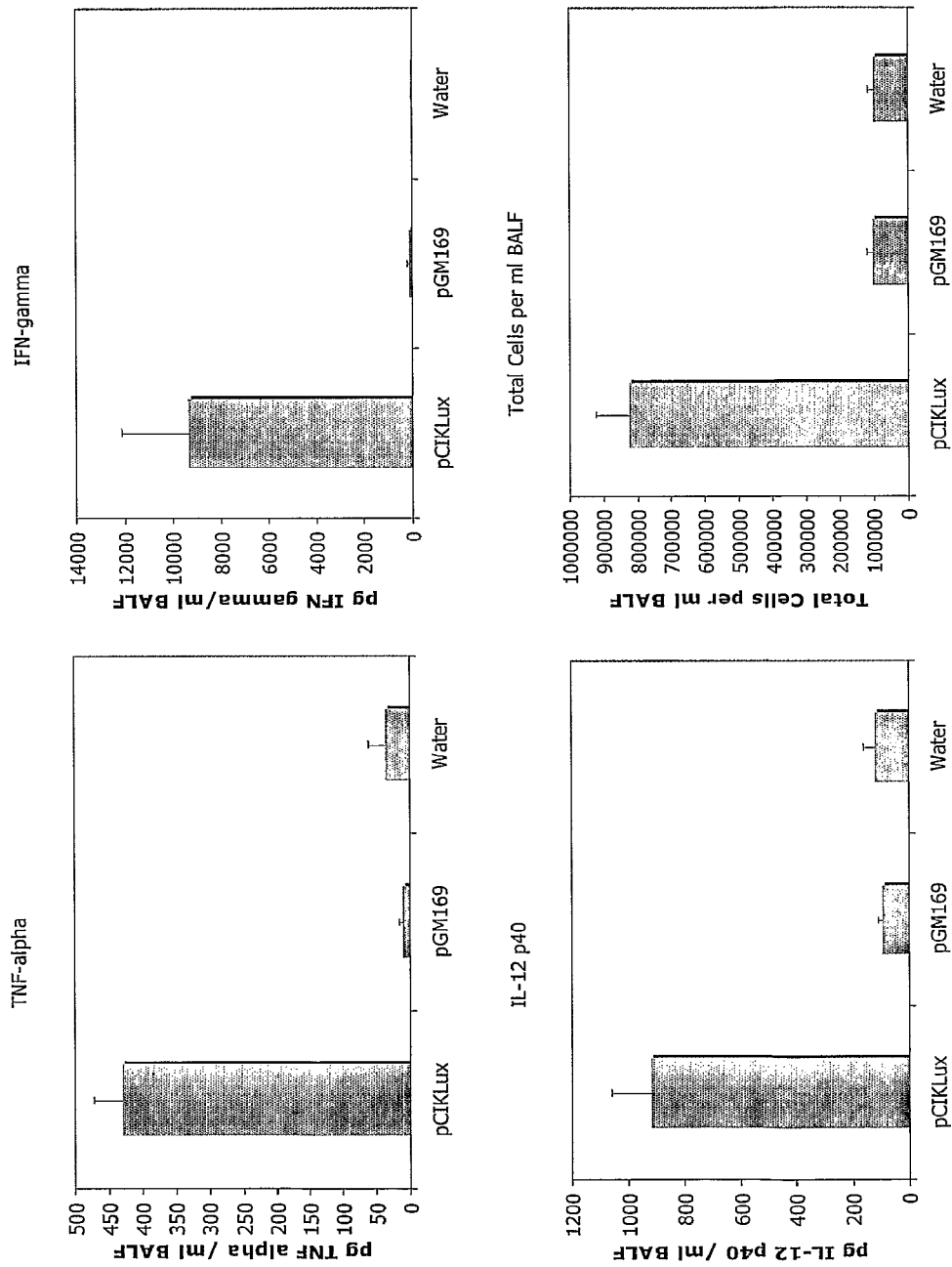
FIG. 4c shows that replacing the Lux gene with a CFTR gene with no Cpg dinucleotides has no effect on the inflammatory response observed.

To further support these observations, FIG. 4c shows the results obtained when mice were administered with:
(i) the pCIKLux construct—a first generation plasmid with 317 CpGs;
(ii) pGM169 which contains the CFTR coding sequence, the hCEFI promoter enhancer combination, and no CpGs. (pGM169 has the modified sequence of Seq ID No.2 in which nucleotide 2595 is C, nucleotide 3234 is T and nucleotide 3236 is C); and
(iii) water—as a negative control.

The results obtained show that in the absence of CpGs the constructs have cause little or no inflammatory response Example 2

The results obtained in Example 1 showed that the removal of CpG dinucleotides eliminated undesirable inflammatory responses due to the presence of the dinucleotides. However, the third generation constructs failed to give sustained and high level expression. Accordingly, further modifications were made to the constructs.

In particular, fourth generation constructs were generated introducing a hCEFI promoter consisting of a human CMV enhancer and the human EF1a promoter. In addition, further modifications were made to employ an alternative antibiotic resistance gene and to remove matrix attachment regions (MAR). The sequence of illustrative fourth generation constructs is provided in SEQ ID No: 1 (pGM160 construct with no coding sequence), SEQ ID No: 2 (pGM151 construct which includes encodes a CFTR polypeptide expressed from the hCEFI promoter and which has been codon optimised, similar results are achieved using a construct of SEQ ID No:2 in which nucleotide 2595 is C and nucleotides 3234 and 3236 are T and C respectively) and SEQ ID No: 4 (pGM144 construct which encodes a firefly luciferase polypeptide, soLux, expressed from the hCEFI promoter and which has been codon optimised.

In order to assess the efficacy of the hCEFI promoter the pGM144 construct was used. The firefly luciferase gene (soLux) under the transcriptional control of the hCEFI was used as a reporter gene. The luciferase reporter gene allows expression from the hCEFI promoter to be monitored and hence the level and length of expression can be measured.

In order to assess the efficacy of pGM144 aerosol delivery to mice two different formulations were used, namely GL67 and PEI aerosols. The pGM144 construct was assessed side-by side with a number of different constructs.

In particular, using GL67 aerosols comprising the constructs, the following constructs were administered:
(i) pGM144 (also referred to as pG4hCEFI soLux) which uses the hCEFI promoter for expression of luciferase and which has zero CpG dinucleotides in the construct;
(ii) pG2Ubc Lux (pGM105) which uses the human polyubiquitin C promoter for expression and comprises 245 CpG dinucleotides in the construct;
(iii) pG4GZB soLux (pGM142) which uses the human CMV enhancer and promoter and which has zero CpG dinucleotides in the construct;
(iv) pG4mCEFI soLux (pGM141) which employs the mouse CMV enhancer and the human EFIa promoter and has zero CpG dinucleotides in the construct; and
(v) pG1 CMV lux (pCILux) which uses the CMV IE promoter and enhancer for expression and comprises 317 dinucleotides in the construct.

In addition, the following constructs were administered using the cationic polymer PEI:

(i) pGM144 (pG4hCEFI soLux) which uses the hCEFI promoter for expression of luciferase and which has zero CpG dinucleotides in the construct;
(ii) pG4GZB soLux (pGM142) which uses the human CMV enhancer and promoter and which has zero CpG dinucleotides in the construct;
(iii) pG4 mCEFI soLux (pGM141) which employs the mouse CMV enhancer and the human EFIa promoter and has zero CpG dinucleotides in the construct; and
(iv) pG3 mCEFI Lux (pGM139) a further construct which employs the mouse CMV enhancer and the human EFIa promoter and has zero CpG dinucleotides in the construct. The construct also comprises matrix attachment regions.

Figure 5:
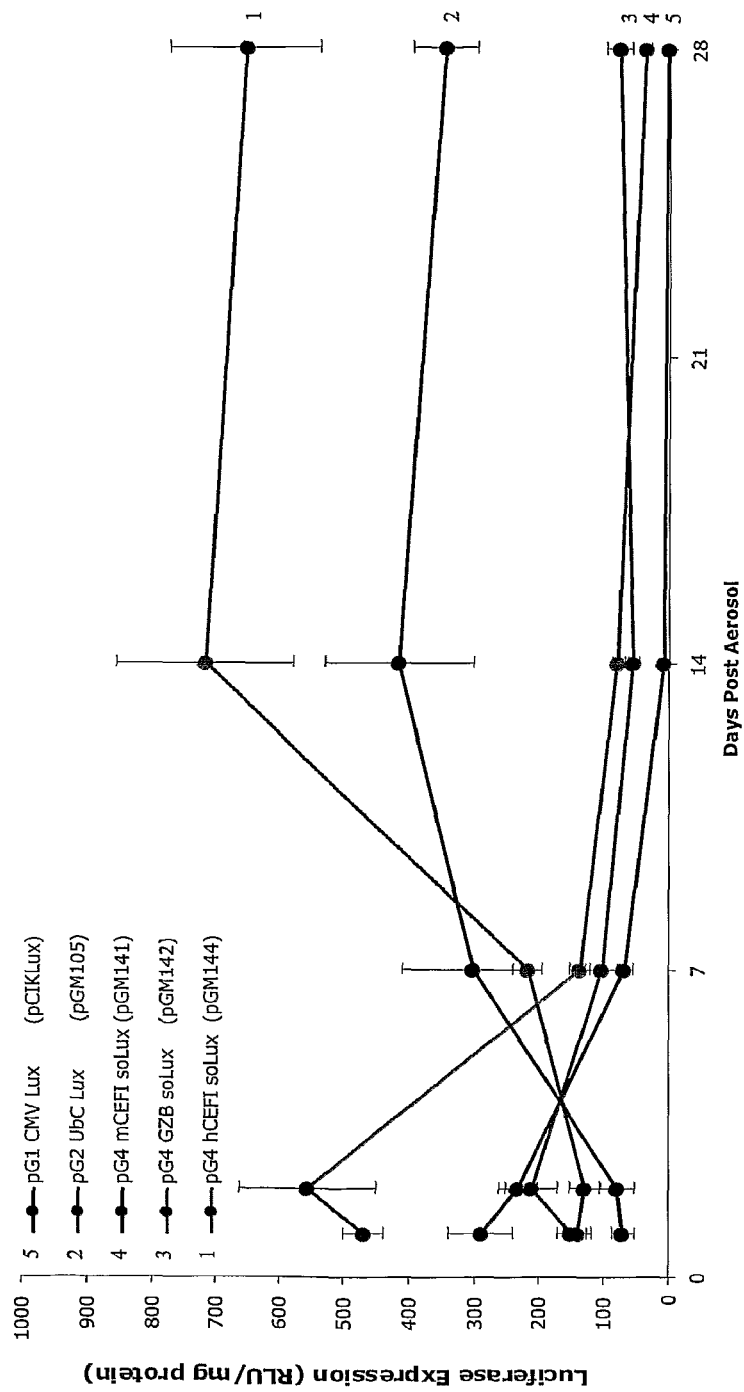
FIG. 5 shows expression levels in the lung with time following GL67 aerosol delivery of the constructs pG4hCEFI soLux (expression from a hCEFI promoter of the invention), pG4GZB soLux (employs the human CMV enhancer and promoter), pG4mCEFI soLux (employs the mouse CMV enhancer and the human EFIa promoter), pG2Ubc Lux (employs the human polyubiquitin C promoter) and pG1 CMV lux (which employs the CMV IE promoter and enhancer).
Figure 6:
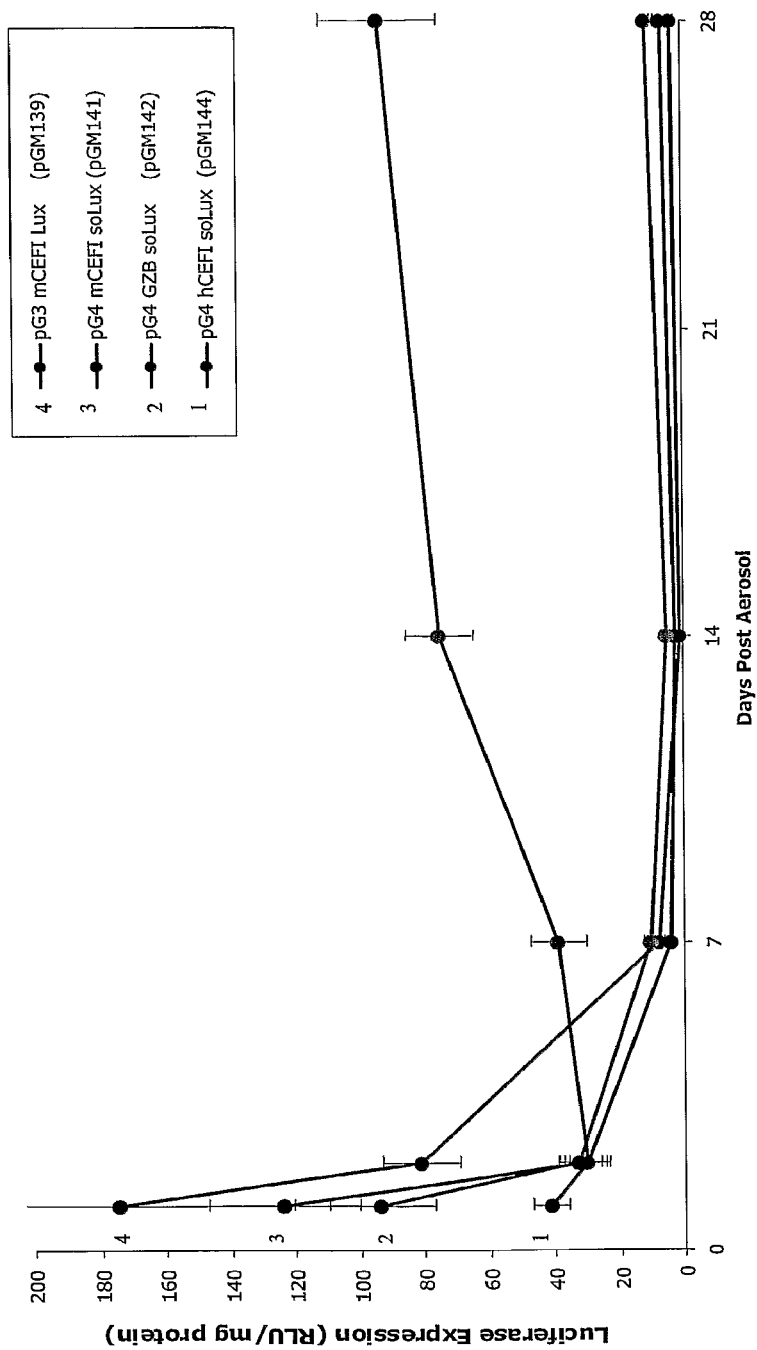
FIG. 6 shows expression levels in the lung with time following PEI aerosol delivery of the pG4 hCEFI soLux, pG4GZB soLux, pG4mCEFI soLux, and pG3mCEFI soLux constructs.

Unexpectedly, the pGM144 construct employing the hCEFI promoter of the invention was the only construct to give sustained and high level expression with GL67 (FIG. 5) and PEI (FIG. 6). None of the other constructs gave comparable expression with either GL67 or PEI delivery. The only other construct giving appreciable expression 28 days after delivery was the human polyubiquitin C promoter present in the pG2 UBC Lux construct that gave substantially less expression than the hCEFI promoter.

The results were surprising in particular given that the pGM141 construct has a composite of the mouse CMV enhancer and the human EF1a promoter and yet gives no significant expression, whereas the hCEFI promoter comprises a composite of the human CMV enhancer and human EF1a promoter and is far superior. There was no indication that the mouse CMV enhancer in combination with the human EF1a promoter would be anything other than functional.

The results obtained show that the hCEFI promoter can be used to obtain sustained and high expression used the reporter gene luciferase as a model for coding sequences in general. The mouse lung model serves as a good in vivo model and is particularly useful for airway disorders such as cystic fibrosis.

Example 3

The results obtained in Example 2 showed that the CpG free hCEFI enhancer promoter combination in a fourth generation CpG free plasmid backbone (pGM144) directed sustained and high level expression when complexed with either GL67 or PEI and delivered to the mouse lungs.

In a further series of experiments alternative permutations of the CpG containing or CpG free versions of the human CMV enhancer, human elongation factor 1 alpha promoter and plasmid backbone were evaluated.

The following expression constructs were complexed with GL67 and delivered to the mouse lungs by aerosolisation.
(i) pGM146 (also referred to as pG2 EF1a Lux) a second generation construct that uses the native Elongation Factor 1a promoter for expression of luciferase. Importantly, the promoter contains 18 CpGs within the promoter region and a total of 245 CpGs in the entire construct.
(ii) pGM147 (also referred to as pG2 CEF1a Lux) a second generation construct that uses the native human CMV enhancer coupled to the native Elongation Factor 1a promoter for expression of luciferase. Importantly, the enhancer promoter region contains 35 CpGs within the enhancer/promoter region and a total of 262 CpGs in the entire construct.

(iii) pGM157 (also referred to as pG2 hCEFI Lux) a second generation construct that uses the CpG free human CMV enhancer coupled to the CpG free Elongation Factor 1a promoter (the hCEFI enhancer promoter) for expression of luciferase. Importantly, the enhancer promoter region contains 0 CpGs within the enhancer/promoter region and a total of 149 CpGs in the entire construct.

(iv) pGM144 (also referred to as pG4 hCEFI soLux) described above a fourth generation construct using the CpG free human CMV enhancer coupled to the CpG free Elongation Factor 1a promoter (the hCEFI enhancer promoter) for expression of luciferase. Importantly, the entire construct contains 0 CpGs.

Figure 8:
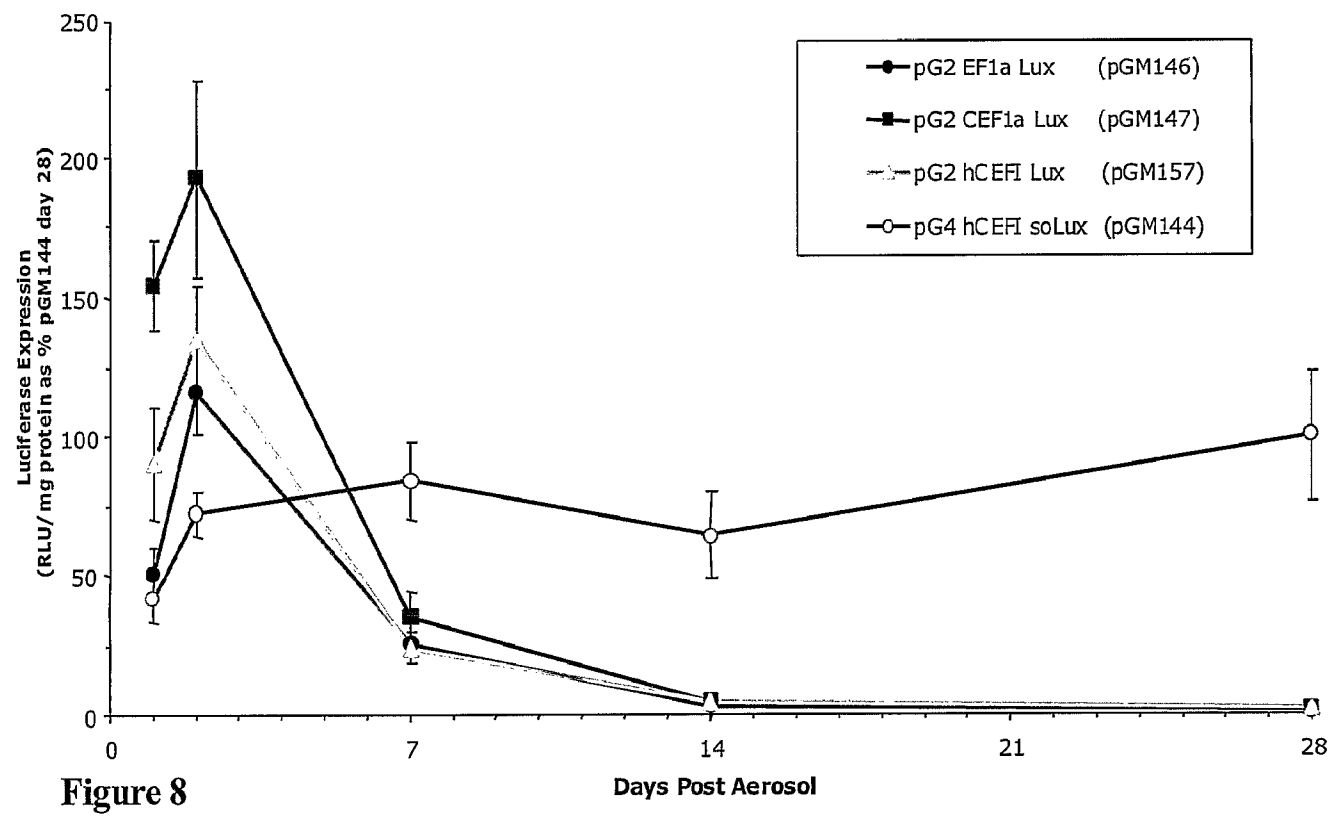

The results obtained are shown in FIG. 8, the only construct that directed sustained high level mouse lung expression was the CpG free pGM144 in which expression was directed by the hCEFI enhancer/promoter. The hCEFI enhancer/promoter in the context of a second generation CpG containing plasmid backbone (pGM157) directed transient lung luciferase expression. Furthermore, the native CpG containing Elongation Factor 1 alpha promoter with (pGM147) or without (pGM146) the human CMV enhancer directed transient lung luciferase expression.

The results of Example 2 and 3 demonstrate that of the constructs described only the combination of the hCEFI enhancer/promoter in the context of the CpG free fourth generation plasmid backbone directs sustained high level lung transgene expression. Neither the use of the hCEFI enhancer/promoter in a second generation plasmid backbone, or the use of alternative enhancer/promoter combinations in the fourth generation plasmid backbone directed sustained high level lung transgene expression.

Example 4

The results obtained in Examples 2 and 3 show that the CpG free hCEFI enhancer promoter combination in a fourth generation CpG free plasmid backbone (pGM144) directed sustained and high level expression when complexed with either GL67 or PEI and delivered to the mouse lungs for at least 28 days.

In a further series of experiments lung gene expression was evaluated over an extended period of time after administration and compared lung gene expression with a derivative of pGM148 in which the CpG free version of the human CMV enhancer was removed.

The following expression constructs were complexed with GL67 and delivered to the mouse lungs by aerosolisation:

(i) pGM144 (also referred to as pG4 hCEFI soLux) described above a fourth generation construct using the CpG free human CMV enhancer coupled to the CpG free Elongation Factor 1a promoter (the hCEFI enhancer promoter) for expression of luciferase. Importantly, the entire construct contains 0 CpGs.

(ii) pGM148 (also referred to as pG4 EFI soLux) is a fourth generation construct using only the CpG free Elongation Factor 1a promoter for expression of luciferase. Importantly, the entire construct contains 0 CpGs.

Figure 9:
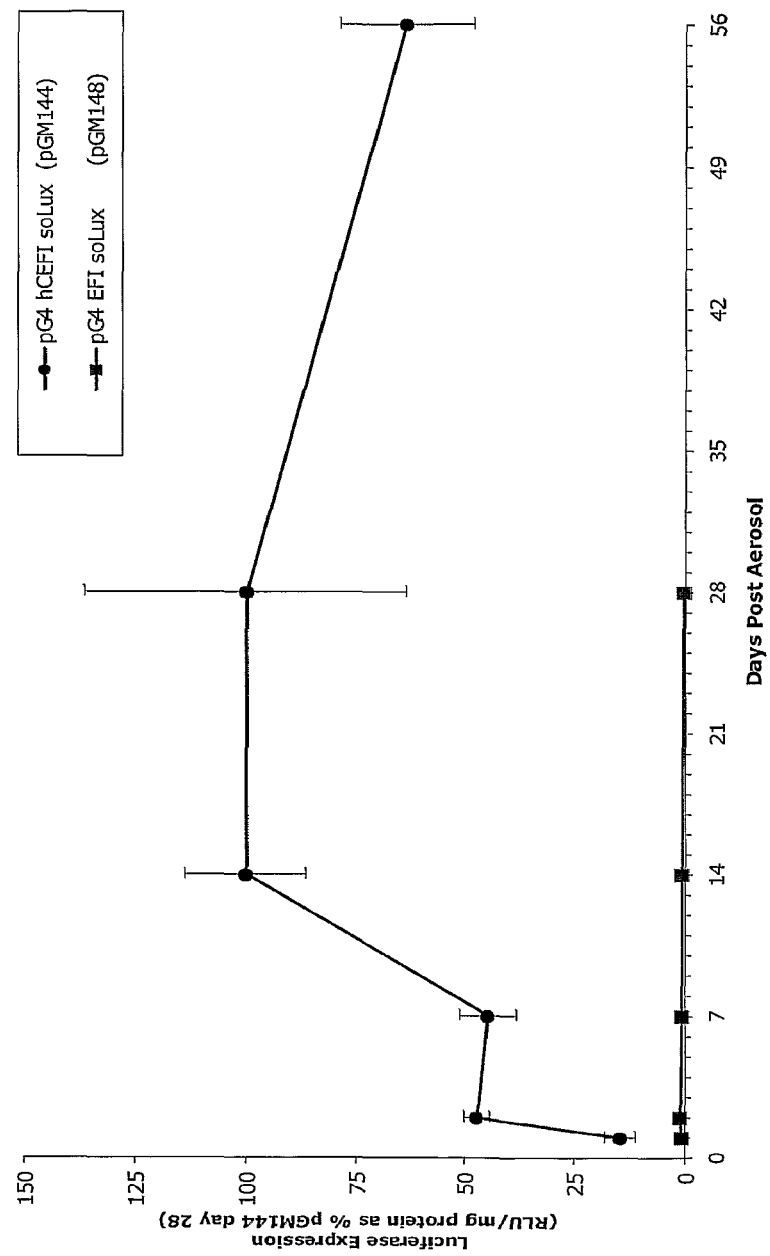
FIG. 9 shows expression levels in the lung over 56 days following GL67 aerosol delivery of the constructs pG4hCEFI soLux and pG4EF1 soLux (employs a CpG free human EFIa promoter only and the entire construct contains no CpGs).

The results obtained are shown in FIG. 9. The only construct that directed sustained high level mouse lung expression was the CpG free pGM144 in which expression was directed by the hCEFI enhancer/promoter. The EFI promoter alone in the context of a fourth generation CpG free plasmid backbone (pGM148) directed negligible lung luciferase expression. Furthermore, pGM144 shows sustained high level lung luciferase expression for at least 56 days after a single administration.

CONCLUSIONS

In the expression of sequences high level and sustained expression are desirable. The hCEFI promoter provides such expression and has been demonstrated to be superior to an array of promoters. In addition, the elimination, or at least reduction of, inflammation induced by vectors when administered in vivo is also desirable. The work described here also shows that elimination of CpG sequences found in common plasmid expression vectors abolishes inflammation associated with such sequences and in particular when constructs are administered to the lung. Thus, high level and sustained expression and reduction or elimination of unwanted inflammation can be achieved.

The invention claimed is:

1. A nucleic acid construct comprising a hCEFI promoter operably linked to a sequence for expression, wherein the hCEFI promoter consists of nucleotides 7 to 538 of SEQ ID NO:1, wherein the hCEFI promoter does not comprise any CpG dinucleotides, and wherein a non-promoter sequence of the construct comprises a CpG dinucleotide.

2. The construct of claim 1, wherein the construct is a plasmid construct.

3. The construct of claim 1, wherein the construct comprises a kanamycin resistance marker.

4. The construct of claim 1, wherein the sequence for expression encodes a therapeutic polypeptide.

5. A pharmaceutical composition comprising the construct of claim 1 and a pharmaceutically acceptable carrier or excipient.

6. The construct of claim 1, wherein the sequence for expression operably linked to the hCEFI does not comprise any CpG dinucleotides.

7. The construct of claim 4, wherein the encoded therapeutic polypeptide comprises a CFTR polypeptide, wherein the sequence for expression comprises: (i) the contiguous nucleotides 738 to 5180 of SEQ ID No: 2; (ii) the contiguous nucleotides 738 to 5180 of SEQ ID No: 2 in which nucleotide 2595 is C and/or nucleotide 3234 and 3236 are T and C respectively, (iii) a sequence having at least 70% sequence identity to the sequence of (i) or (ii); or (iv) a complement of the sequence of (i), (ii), or (iii).

* * * * *